United States Patent

Miyazawa et al.

(10) Patent No.: US 6,168,728 B1
(45) Date of Patent: Jan. 2, 2001

(54) ACETYLENE DERIVATIVES, AND LIQUID CRYSTAL COMPOSITION AND LIQUID CRYSTAL DISPLAY DEVICE EACH COMPRISING THE SAME

(75) Inventors: Kazutoshi Miyazawa; Kouji Koga; Shuichi Matsui; Norihisa Hachiya; Etsuo Nakagawa, all of Ichihara (JP)

(73) Assignee: Chisso Corporation, Osaka (JP)

( * ) Notice: Under 35 U.S.C. 154(b), the term of this patent shall be extended for 0 days.

(21) Appl. No.: 09/380,875

(22) PCT Filed: Mar. 13, 1997

(86) PCT No.: PCT/JP97/00795

§ 371 Date: Sep. 10, 1999

§ 102(e) Date: Sep. 10, 1999

(87) PCT Pub. No.: WO98/40336

PCT Pub. Date: Sep. 17, 1998

(51) Int. Cl.[7] .......................... C09K 19/06; C09K 19/34; C09K 19/30; C09K 19/12; C07C 13/00

(52) U.S. Cl. ................................. 252/299.6; 252/299.61; 252/299.63; 252/299.66; 585/23; 585/25

(58) Field of Search ............................. 252/299.6, 299.63, 252/299.66, 299.61; 585/23, 25

(56) References Cited

U.S. PATENT DOCUMENTS

| 5,154,857 | * | 10/1992 | Goto et al. ....................... 252/299.63 |
| 5,356,558 | * | 10/1994 | Yamada et al. .................. 252/299.01 |
| 5,792,387 | * | 8/1998 | Hachiya et al. .................. 252/299.6 |

FOREIGN PATENT DOCUMENTS

| 8-12599 | * | 1/1996 | (JP) . |
| 9-216841 | * | 8/1997 | (JP) . |

* cited by examiner

Primary Examiner—C. H. Kelly
(74) Attorney, Agent, or Firm—Browdy and Neimark

(57) ABSTRACT

The present invention provides new liquid crystalline compounds having a high optical anisotropy value and excellent compatibility with the other liquid crystals, and liquid crystal composition comprising the compounds.

The liquid crystalline compounds are represented by the general formula (1):

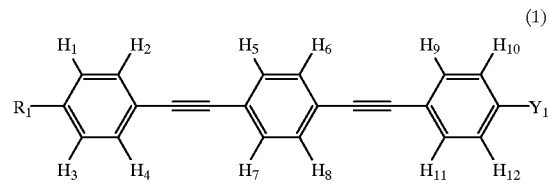

(1)

wherein $H_1$, $H_2$, $H_3$, $H_4$, $H_5$, $H_6$, $H_7$, $H_8$, $H_9$, $H_{10}$, $H_{11}$ and $H_{12}$, each independently, represent H, F or Cl, at least one of $H_1$, $H_2$, $H_3$, $H_4$, $H_9$, $H_{10}$, $H_{11}$ and $H_{12}$ is F or Cl, $R_1$ represents an alkyl group of $C_{1-20}$, in which methylene groups may be replaced by —O—, —S—, —Si—, —CH=CH— or —C≡C—, any hydrogen atoms may be replaced by a halogen atom, and $Y_1$ is replaced by $R_1$, F, Cl, Br, I or a cyano group.

21 Claims, No Drawings

ACETYLENE DERIVATIVES, AND LIQUID CRYSTAL COMPOSITION AND LIQUID CRYSTAL DISPLAY DEVICE EACH COMPRISING THE SAME

CROSS REFERENCE TO RELATED APPLICATION

The present application is the national stage under 35 U.S.C. 371 of PCT/JP97/00795, filed Mar. 13, 1997.

TECHNICAL FIELD

The present invention relates to liquid crystalline compounds, liquid crystal materials using the compounds and liquid crystal display devices. More particularly, the present invention relates to new liquid crystalline compounds, which are preferable as components of liquid crystal materials having compatibility with many liquid crystalline compounds and high optical anisotropy (may be abbreviated as $\Delta n$, hereinafter), liquid crystal materials having high $\Delta n$ and excellent compatibility with the other liquid crystal compounds, and liquid crystal display devices using them.

BACKGROUND ART

Liquid crystal display devices are used for watches, desk-top calculators, miscellaneous measuring apparatus, metering panels for automobiles, word processors, electronic notebooks, printers, computers, television sets and the like.

Liquid crystal display devices are obtained by using liquid crystal materials having properties of optical anisotropy and dielectric anisotropy (may be abbreviated as $\Delta\epsilon$, hereinafter). The display modes are principally dynamic scattering (DS) mode, guest-host (G.H) mode, twist nematic (TN) mode, super twist nematic (STN) mode, thin film transistor (TFT) mode, surface stabilized ferroelectric liquid crystal (SSFLC) mode and the like. Driving modes are static driving mode, time-division driving mode, active matrix driving mode, two-frequency driving mode and the like.

In these modes, STN mode is now the most broadly used for the high display quality and low production cost. Various characteristics are required in the liquid crystal materials used for the STN mode, and the following is generally important:

(1) Quick electric-optical response time,
(2) Steep transparency per applied voltage,
(3) Broad driving temperature range, and
(4) Low driving voltage.

For showing the above characteristics, the liquid crystalline compounds for constituting liquid crystal materials are required to have the following characteristics. Namely:

(1) high optical anisotropy,
(2) when the liquid crystal compound is added to a liquid crystal composition, the temperature region of the nematic phase does not reduce, and the phase separation such as crystal deposition is difficult in the low temperature region,
(3) low viscosity,
(4) chemical stability, and
(5) high bend to splay elasticity constant ratio ($K_{33}/K_{11}$).

It is described more specifically hereinafter. It has been known that the viscosity of liquid crystals is an element that controls the response speed of liquid crystal molecules aligning in a display device to the electric field applied (Phys. Lett., 39A, 69 (1972). Namely, to prepare the liquid crystal composition showing high-speed response, it is preferable to prepare liquid crystal compositions by using liquid crystalline compounds having very low viscosity in large quantities.

The liquid crystalline compounds having low viscosity have been earnestly studied. Such studies have brought bicyclic compounds having simple structures, such as bicyclohexanes and phenyl cyclohaxanes having the lowest viscosity. However, it is very difficult to find out the compounds having simpler structure, or lower viscosity than the compounds known now. A method for resolving the problems is to reduce the thickness of a liquid crystal cell (it may be called as "d" hereinafter). By reducing the cell thickness in comparison with that of conventional liquid crystal cell, high-speed response is obtained.

However, considering the display quality, the adequate retardation value (d·$\Delta n$), which is the first minimum condition described in Appl. Phys. Lett. 38(7), 497, should not deviate from the optimum value. Namely, it is needed to maintain a constant product of optical anisotropy and cell thickness and to reduce the cell thickness. Accordingly, it needs to make higher the $\Delta n$ of liquid crystal materials by using as a component the liquid crystalline compound having a very higher optical anisotropy value than that of conventional compounds.

The steepness of applied voltage to transparency characteristics (may be abbreviated as V-T characteristics, hereinafter) is highly caused by the bend to splay elasticity constant ratio $K_{33}/K_{11}$ (Proc. of Japan Display, 388 (1986)). According to the report, the liquid crystal having a high elasticity constant ratio has steeper V-T characteristics. By using liquid crystal materials having good V-T characteristics, liquid crystal display having higher display quality can be attained.

For the availability in a broader temperature region, liquid crystal compositions having a nematic phase at a low temperature are especially demanded. At the low temperature region, liquid crystal compositions, which do not deposit crystals and do not show a smectic phase, are naturally demanded. To fit liquid crystal materials with many characteristics required of each display device, a mixture of several kinds or twenties of liquid crystalline compounds constitutes a liquid crystal material. Accordingly, it is very important that the liquid crystalline compounds used have high compatibility with the other liquid crystalline compounds at the low temperature region.

It becomes important problem to reduce consumption power of liquid crystal display devices recently, so that it is necessary to lower the driving power of the devices. To lower the driving power, it is needed to reduce the threshold voltage (may be abbreviated as Vth, hereinafter). The threshold voltage is a function of a dielectric anisotropy value, and the following relation is reported in Mol. Cryst. Liq. Cryst., 12, 57 (1970).

$$V_{th} = \pi (K/\epsilon 0 \Delta\epsilon)^{1/2},$$

wherein K is an elastic constant and $\epsilon 0$ is a dierectric constant in vacuum. In the relation, when the liquid crystal materials having low driving power is demanded, it is needed to use liquid crystal materials having a high dielectric anisotropy value.

Since liquid crystal display devices are frequently used at a high temperature, for example, under severe conditions such as outdoors, the liquid crystalline compounds used for liquid crystal compositions should have sufficiently high chemical stability.

It is further important to have a little temperature dependence as an important factor in several characteristics. The practical liquid crystal display devices must be maintained with various surroundings, at an especially broad temperature region (for example, −20~120° C.) not so as to largely change the display quality. To satisfy the demand, it is necessary to use liquid crystal materials having very little temperature dependence of various characteristic values.

The liquid crystal materials for STN display devices have been studied, and many excellent compounds have been developed. As a compound having a particularly high elasticity constant ratio $K_{33}/K_{11}$, an alkenyl compound has been obtained and a liquid crystal material having steep V-T characteristics has been practically used.

However, at the present time, only a few example of liquid crystalline compound having remarkably high $\Delta n$ has been known and practically used.

Compounds having high $\Delta n$ that have been first practically used are tolan compounds as shown by formula (10), which have been disclosed by J. Malthete et al (Mol. Cryst. Liq. Cryst., 23, 233 (1973)). The tolan compounds have relatively high $\Delta n$ and now are practically used. However, the optical anisotropy value is 0.20 and it is not enough for practical use.

To resolve the problem, the tolan derivative having alkyl groups as shown by formula (11) has been developed (Japanese Patent Application Laid-open No. sho-64-879) for increasing the polarization ratio. However, in spite of the increased optical anisotropy value (>0.20), the compatibility with the other many liquid crystal compounds is very low, and what is more the practical use of the compounds is limited by lack of chemical stability.

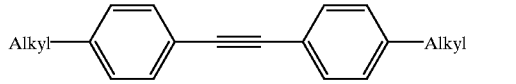
(10)

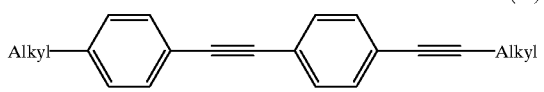
(11)

To obtain a compound having nematic phase at a high temperature, a compound represented by formula (12) has been prepared (Japanese Patent Application Laid-open No. hei 2-83340). Although the compound has a high optical anisotropy value and a high clearing point, the compatibility with the other many liquid crystalline compounds is very low, so that the compound is very impractical. To resolve the problem, the compound represented by formula (13) has been prepared (EP581272A). The compound improves the compatibility at a low temperature, but it is not enough. Further, the insertion of a fluorine atom increases the viscosity, which is unfavarable.

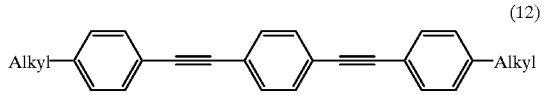
(12)

-continued

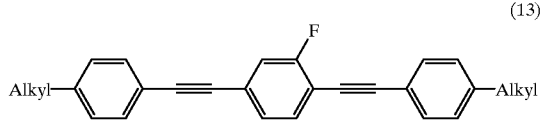
(13)

DISCLOSURE OF THE INVENTION

An object of the present invention is to provide a liquid crystalline compound having higher optical anisotropy than that of known compounds, excellent compatibility with the other many liquid crystalline compounds and high chemical stability.

The other object of the invention is to provide a liquid crystal composition having high $\Delta n$, excellent compatibility, and further low viscosity, high $\Delta\epsilon$ and a broad nematic range. Further object is to provide a practical liquid crystal display device having low threshold voltage.

The present inventors have found that three-cyclic acetylene derivatives having three 1,4-phenylene rings that a 1,4-phenylene ring of the end is substituted by halogen atoms and the rings are bonded by two 1,2-ethynylenes have a specifically high optical anisotropy value and high compatibility with many liquid crystalline compounds at a low temperature.

Namely, the first invention is (1) A liquid crystalline acetylene derivative represented by general formula (1):

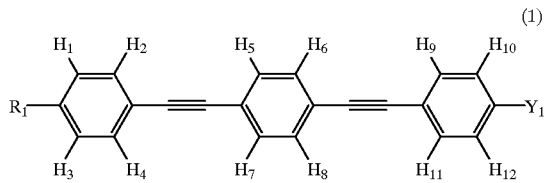
(1)

wherein $H_1$, $H_2$, $H_3$, $H_4$, $H_5$, $H_6$, $H_7$, $H_8$, $H_9$, $H_{10}$, $H_{11}$ and $H_{12}$, each independently, represent a hydrogen atom, a fluorine atom, or a chlorine atom, at least one of $H_1$, $H_2$, $H_3$, $H_4$, $H_9$, $H_{10}$, $H_{11}$ and $H_{12}$ is a fluorine or chlorine atom, $R_1$ represents an alkyl group of 1–20 carbon atoms, in which one or more not-adjacent methylene groups may be replaced by an oxygen atom, a sulfur atom, dihydroxysilylene, dimethylsilylene, —CH=CH— or —C≡C—, any hydrogen atoms of which may be substituted by a halogen atom, and $Y_1$ may be replaced by $R_1$, a fluorine atom, a chlorine atom, a bromine atom, an iodine atom or a cyano group.

The particulars are represented in the following (2) to (5).

(2) A liquid crystalline acetylene derivative according to (1), wherein $R_1$ represents an alkyl group of 1–20 carbon atoms.

(3) A liquid crystalline acetylene derivative according to (2), wherein $H_1$, $H_2$, $H_3$, $H_4$, $H_5$, $H_6$, $H_7$, $H_8$, $H_9$, $H_{10}$, $H_{11}$ and $H_{12}$, each independently, represent a hydrogen atom or a fluorine atom, and at least one of $H_1$, $H_2$, $H_3$, $H_4$, $H_8$, $H_9$, $H_{10}$, $H_{11}$ and $H_{12}$ is a fluorine atom.

(4) A liquid crystalline acetylene derivative according to (3), wherein any one of $H_1$, $H_2$, $H_3$, $H_4$, $H_5$, $H_6$, $H_7$, $H_8$, $H_9$, $H_{10}$, $H_{11}$ and $H_{12}$ is a fluorine atom, and at least one of $H_1$, $H_2$, $H_3$, $H_4$, $H_8$, $H_9$, $H_{10}$, $H_{11}$ and $H_{12}$ is a fluorine atom, and the remains are hydrogen atoms.

(5) A liquid crystalline acetylene derivative according to (3), wherein any two of $H_1$, $H_2$, $H_3$, $H_4$, $H_5$, $H_6$, $H_7$, $H_8$, $H_9$, $H_{10}$, $H_{11}$ and $H_{12}$, represent fluorine atoms, and at least one of $H_1$, $H_2$, $H_3$, $H_4$, $H_8$, $H_9$, $H_{10}$, $H_{11}$ and $H_{12}$ is a fluorine atom, and the remains are hydrogen atoms.

The second invention is (6) A liquid crystal composition comprising at least one liquid crystalline acetylene derivative according to any one of (1) to (5) as a first component, and at least one of compounds as a second or more components.

The particulars are represented in the following (7)–(9).

(7) A liquid crystal composition according to (6) comprising at least one compound selected from the group consisting of compounds represented by general formulas (2), (3) and (4) as a second component,

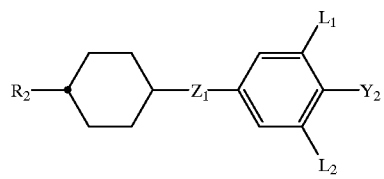

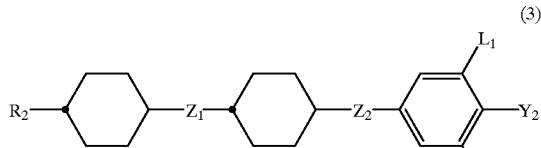

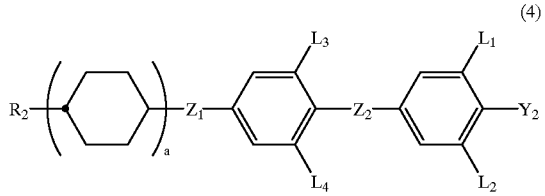

wherein $R_2$ represents an alkyl group of 1–10 carbon atoms; $Y_2$ represents a fluorine atom, a chlorine atom, $OCF_3$, $OCHF_2$, $CF_3$, $CHF_2$ or $CH_2F$; $L_1$, $L_2$, $L_3$ and $L_4$, each independently, represent a hydrogen atom or a fluorine atom; $Z_1$ and $Z_2$, each independently, represent —$CH_2CH_2$—, —CH=CH— or a covalent bond; and a represents 1 or 2.

(8) A liquid crystal composition according to (6) comprising at least one compound selected from the group consisting of compounds represented by general formulas (5), (6), (7), (8) and (9) as a second component:

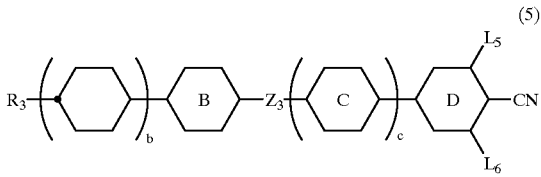

wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cyclohexylene or 1,4-phenylene; $Z_3$ represents —$CH_2CH_2$—, —COO— or a covalent bond; $L_5$ and $L_6$, each independently, represent a hydrogen atom or a fluorine atom; b and c, each independently, represent 0 or 1.

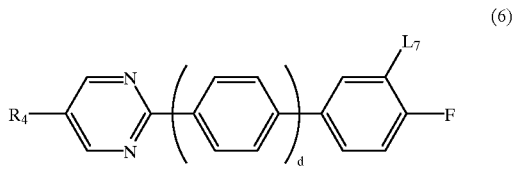

wherein $R_4$ represents an alkyl group of 1–10 carbon atoms; $L_7$ represents a hydrogen atom or a fluorine atom; and d represents 0 or 1.

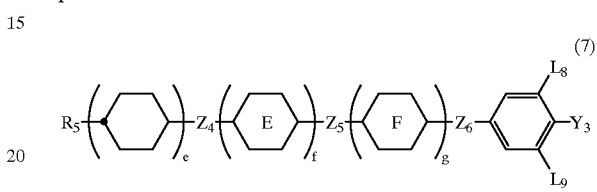

wherein $R_5$ represents an alkyl group of 1–10 carbon atoms; six-membered ring E and six-membered ring F represent, each independently, trans-1,4-cyclohexylene or 1,4-phenylene; $Z_4$ and $Z_5$, each independently, represent —COO— or a covalent bond; $Z_6$ represents —COO— or —C≡C—; $L_8$ and $L_9$, each independently, represent a hydrogen atom or a fluorine atom; $Y_3$ represents a fluorine atom, $OCF_3$, $OCHF_2$, $CF_3$, $CHF_2$ or $CH_2F$; e, f and g, each independently, represent 0 or 1. However, e, f and g are not 0 at the same time; when e is 0, $Z_4$ is a covalent bond; when f or g is 0, $Z_5$ is a covalent bond; and when f and g are 0, $Z_4$ is also a covalent bond.

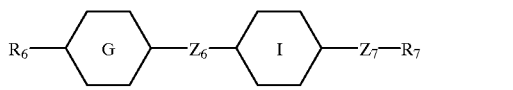

wherein $R_6$ and $R_7$, each independently, represent an alkyl group of 1–10 carbon atoms or an alkenyl group of 2–10 carbon atoms, in which one or more not-adjacent methylene groups may be replaced by an oxygen atom; six-membered ring G represents trans-1,4-cyclohexylene, 1,4-phenylene or pyrimidine-2,5-diyl; six-membered ring I represents trans-1,4-cyclohexylene or 1,4-phenylene; $Z_6$ represents —C≡C—, —COO—, —$CH_2CH_2$—, —CH=CH— C≡C— or a covalent bond; and $Z_7$ represents —COO— or a covalent bond.

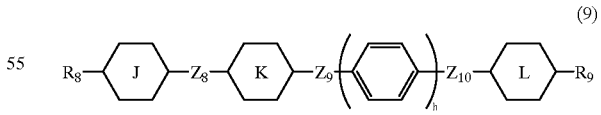

wherein $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring J represents trans-1,4-cyclohexylene, 1,4-phenylene or pyrimidine-2,5-diyl; six-membered ring K represents trans-1,4-cyclohexylene, pyrimidine-2,5-diyl or 1,4-phenylene, and in which one or more hydrogen atoms may be substituted by fluorine atoms at the side, six-membered ring L represents trans-1,4-cyclohexylene or 1,4-phenylene, $Z_8$ and $Z_{10}$, each independently, represent —COO—, —CH$_2$CH$_2$— or a covalent bond, $Z_9$ represents —CH=CH—, —C≡C—, —COO— or a covalent bond, and h represents 0 or 1. However, when h is 0, at least any one of $Z_9$ and $Z_{10}$ are a covalent bond.

(9) A liquid crystal composition according to (6) comprising at least one compound selected from the group consisting of compounds represented by general formulas (2), (3) and (4) as a second component:

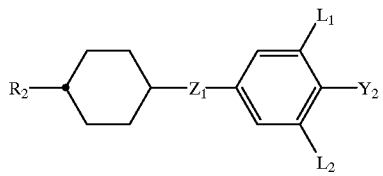

(2)

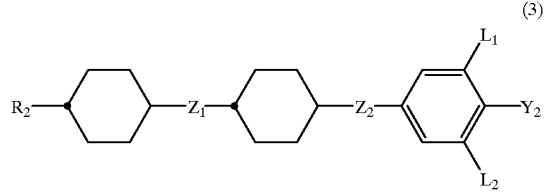

(3)

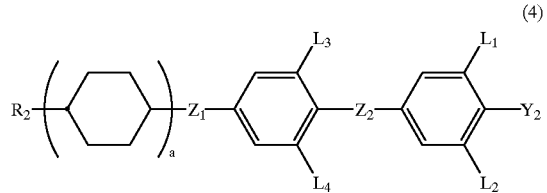

(4)

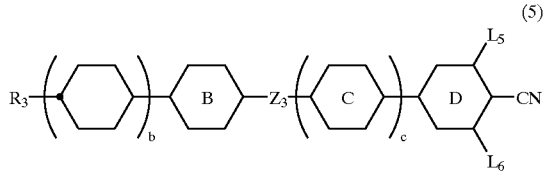

wherein $R_2$ represents an alkyl group of 1–10 carbon atoms; $Y_2$ represents a fluorine atom, a chlorine atom, OCF$_3$, OCHF$_2$, CF$_3$, CHF$_2$ or CH$_2$F; $L_1$, $L_2$, $L_3$ and $L_4$, each independently, represent a hydrogen atom or a fluorine atom; $Z_1$ and $Z_2$, each independently, represent —CH$_2$CH$_2$—, —CH=CH— or a covalent bond; and a represents 1 or 2, at least one compound selected from the group consisting of compounds represented by general formulas (5), (6), (7), (8) and (9) as a third component:

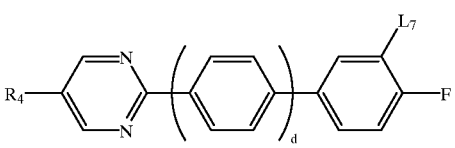

(5)

wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cyclohexylene or 1,4-phenylene; $Z_3$ represents —CH$_2$CH$_2$—, —COO— or a covalent bond; $L_5$ and $L_6$, each independently, represent a hydrogen atom or a fluorine atom; b and c, each independently, represent 0 or 1.

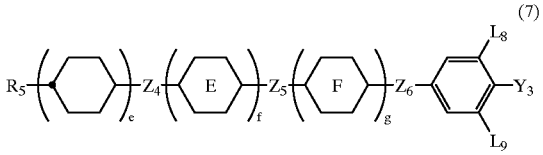

(6)

wherein $R_4$ represents an alkyl group of 1–10 carbon atoms, $L_7$ represents a hydrogen atom or a fluorine atom, and d represents 0 or 1.

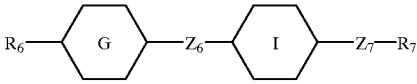

(7)

wherein $R_5$ represents an alkyl group of 1–10 carbon atoms; six-membered ring E and six-membered ring F represent, each independently, trans-1,4-cyclohexylene or 1,4-phenylene; $Z_4$ and $Z_5$, each independently, represent —COO— or a covalent bond; $Z_6$ represents —COO— or —C≡C—; $L_8$ and $L_9$, each independently, represent a hydrogen atom or a fluorine atom; $Y_3$ represents a fluorine atom, OCF$_3$, OCHF$_2$, CF$_3$, CHF$_2$ or CH$_2$F; e, f and g, each independently, represent 0 or 1. However, e, f and g are not 0 at the same time; when e is 0, $Z_4$ is a covalent bond; when f or g is 0, $Z_5$ is a covalent bond; and when f and g are 0, $Z_4$ is also a covalent bond.

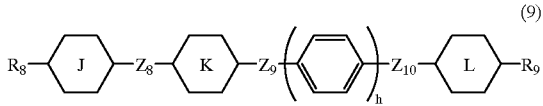

(8)

wherein $R_6$ and $R_7$, each independently, represent an alkyl group of 1–10 carbon atoms or an alkenyl group of 2–10 carbon atoms, in which one or more not-adjacent methylene groups may be replaced by an oxygen atom; six-membered ring G represents trans-1,4-cyclohexylene, 1,4-phenylene or pyrimidine-2,5-diyl; six-membered ring I represents trans-1,4-cyclohexylene or 1,4-phenylene; $Z_6$ represents —C≡C—, —COO—, —CH$_2$CH$_2$—, —CH=CH— C≡C— or a covalent bond; and $Z_7$ represents —COO— or a covalent bond.

(9)

wherein $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring J represents trans-1,4-cyclohexylene, 1,4-phenylene or pyrimidine-2,5-diyl; six-membered ring K represents trans-1,4-cyclohexylene, pyrimidine-2,5-diyl or 1,4-phenylene, in which one or more hydrogen atoms may be substituted by fluorine atoms at the side; six-membered ring L represents trans-1,4-cyclohexylene or 1,4-phenylene; $Z_8$ and $Z_{10}$, each independently, represent —COO—, —CH$_2$CH$_2$— or a covalent bond; $Z_9$ represents —CH═CH—, —C≡C—, —COO— or a covalent bond; and h represents 0 or 1. However, when h is 0, at least any one of $Z_9$ and $Z_{10}$ is a covalent bond.

The third invention is

(10) A liquid crystal display device comprising a liquid crystal composition according to any one of (6) to (9).

In general formula (1) of the compounds of the present invention, $R_1$ represents an alkyl group of 1–20 carbon atoms, in which one or more not-adjacent methylene groups may be replaced by an oxygen atom, a surfer atom, dihydroxysilylene, dimethylsilylene, —CH═CH— or —C≡C—, and further any hydrogen atom in the group may be substituted by a halogen atom. Preferable replaced groups of $R_1$ are an alkyl group, an alkoxy group, an alkoxyalkyl group, an alkenyl group, an alkynyl group, an alkenyloxy group, an alkynyloxy group, a halogen-substituted alkyl group, a halogen-substituted alkoxy group, a halogen-substituted alkoxyalkyl group, a halogen-substituted alkenyl group, a halogen-substituted alkynyl group, a thioalkyl group, a dimethylsilyl group or an alkylsilyl group.

Concrete $R_1$ is preferably a methyl group, an ethyl group, a propyl group, a butyl group, a pentyl group, a hexyl group, a heptyl group, an octyl group, a nonyl group, a decyl group, a methoxy group, an ethoxy group, a propoxy group, a butoxy group, a pentyloxy group, a hexyl oxy group, a heptyloxy group, an octyloxy group, a methoxymethyl group, an ethoxymethyl group, a propoxymethyl group, a butoxymethyl group, a methoxyethyl group, an ethoxyethyl group, a propoxyethyl group, a methoxypropyl group, an ethoxypropyl group, a propoxypropyl group, a vinyl group, a 1-propenyl group, a 1-butenyl group, a 1-pentenyl group, a 3-butenyl group, a 3-pentenyl group, an allyloxy group, an ethynyl group, a 1-propinyl group, a 1-butinyl group, a 1-pentinyl group, a 3-butinyl group, a 3-pentinyl group, a 2-fluoroethyl group, a 3-fluoropropyl group, a 4-fluorobutyl group, a 5-fluoropentyl group, a 3-chloropropyl group, a 2-fluoroethenyl group, 2,2-difluoroethenyl group, a 1,2,2-trifluoroethenyl group, a 3-fluoro-1-butenyl group, a 4-fluoro-1-butenyl group, a 3,3,3-trifluoro-1-propinyl group, a methylthio group, an ethylthio group, a propylthio group, a pentylthio group, an ethyldihydrosilyl group, a propyldihydrosilyl group, a pentyldihydrosilyl group, an ethyldimethyl silyl group, a propyldimethylsilyl group, a pentyldimethylsilyl group, an allyldihydrosilyl group, or an allyldimethylsilyl group.

In general formula (1), substituent groups of benzene rings, $H_1$, $H_2$, $H_3$, $H_4$, $H_5$, $H_6$, $H_7$, $H_8$, $H_9$, $H_{10}$, $H_{11}$ and $H_{12}$, each independently, represent a hydrogen atom, a fluorine atom, or a chlorine atom, at least one of $H_1$, $H_2$, $H_3$, $H_4$, $H_9$, $H_{10}$, $H_{11}$ and $H_{12}$ is a fluorine atom or a chlorine atom, which is characteristic of the present invention.

Further, in the present invention, at least of substituent groups of outer benzene rings of the skeleton structure, $H_1$, $H_2$, $H_3$, $H_4$, $H_9$, $H_{10}$, $H_{11}$ and $H_{12}$, is preferably a fluorine atom.

At least one of these substituent groups of outer benzene rings, $H_1$, $H_2$, $H_3$, $H_4$, $H_9$, $H_{10}$, $H_{11}$ and $H_{12}$, is a fluorine atom or a chlorine atom, preferably 1–4 of these substituent groups are substituted by the fluorine atom or the chlorine atom. Considering the viscosity of the compound of formula (1), one or two substituent groups are preferably substituted by the halogen atoms.

In general formula (1) of the compounds of the present invention, $Y_1$ represents a fluorine atom, a chlorine atom, a bromine atom, an iodine atom, a cyano group, a halogen-substituted alkyl group, a halogen-substituted alkoxy group, a halogen-substituted alkoxyalkyl group, a halogen-substituted alkenyl group or the said $R_1$. Considering the viscosity of the compounds, $Y_1$ is preferably a fluorine atom, a chlorine atom, a cyano group or the said $R_1$.

The compound of formula (1), wherein $R_1$ and $Y_1$ are alkyl groups not replaced by halogens, in which one or more not-adjacent methylene groups may be replaced by an oxygen atom, a sulfur atom, dihydroxysilylene, dimethylsilylene, —CH═CH— or —C≡C—, have negative or very low positive $\Delta\epsilon$.

The compound of formula (1), wherein $R_1$ is an alkyl group not substituted by halogens, in which one or more not-adjacent methylene groups may be replaced by an oxygen atom, a sulfur atom, dihydroxysilylene, dimethylsilylene, —CH═CH— or —C≡C—, and $Y_1$ is a fluorine atom, a chlorine atom, a cyano group or an alkyl group, in which at least one of H of the end methyl group is substituted by a fluorine atom or a chlorine atom, in which one or more not-adjacent methylene groups may be replaced by an oxygen atom, a sulfur atom, dihydroxysilylene, dimethylsilylene, —CH═CH— or —C≡C—, have particularly high positive $\Delta\epsilon$. More concrete substituent group $Y_1$ is preferably a trifluoromethyl group, a difluoromethyl group, a difluorochloromethyl group, 2,2,2-trifluoroethyl group, a trifluoromethoxy group, difluoromethoxy group, a difluorochloromethoxy group, a pentafluoroethoxy group, 1,1,2,2-tetrafluoroethoxy group, a heptafluoropropoxy group, 1,1,2,3,3,3-hexafluoropropoxy group, or a trifluoromethoxymethyl group.

The compound of formula (1), wherein $R_1$ is an alkyl group replaced by halogens, in which one or more not-adjacent methylene groups may be replaced by an oxygen atom, a sulfur atom, dihydroxysilylene, dimethylsilylene, —CH═CH— or —C≡C—, and $Y_1$ is a fluorine atom, a chlorine atom, a cyano group or an alkyl group, in which at least one of H of the end methyl group is substituted by a fluorine atom or a chlorine atom, in which one or more not-adjacent methylene groups may be replaced by an oxygen atom, a sulfur atom, dihydroxysilylene, dimethylsilylene, —CH═CH— or —C≡C—, have often positive $\Delta\epsilon$. The dielectric anisotropy value of the compound having formula (1) is affected by substituent conditions that H atoms of benzene rings having $R_1$ and $Y_1$ are substituted by F or Cl.

The compound of formula (1), wherein $R_1$ is an alkyl group replaced by halogens, in which one or more not-adjacent methylene groups may be replaced by an oxygen atom, a sulfur atom, dihydroxysilylene, dimethylsilylene, —CH═CH— or —C≡C—, and $Y_1$ is an alkyl group not substituted by a halogen atom at the end methyl group, in which at least one or more not-adjacent methylene groups may be replaced by an oxygen atom, a sulfur atom, dihydroxysilylene, dimethylsilylene, —CH═CH— or —C≡C—, have often positive $\Delta\epsilon$. The dielectric anisotropy value of the compound having formula (1) is affected by substituent conditions that H atoms of benzene rings having $R_1$ and $Y_1$ are substituted by F or Cl.

The compounds having constituent atoms replaced by the isotopes have also the same characteristics. Accordingly, the present invention includes the compounds that each constituent atom is replaced by the isotope.

The liquid crystalline acetylene derivative of formula (1) of the present invention has a very high optical anisotropy value, low viscosity, high chemical stability and good compatibility with the other liquid crystal compounds, and it is very useful as a constituent element of a liquid crystal composition.

Particularly, the acetylene derivatives have very high optical anisotropy values in comparison with the other conventional liquid crystalline compounds. As shown examples hereunder, extrapolated Δn is surprisingly a high value, 0.457. The value is the highest in values of known liquid crystalline compounds. Further, in comparison with many known liquid crystalline compounds, it is characteristic of temperature dependency of Δn, and especially the temperature dependency at low temperature region is very low.

The characteristics of the optical anisotropy are similarly shown in acetylene derivatives having a positive Δε value and also a negative Δε value.

The liquid crystalline acetylene derivatives of the present invention have low viscosity. Even if the derivatives are mixed in a liquid crystal composition in quantity, the viscosity of the whole of the liquid crystal composition obtained is not increased so much. The acetylene derivatives have characteristics of very low temperature dependency of the viscosity, particularly, at a low temperature region.

The acetylene derivatives of the present invention have high solubility for the other liquid crystalline compounds or liquid crystal compositions, so that the nematic phase is not damaged by using the acetylene derivatives of formula (1). The liquid crystal compositions mixed with the derivatives represent a nematic phase at a low temperature such as −20° C.

The acetylene derivatives of the present invention is chemically very stable, and the specific resistance of mixed liquid crystal composition is very high. The stability for external factors such as ultraviolet rays and heat is very high and the chemical stability is enough for the use as a component of a practical liquid crystal composition.

As the compounds of the present invention have excellent characteristics as mentioned above, the compounds are suitable not only for the use as liquid crystal materials for STN and also in the other use. As an example, the compounds can be used as liquid crystal compounds for TN, liquid crystal compounds for a guest host-mode, liquid crystal compounds for a liquid crystal display device for a polymer dispersion type, liquid crystal compounds for a dynamic scattering mode, liquid crystal compounds for active matrix, and liquid crystal compounds for SSFLC.

All compounds of the present invention have good characteristics mentioned above. Since the compounds having low viscosity and high Δn are particularly preferable, such compounds have one or two fluorine atom or chlorine atom.

Namely, acetylene derivatives of formula (1), wherein $R_1$ is a straight alkyl group of 1–10 carbon atoms, $H_1$–$H_{11}$ are hydrogen atoms, $H_{12}$ is a fluorine atom, $Y_1$ is a hydrogen atom or a chlorine atom, and acetylene derivatives of formula (1), wherein $R_1$ is a straight alkyl group of 1–10 carbon atoms, $H_1$–$H_9$ and $H_{11}$ are hydrogen atoms, $H_{10}$ and $H_{12}$ are fluorine atoms, and $Y_1$ is a hydrogen atom or a chlorine atom, can be exemplified as particularly preferable compounds having high Δn and high positive Δε.

Moreover, as preferable compounds having high Δn and negative or low positive Δε, the following compounds represented by the formulas can be exemplified.

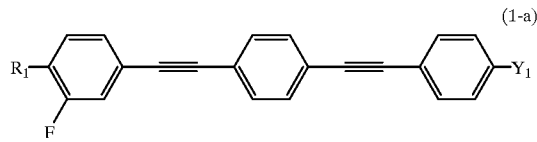

(1-a)

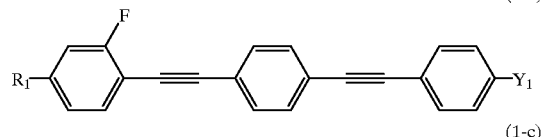

(1-b)

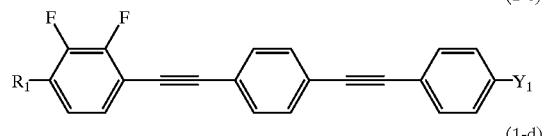

(1-c)

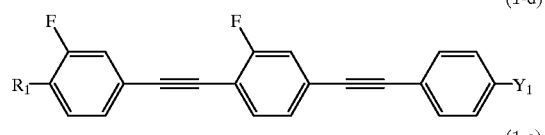

(1-d)

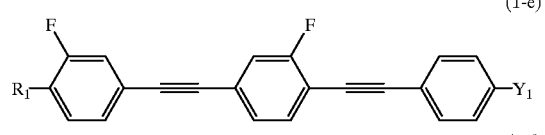

(1-e)

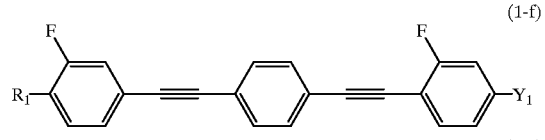

(1-f)

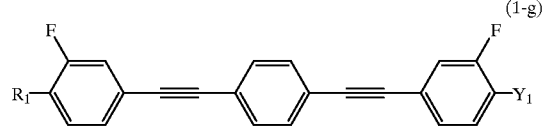

(1-g)

In these formula, $R_1$ and $Y_1$, each independently, represent straight alkyl groups of 1–10 carbon atoms, preferably, straight alkyl groups of 1–5 carbon atoms.

As acetylene derivatives of the present invention, the following compounds can be exemplified.

4-(2-(3-fluoro-4-methylphenyl)ethynyl)-1-(2-(4-methylphenyl)ethynyl)benzene 4-(2-(3-fluoro-4-methylphenyl)ethynyl)-1-(2-(4-ethylphenyl)ethynyl)benzene 4-(2-(3-fluoro-4-methylphenyl)ethynyl)-1-(2-(4-propylphenyl)ethynyl)benzene C-I point: 160.1° C., N-I point: 210.0° C.

4-(2-(3-fluoro-4-methylphenyl)ethynyl)-1-(2-(4-butylphenyl)ethynyl)benzene 4-(2-(3-fluoro-4-methylphenyl)ethynyl)-1-(2-(4-pentylphenyl)ethynyl)benzene 4-(2-(3-fluoro-4-methylphenyl)ethynyl)-1-(2-(4-pentyloxyphenyl)ethynyl)benzene 4-(2-(3-fluoro-4-methylphenyl)ethynyl)-1-(2-(4-hexylphenyl)ethynyl)benzene 4-(2-(3-fluoro-4-methylphenyl)ethynyl)-1-(2-(4-heptylphenyl)ethynyl)benzene 4-(2-(3-fluoro-4-ethylphenyl)ethynyl)-1-(2-(4-methylphenyl)ethynyl)benzene 4-(2-(3-fluoro-4-ethylphenyl)ethynyl)-1-(2-(4-ethylphenyl)ethynyl)benzene 4-(2-(3-fluoro-4-ethylphenyl)ethynyl)-1-(2-(4-propylphenyl)ethynyl)benzene 4-(2-(3-fluoro-4-cyanophenyl)ethynyl)-1-(2-(4-propylphenyl)ethynyl)benzene 4-(2-(3,4-difluorophenyl)ethynyl)-1-(2-(4-propylphenyl)ethynyl)benzene 4-(2-(3-fluoruoromethoxyphenyl)ethynyl)-1-(2-(4-propylphenyl)ethynyl)benzene
4-(2-(3-fluoro-4-ethylphenyl)ethynyl)-1-(2-(4-butylphenyl)ethynyl)benzene
4-(2-(3-fluoro-4-ethylphenyl)ethynyl)-1-(2-(4-pentylphenyl)ethynyl)benzene
4-(2-(3-fluoro-4-ethoxylphenyl)ethynyl)-1-(2-(4-pentylphenyl)ethynyl)benzene
4-(2-(3-fluoro-4-trifluoromethoxyphenyl)ethynyl)-1-(2-(4-pentylphenyl)ethynyl)benzene
4-(2-(3-fluoro-4-ethylphenyl)ethynyl)-1-(2-(4-hexylphenyl)ethynyl)benzene
4-(2-(3-fluoro-4-ethylphenyl)ethynyl)-1-(2-(4-heptylphenyl)ethynyl)benzene
4-(2-(3-fluoro-4-propylphenyl)ethynyl)-1-(2-(4-methylphenyl)ethynyl)benzene
4-(2-(3-fluoro-4-propylphenyl)ethynyl)-1-(2-(4-ethylphenyl)ethynyl)benzene
4-(2-(3-fluoro-4-propylphenyl)ethynyl)-1-(2-(4-propylphenyl)ethynyl)benzene
4-(2-(3-fluoro-4-propylphenyl)ethynyl)-1-(2-(4-propoxyphenyl)ethynyl)benzene
4-(2-(3-fluoro-4-propylphenyl)ethynyl)-1-(2-(4-cyanophenyl)ethynyl)benzene
4-(2-(3-fluoro-4-propylphenyl)ethynyl)-1-(2-(4-fluorophenyl)ethynyl)benzene
4-(2-(3-fluoro-4-propylphenyl)ethynyl)-1-(2-(4-butylphenyl)ethynyl)benzene
4-(2-(3-fluoro-4-propylphenyl)ethynyl)-1-(2-(4-pentylphenyl)ethynyl)benzene
4-(2-(3-fluoro-4-propylphenyl)ethynyl)-1-(2-(4-trifluoromethoxyphenyl)ethynyl)benzene
4-(2-(3-fluoro-4-propylphenyl)ethynyl)-1-(2-(4-difluoromethoxyphenyl)ethynyl)benzene
4-(2-(3-fluoro-4-propylphenyl)ethynyl)-1-(2-(4-hexylphenyl)ethynyl)benzene
4-(2-(3-fluoro-4-propylphenyl)ethynyl)-1-(2-(4-heptylphenyl)ethynyl)benzene
4-(2-(3-fluoro-4-butylphenyl)ethynyl)-1-(2-(4-methylphenyl)ethynyl)benzene
4-(2-(3-fluoro-4-butylphenyl)ethynyl)-1-(2-(4-ethylphenyl)ethynyl)benzene
4-(2-(3-fluoro-4-butylphenyl)ethynyl)-1-(2-(4-propylphenyl)ethynyl)benzene
4-(2-(3-fluoro-4-butylphenyl)ethynyl)-1-(2-(4-butylphenyl)ethynyl)benzene
4-(2-(3-fluoro-4-butylphenyl)ethynyl)-1-(2-(4-pentylphenyl)ethynyl)benzene
4-(2-(3-fluoro-4-butylphenyl)ethynyl)-1-(2-(4-hexylphenyl)ethynyl)benzene
4-(2-(3-fluoro-4-butylphenyl)ethynyl)-1-(2-(4-heptylphenyl)ethynyl)benzene
4-(2-(3-fluoro-4-pentylphenyl)ethynyl)-1-(2-(4-methylphenyl)ethynyl)benzene
4-(2-(3-fluoro-4-pentylphenyl)ethynyl)-1-(2-(4-methoxymethylphenyl)ethynyl)benzene
3-fluoro-4-(2-(3-fluoro-4-pentylphenyl)ethynyl)-1-(2-(4-methoxymethylphenyl)ethynyl)benzene
4-(2-(3-fluoro-4-pentylphenyl)ethynyl)-1-(2-(4-ethylphenyl)ethynyl)benzene
4-(2-(3-fluoro-4-pentylphenyl)ethynyl)-1-(2-(4-propylphenyl)ethynyl)benzene
4-(2-(3-chloro-4-pentylphenyl)ethynyl)-1-(2-(4-propylphenyl)ethynyl)benzene
4-(2-(3-fluoro-4-pentylphenyl)ethynyl)-1-(2-(4-butylphenyl)ethynyl)benzene
4-(2-(3-fluoro-4-pentylphenyl)ethynyl)-1-(2-(4-pentylphenyl)ethynyl)benzene
4-(2-(3-fluoro-4-pentylphenyl)ethynyl)-1-(2-(4-hexylphenyl)ethynyl)benzene
4-(2-(3-fluoro-4-pentylphenyl)ethynyl)-1-(2-(4-heptylphenyl)ethynyl)benzene
4-(2-(3-fluoro-4-hexylphenyl)ethynyl)-1-(2-(4-methylphenyl)ethynyl)benzene
4-(2-(3-fluoro-4-hexylphenyl)ethynyl)-1-(2-(4-ethylphenyl)ethynyl)benzene
4-(2-(3-fluoro-4-hexylphenyl)ethynyl)-1-(2-(4-propylphenyl)ethynyl)benzene
4-(2-(3-fluoro-4-hexylphenyl)ethynyl)-1-(2-(4-butylphenyl)ethynyl)benzene
4-(2-(3-fluoro-4-hexylphenyl)ethynyl)-1-(2-(4-pentylphenyl)ethynyl)benzene
4-(2-(3-fluoro-4-hexylphenyl)ethynyl)-1-(2-(4-hexylphenyl)ethynyl)benzene
4-(2-(3-fluoro-4-hexylphenyl)ethynyl)-1-(2-(4-heptylphenyl)ethynyl)benzene
4-(2-(3-fluoro-4-heptylphenyl)ethynyl)-1-(2-(4-methylphenyl)ethynyl)benzene
4-(2-(3-fluoro-4-heptylphenyl)ethynyl)-1-(2-(4-ethylphenyl)ethynyl)benzene
4-(2-(3-fluoro-4-heptylphenyl)ethynyl)-1-(2-(4-propylphenyl)ethynyl)benzene
4-(2-(3-fluoro-4-heptylphenyl)ethynyl)-1-(2-(4-butylphenyl)ethynyl)benzene
4-(2-(3-fluoro-4-heptylphenyl)ethynyl)-1-(2-(4-pentylphenyl)ethynyl)benzene
4-(2-(3-fluoro-4-heptylphenyl)ethynyl)-1-(2-(4-hexylphenyl)ethynyl)benzene
4-(2-(3-fluoro-4-heptylphenyl)ethynyl)-1-(2-(4-heptylphenyl)ethynyl)benzene
4-(2-(2-fluoro-4-methylphenyl)ethynyl)-1-(2-(4-methylphenyl)ethynyl)benzene
4-(2-(2-fluoro-4-methylphenyl)ethynyl)-1-(2-(4-ethylphenyl)ethynyl)benzene
4-(2-(2-fluoro-4-methylphenyl)ethynyl)-1-(2-(4-propylphenyl)ethynyl)benzene
4-(2-(2-fluoro-4-methoxyphenyl)ethynyl)-1-(2-(4-propylphenyl)ethynyl)benzene
4-(2-(2,3-difluorophenyl)ethynyl)-1-(2-(4-propylphenyl)ethynyl)benzene
4-(2-(2-fluoro-4-methylphenyl)ethynyl)-1-(2-(4-butylphenyl)ethynyl)benzene
4-(2-(2-fluoro-4-methylphenyl)ethynyl)-1-(2-(4-pentylphenyl)ethynyl)benzene
4-(2-(2-fluoro-4-cyanophenyl)ethynyl)-1-(2-(4-pentylphenyl)ethynyl)benzene
4-(2-(2-fluoro-4-trifuluoromethoxyphenyl)ethynyl)-1-(2-(4-pentylphenyl)ethynyl)benzene
4-(2-(2-fluoro-4-methylphenyl)ethynyl)-1-(2-(4-hexylphenyl)ethynyl)benzene
4-(2-(2-fluoro-4-methylphenyl)ethynyl)-1-(2-(4-heptylphenyl)ethynyl)benzene
4-(2-(2-fluoro-4-ethylphenyl)ethynyl)-1-(2-(4-methylphenyl)ethynyl)benzene 4-(2-(2-fluoro-4-ethylphenyl)ethynyl)-1-(2-(4-ethylphenyl)ethynyl)benzene
4-(2-(2-fluoro-4-ethylphenyl)ethynyl)-1-(2-(4-propylphenyl)ethynyl)benzene
4-(2-(2-fluoro-4-ethylphenyl)ethynyl)-1-(2-(4-butylphenyl)ethynyl)benzene
4-(2-(2-fluoro-4-ethylphenyl)ethynyl)-1-(2-(4-pentylphenyl)ethynyl)benzene
4-(2-(2-fluoro-4-ethylphenyl)ethynyl)-1-(2-(4-hexylphenyl)ethynyl)benzene
4-(2-(2-fluoro-4-ethylphenyl)ethynyl)-1-(2-(4-heptylphenyl)ethynyl)benzene
4-(2-(2-fluoro-4-propylphenyl)ethynyl)-1-(2-(4-methylphenyl)ethynyl)benzene
4-(2-(2-fluoro-4-propylphenyl)ethynyl)-1-(2-(4-ethylphenyl)ethynyl)benzene
4-(2-(2-fluoro-4-propylphenyl)ethynyl)-1-(2-(4-propylphenyl)ethynyl)benzene
3-fluoro-4-(2-(2-fluoro-4-propylphenyl)ethynyl)-1-(2-(4-propylphenyl)ethynyl)benzene
4-(2-(2-chloro-4-propylphenyl)ethynyl)-1-(2-(4-propylphenyl)ethynyl)benzene
4-(2-(2-fluoro-4-propylphenyl)ethynyl)-1-(2-(4-butylphenyl)ethynyl)benzene
4-(2-(2-fluoro-4-propylphenyl)ethynyl)-1-(2-(4-pentylphenyl)ethynyl)benzene
4-(2-(2-fluoro-4-propylphenyl)ethynyl)-1-(2-(4-hexylphenyl)ethynyl)benzene
4-(2-(2-fluoro-4-propylphenyl)ethynyl)-1-(2-(4-heptylphenyl)ethynyl)benzene
4-(2-(2-fluoro-4-butylphenyl)ethynyl)-1-(2-(4-methylphenyl)ethynyl)benzene
4-(2-(2-fluoro-4-butylphenyl)ethynyl)-1-(2-(4-ethylphenyl)ethynyl)benzene
4-(2-(2-fluoro-4-butylphenyl)ethynyl)-1-(2-(4-propylphenyl)ethynyl)benzene
4-(2-(2-fluoro-4-butylphenyl)ethynyl)-1-(2-(4-butylphenyl)ethynyl)benzene
4-(2-(2-fluoro-4-butylphenyl)ethynyl)-1-(2-(4-pentylphenyl)ethynyl)benzene
4-(2-(2-fluoro-4-butylphenyl)ethynyl)-1-(2-(4-hexylphenyl)ethynyl)benzene
4-(2-(2-fluoro-4-butylphenyl)ethynyl)-1-(2-(4-heptylphenyl)ethynyl)benzene
4-(2-(2-fluoro-4-pentylphenyl)ethynyl)-1-(2-(4-methylphenyl)ethynyl)benzene
4-(2-(2-fluoro-4-pentylphenyl)ethynyl)-1-(2-(4-fluorophenyl)ethynyl)benzene
4-(2-(2-fluoro-4-pentylphenyl)ethynyl)-1-(2-(4-chlorophenyl)ethynyl)benzene
4-(2-(2-fluoro-4-pentylphenyl)ethynyl)-1-(2-(4-trifluoromethoxyphenyl)ethynyl)benzene
4-(2-(2-fluoro-4-pentylphenyl)ethynyl)-1-(2-(4-difluoromethoxyphenyl)ethynyl)benzene
4-(2-(2-fluoro-4-pentylphenyl)ethynyl)-1-(2-(4-ethylphenyl)ethynyl)benzene
4-(2-(2-fluoro-4-pentylphenyl)ethynyl)-1-(2-(4-propylphenyl)ethynyl)benzene
4-(2-(2,6-difluoro-4-pentylphenyl)ethynyl)-1-(2-(4-propylphenyl)ethynyl)benzene
4-(2-(2-fluoro-4-pentylphenyl)ethynyl)-1-(2-(4-butylphenyl)ethynyl)benzene
4-(2-(2-fluoro-4-pentylphenyl)ethynyl)-1-(2-(4-pentylphenyl)ethynyl)benzene
4-(2-(2-fluoro-4-pentylphenyl)ethynyl)-1-(2-(4-hexylphenyl)ethynyl)benzene
4-(2-(2-fluoro-4-pentylphenyl)ethynyl)-1-(2-(4-heptylphenyl)ethynyl)benzene
4-(2-(2-fluoro-4-hexylphenyl)ethynyl)-1-(2-(4-methylphenyl)ethynyl)benzene
4-(2-(2-fluoro-4-hexylphenyl)ethynyl)-1-(2-(4-ethylphenyl)ethynyl)benzene
4-(2-(2-fluoro-4-hexylphenyl)ethynyl)-1-(2-(4-propylphenyl)ethynyl)benzene
4-(2-(2-fluoro-4-hexylphenyl)ethynyl)-1-(2-(4-butylphenyl)ethynyl)benzene
4-(2-(2-fluoro-4-hexylphenyl)ethynyl)-1-(2-(4-pentylphenyl)ethynyl)benzene
4-(2-(2-fluoro-4-hexylphenyl)ethynyl)-1-(2-(4-hexylphenyl)ethynyl)benzene
4-(2-(2-fluoro-4-hexylphenyl)ethynyl)-1-(2-(4-heptylphenyl)ethynyl)benzene
4-(2-(2-fluoro-4-heptylphenyl)ethynyl)-1-(2-(4-methylphenyl)ethynyl)benzene
4-(2-(2-fluoro-4-heptylphenyl)ethynyl)-1-(2-(4-ethylphenyl)ethynyl)benzene
4-(2-(2-fluoro-4-heptylphenyl)ethynyl)-1-(2-(4-propylphenyl)ethynyl)benzene
4-(2-(2-fluoro-4-heptylphenyl)ethynyl)-1-(2-(4-butylphenyl)ethynyl)benzene
4-(2-(2-fluoro-4-heptylphenyl)ethynyl)-1-(2-(4-pentylphenyl)ethynyl)benzene
4-(2-(2-fluoro-4-heptylphenyl)ethynyl)-1-(2-(4-hexylphenyl)ethynyl)benzene
4-(2-(2-fluoro-4-heptylphenyl)ethynyl)-1-(2-(4-heptylphenyl)ethynyl)benzene
4-(2-(2,3-difluoro-4-methylphenyl)ethynyl)-1-(2-(4-methylphenyl)ethynyl)benzene
4-(2-(2,3-difluoro-4-methylphenyl)ethynyl)-1-(2-(4-ethylphenyl)ethynyl)benzene
4-(2-(2,3-difluoro-4-methylphenyl)ethynyl)-1-(2-(4-propylphenyl)ethynyl)benzene
4-(2-(2,3-difluoro-4-methoxyphenyl)ethynyl)-1-(2-(4-propylphenyl)ethynyl)benzene
4-(2-(2,3-difluoro-4-trifluoromethoxyphenyl)ethynyl)-1-(2-(4-propylphenyl)ethynyl)benzene
4-(2-(2,3-difluoro-4-difluoromethoxyphenyl)ethynyl)-1-(2-(4-propylphenyl)ethynyl)benzene
4-(2-(2,3,4-trifluoro-4-methylphenyl)ethynyl)-1-(2-(4-propylphenyl)ethynyl)benzene
4-(2-(2,3-difluoro-4-methylphenyl)ethynyl)-1-(2-(4-butylphenyl)ethynyl)benzene
4-(2-(2,3-difluoro-4-methylphenyl)ethynyl)-1-(2-(4-pentylphenyl)ethynyl)benzene
4-(2-(2,3-difluoro-4-methylphenyl)ethynyl)-1-(2-(4-hexylphenyl)ethynyl)benzene
4-(2-(2,3-difluoro-4-methylphenyl)ethynyl)-1-(2-(4-heptylphenyl)ethynyl)benzene
4-(2-(2,3-difluoro-4-ethylphenyl)ethynyl)-1-(2-(4-methylphenyl)ethynyl)benzene
4-(2-(2,3-difluoro-4-ethylphenyl)ethynyl)-1-(2-(4-ethylphenyl)ethynyl)benzene
4-(2-(2,3-difluoro-4-ethylphenyl)ethynyl)-1-(2-(4-propylphenyl)ethynyl)benzene 4-(2-(2,3-difluoro-4-ethylphenyl)ethynyl)-1-(2-(4-butylphenyl)ethynyl)benzene
4-(2-(2,3-difluoro-4-ethylphenyl)ethynyl)-1-(2-(4-pentylphenyl)ethynyl)benzene
4-(2-(2,3-difluoro-4-ethylphenyl)ethynyl)-1-(2-(4-hexylphenyl)ethynyl)benzene
4-(2-(2,3-difluoro-4-ethylphenyl)ethynyl)-1-(2-(4-heptylphenyl)ethynyl)benzene
4-(2-(2,3-difluoro-4-propylphenyl)ethynyl)-1-(2-(4-methylphenyl)ethynyl)benzene
4-(2-(2,3-difluoro-4-propylphenyl)ethynyl)-1-(2-(4-methoxymethylphenyl)ethynyl)benzene
4-(2-(2,3-difluoro-4-propylphenyl)ethynyl)-1-(2-(4-chlorophenyl)ethynyl)benzene
4-(2-(2,3-difluoro-4-propylphenyl)ethynyl)-1-(2-(4-fluorophenyl)ethynyl)benzene
4-(2-(2,3-difluoro-4-propylphenyl)ethynyl)-1-(2-(4-trifluoromethoxylphenyl)ethynyl)benzene
4-(2-(2,3-difluoro-4-propylphenyl)ethynyl)-1-(2-(4-ethylphenyl)ethynyl)benzene
4-(2-(2,3-difluoro-4-propylphenyl)ethynyl)-1-(2-(4-propylphenyl)ethynyl)benzene
4-(2-(2,3,5,6-tetrafluoro-4-propylphenyl)ethynyl)-1-(2-(4-propylphenyl)ethynyl)benzene
4-(2-(2,3-difluoro-4-propylphenyl)ethynyl)-1-(2-(2-fluoro-4-propylphenyl)ethynyl)benzene
4-(2-(2,3-difluoro-4-propylphenyl)ethynyl)-1-(2-(4-butylphenyl)ethynyl)benzene
4-(2-(2,3-difluoro-4-propylphenyl)ethynyl)-1-(2-(4-pentylphenyl)ethynyl)benzene
4-(2-(2,3-difluoro-4-propylphenyl)ethynyl)-1-(2-(4-pentylphenyl)ethynyl)benzene
4-(2-(2,3-difluoro-4-propoxylphenyl)ethynyl)-1-(2-(4-pentylphenyl)ethynyl)benzene
4-(2-(2,3-difluoro-4-propylphenyl)ethynyl)-1-(2-(4-hexylphenyl)ethynyl)benzene
4-(2-(2,3-difluoro-4-propylphenyl)ethynyl)-1-(2-(4-heptylphenyl)ethynyl)benzene
4-(2-(2,3-difluoro-4-butylphenyl)ethynyl)-1-(2-(4-methylphenyl)ethynyl)benzene
4-(2-(2,3-difluoro-4-butylphenyl)ethynyl)-1-(2-(4-ethylphenyl)ethynyl)benzene
4-(2-(2,3-difluoro-4-butylphenyl)ethynyl)-1-(2-(4-propylphenyl)ethynyl)benzene
4-(2-(2,3-difluoro-4-butylphenyl)ethynyl)-1-(2-(4-butylphenyl)ethynyl)benzene
4-(2-(2,3-difluoro-4-butylphenyl)ethynyl)-1-(2-(4-pentylphenyl)ethynyl)benzene
4-(2-(2,3-difluoro-4-butylphenyl)ethynyl)-1-(2-(4-hexylphenyl)ethynyl)benzene
4-(2-(2,3-difluoro-4-butylphenyl)ethynyl)-1-(2-(4-heptylphenyl)ethynyl)benzene
4-(2-(2,3-difluoro-4-pentylphenyl)ethynyl)-1-(2-(4-methylphenyl)ethynyl)benzene
4-(2-(2,3-difluoro-4-pentylphenyl)ethynyl)-1-(2-(4-ethylphenyl)ethynyl)benzene
4-(2-(2,3-difluoro-4-pentylphenyl)ethynyl)-1-(2-(4-propylphenyl)ethynyl)benzene
4-(2-(2,3-difluoro-4-pentylphenyl)ethynyl)-1-(2-(4-butylphenyl)ethynyl)benzene
4-(2-(2,3-difluoro-4-pentylphenyl)ethynyl)-1-(2-(4-pentylphenyl)ethynyl)benzene
4-(2-(2,3-difluoro-4-pentylphenyl)ethynyl)-1-(2-(4-hexylphenyl)ethynyl)benzene
4-(2-(2,3-difluoro-4-pentylphenyl)ethynyl)-1-(2-(4-heptylphenyl)ethynyl)benzene
4-(2-(2,3-difluoro-4-hexylphenyl)ethynyl)-1-(2-(4-methylphenyl)ethynyl)benzene
4-(2-(2,3-difluoro-4-hexylphenyl)ethynyl)-1-(2-(4-ethylphenyl)ethynyl)benzene
4-(2-(2,3-difluoro-4-hexylphenyl)ethynyl)-1-(2-(4-propylphenyl)ethynyl)benzene
4-(2-(2,3-difiluoro-4-hexylphenyl)ethynyl)-1-(2-(4-butylphenyl)ethynyl)benzene
4-(2-(2,3-difluoro-4-hexylphenyl)ethynyl)-1-(2-(4-pentylphenyl)ethynyl)benzene
4-(2-(2,3-difluoro-4-hexylphenyl)ethynyl)-1-(2-(4-hexylphenyl)ethynyl)benzene
4-(2-(2,3-difluoro-4-hexylphenyl)ethynyl)-1-(2-(4-heptylphenyl)ethynyl)benzene
4-(2-(2,3-difluoro-4-heptylphenyl)ethynyl)-1-(2-(4-methylphenyl)ethynyl)benzene
4-(2-(2,3-difluoro-4-heptylphenyl)ethynyl)-1-(2-(4-ethylphenyl)ethynyl)benzene
4-(2-(2,3-difluoro-4-heptylphenyl)ethynyl)-1-(2-(4-propylphenyl)ethynyl)benzene
4-(2-(2,3-difluoro-4-heptylphenyl)ethynyl)-1-(2-(4-butylphenyl)ethynyl)benzene
4-(2-(2,3-difluoro-4-heptylphenyl)ethynyl)-1-(2-(4-heptylphenyl)ethynyl)benzene
4-(2-(2,3-difluoro-4-heptylphenyl)ethynyl)-1-(2-(4-hexylphenyl)ethynyl)benzene
4-(2-(2,3-difluoro-4-heptylphenyl)ethynyl)-1-(2-(4-beptylphenyl)ethynyl)benzene
3-fluoro-4-(2-(3-fluoro-4-methylphenyl)ethynyl)-1-(2-(4-methylphenyl)ethynyl)benzene
3-fluoro-4-(2-(3-fluoro-4-methylphenyl)ethynyl)-1-(2-(4-metoxymethylphenyl)ethynyl)benzene
3-fluoro-4-(2-(3-fluoro-4-methylphenyl)ethynyl)-1-(2-(4-ethylphenyl)ethynyl)benzene
3-fluoro-4-(2-(3-fluoro-4-methylphenyl)ethynyl)-1-(2-(4-propylphenyl)ethynyl)benzene
3-fluoro-4-(2-(3-fluoro-4-methoxymethylphenyl)ethynyl)-1-(2-(4-propylphenyl)ethynyl)benzene
3-fluoro-4-(2-(3-fluoro-4-trifluoromethylphenyl)ethynyl)-1-(2-(4-propylphenyl)ethynyl)benzene
3-fluoro-4-(2-(3-fluoro-4-trifluoromethoxyphenyl)ethynyl)-1-(2-(4-propylphenyl)ethynyl)benzene
3-fluoro-4-(2-(3-fluoro-4-difluoromethoxyphenyl)ethynyl)-1-(2-(4-propylphenyl)ethynyl)benzene
3-fluoro-4-(2-(3-fluoro-4-chlorophenyl)ethynyl)-1-(2-(4-propylphenyl)ethynyl)benzene
3-fluoro-4-(2-(3-fluoro-4-methylphenyl)ethynyl)-1-(2-(4-butylphenyl)ethynyl)benzene
3-fluoro-4-(2-(3-fluoro-4-methylphenyl)ethynyl)-1-(2-(4-pentylphenyl)ethynyl)benzene
3-fluoro-4-(2-(3-fluoro-4-methylphenyl)ethynyl)-1-(2-(4-hexylphenyl)ethynyl)benzene
3-fluoro-4-(2-(3-fluoro-4-methylphenyl)ethynyl)-1-(2-(4-heptylphenyl)ethynyl)benzene
3-fluoro-4-(2-(3-fluoro-4-ethylphenyl)ethynyl)-1-(2-(4-methylphenyl)ethynyl)benzene
3-fluoro-4-(2-(3-fluoro-4-ethylphenyl)ethynyl)-1-(2-(4-ethylphenyl)ethynyl)benzene 3-fluoro-4-(2-(3-fluoro-4-ethylphenyl)ethynyl)-1-(2-(4-propylphenyl)ethynyl)benzene
3-fluoro-4-(2-(3-fluoro-4-ethylphenyl)ethynyl)-1-(2-(4-butylphenyl)ethynyl)benzene
3-fluoro-4-(2-(3-fluoro-4-ethylphenyl)ethynyl)-1-(2-(4-pentylphenyl)ethynyl)benzene
3-fluoro-4-(2-(3-fluoro-4-ethylphenyl)ethynyl)-1-(2-(4-hexylphenyl)ethynyl)benzene
3-fluoro-4-(2-(3-fluoro-4-ethylphenyl)ethynyl)-1-(2-(4-heptylphenyl)ethynyl)benzene
3-fluoro-4-(2-(3-fluoro-4-propylphenyl)ethynyl)-1-(2-(4-methylphenyl)ethynyl)benzene
3-fluoro-4-(2-(3-fluoro-4-propylphenyl)ethynyl)-1-(2-(4-ethylphenyl)ethynyl)benzene
3-fluoro-4-(2-(3-fluoro-4-propylphenyl)ethynyl)-1-(2-(4-propylphenyl)ethynyl)benzene
2,3-difluoro-4-(2-(3-fluoro-4-propylphenyl)ethynyl)-1-(2-(4-propylphenyl)ethynyl)benzene
3,5-difluoro-4-(2-(3-fluoro-4-propylphenyl)ethynyl)-1-(2-(4-propylphenyl)ethynyl)benzene
2,3-difluoro-4-(2-(3-fluoro-4-propylphenyl)ethynyl)-1-(2-(4-propylphenyl)ethynyl)benzene
3-fluoro-4-(2-(3-fluoro-4-propylphenyl)ethynyl)-1-(2-(3-fluoro-4-propylphenyl)ethynyl)benzene
3-fluoro-4-(2-(3-fluoro-4-trifluoromethoxyphenyl)ethynyl)-1-(2-(4-propylphenyl)ethynyl)benzene
3-fluoro-4-(2-(3-fluoro-4-propylphenyl)ethynyl)-1-(2-(4-butylphenyl)ethynyl)benzene
3-fluoro-4-(2-(3-fluoro-4-propylphenyl)ethynyl)-1-(2-(4-pentylphenyl)ethynyl)benzene
3-fluoro-4-(2-(3-fluoro-4-propylphenyl)ethynyl)-1-(2-(4-hexylphenyl)ethynyl)benzene
3-fluoro-4-(2-(3-fluoro-4-propylphenyl)ethynyl)-1-(2-(4-heptylphenyl)ethynyl)benzene
3-fluoro-4-(2-(3-fluoro-4-butylphenyl)ethynyl)-1-(2-(4-methylphenyl)ethynyl)benzene
3-fluoro-4-(2-(3-fluoro-4-butylphenyl)ethynyl)-1-(2-(4-ethylphenyl)ethynyl)benzene
3-fluoro-4-(2-(3-fluoro-4-butylphenyl)ethynyl)-1-(2-(4-propylphenyl)ethynyl)benzene
3-fluoro-4-(2-(3-fluoro-4-butylphenyl)ethynyl)-1-(2-(4-butylphenyl)ethynyl)benzene
3-fluoro-4-(2-(3-fluoro-4-butylphenyl)ethynyl)-1-(2-(4-pentylphenyl)ethynyl)benzene
3-fluoro-4-(2-(3-fluoro-4-butoxyphenyl)ethynyl)-1-(2-(4-pentylphenyl)ethynyl)benzene
3-fluoro-4-(2-(3-fluoro-4-butylphenyl)ethynyl)-1-(2-(4-hexylphenyl)ethynyl)benzene
3-fluoro-4-(2-(3-fluoro-4-butylphenyl)ethynyl)-1-(2-(4-heptylphenyl)ethynyl)benzene
3-fluoro-4-(2-(3-fluoro-4-pentylphenyl)ethynyl)-1-(2-(4-methylphenyl)ethynyl)benzene
3-fluoro-4-(2-(3-fluoro-4-pentylphenyl)ethynyl)-1-(2-(4-ethylphenyl)ethynyl)benzene
3-fluoro-4-(2-(3-fluoro-4-pentylphenyl)ethynyl)-1-(2-(4-ethenylphenyl)ethynyl)benzene
3-fluoro-4-(2-(3-fluoro-4-pentylphenyl)ethynyl)-1-(2-(4-(3-butenyl)phenyl)ethynyl)benzene
3-fluoro-4-(2-(3-fluoro-4-pentylphenyl)ethynyl)-1-(2-(4-propylphenyl)ethynyl)benzene
3-fluoro-4-(2-(3-fluoro-4-pentylphenyl)ethynyl)-1-(2-(4-butylphenyl)ethynyl)benzene
3-fluoro-4-(2-(3-fluoro-4-pentylphenyl)ethynyl)-1-(2-(4-pentylphenyl)ethynyl)benzene
3-fluoro-4-(2-(3-fluoro-4-pentylphenyl)ethynyl)-1-(2-(4-hexylphenyl)ethynyl)benzene
3-fluoro-4-(2-(3-fluoro-4-pentylphenyl)ethynyl)-1-(2-(4-heptylphenyl)ethynyl)benzene
3-fluoro-4-(2-(3-fluoro-4-hexylphenyl)ethynyl)-1-(2-(4-methylphenyl)ethynyl)benzene
3-fluoro-4-(2-(3-fluoro-4-hexylphenyl)ethynyl)-1-(2-(4-ethylphenyl)ethynyl)benzene
3-fluoro-4-(2-(3-fluoro-4-hexylphenyl)ethynyl)-1-(2-(4-propylphenyl)ethynyl)benzene
3-fluoro-4-(2-(3-fluoro-4-hexylphenyl)ethynyl)-1-(2-(4-butylphenyl)ethynyl)benzene
3-fluoro-4-(2-(3-fluoro-4-hexylphenyl)ethynyl)-1-(2-(4-pentylphenyl)ethynyl)benzene
3-fluoro-4-(2-(3-fluoro-4-hexylphenyl)ethynyl)-1-(2-(4-hexylphenyl)ethynyl)benzene
3-fluoro-4-(2-(3-fluoro-4-hexylphenyl)ethynyl)-1-(2-(4-heptylphenyl)ethynyl)benzene
3-fluoro-4-(2-(3-fluoro-4-heptylphenyl)ethynyl)-1-(2-(4-methylphenyl)ethynyl)benzene
3-fluoro-4-(2-(3-fluoro-4-heptylphenyl)ethynyl)-1-(2-(4-ethylphenyl)ethynyl)benzene
3-fluoro-4-(2-(3-fluoro-4-heptylphenyl)ethynyl)-1-(2-(4-propylphenyl)ethynyl)benzene
3-fluoro-4-(2-(3-fluoro-4-heptylphenyl)ethynyl)-1-(2-(4-butylphenyl)ethynyl)benzene
3-fluoro-4-(2-(3-fluoro-4-heptylphenyl)ethynyl)-1-(2-(4-pentylphenyl)ethynyl)benzene
3-fluoro-4-(2-(3-fluoro-4-heptylphenyl)ethynyl)-1-(2-(4-hexylphenyl)ethynyl)benzene
3-fluoro-4-(2-(3-fluoro-4-heptylphenyl)ethynyl)-1-(2-(4-heptylphenyl)ethynyl)benzene
2-fluoro-4-(2-(3-fluoro-4-methylphenyl)ethynyl)-1-(2-(4-methylphenyl)ethynyl)benzene
2-fluoro-4-(2-(3-fluoro-4-methylphenyl)ethynyl)-1-(2-(4-ethylphenyl)ethynyl)benzene
2-fluoro-4-(2-(3-fluoro-4-methylphenyl)ethynyl)-1-(2-(4-propylphenyl)ethynyl)benzene
C-N point: 156.4° C., N-I point: 187.1° C.
2-fluoro-4-(2-(3-fluoro-4-methylphenyl)ethynyl)-1-(2-(4-butylphenyl)ethynyl)benzene
2-fluoro-4-(2-(3-fluoro-4-methylphenyl)ethynyl)-1-(2-(4-pentylphenyl)ethynyl)benzene
2-fluoro-4-(2-(3-fluoro-4-methylphenyl)ethynyl)-1-(2-(4-hexylphenyl)ethynyl)benzene
2-fluoro-4-(2-(3-fluoro-4-methylphenyl)ethynyl)-1-(2-(4-heptylphenyl)ethynyl)benzene
2-fluoro-4-(2-(3-fluoro-4-ethylphenyl)ethynyl)-1-(2-(4-methylphenyl)ethynyl)benzene
2-fluoro-4-(2-(3-fluoro-4-ethylphenyl)ethynyl)-1-(2-(4-ethylphenyl)ethynyl)benzene
2-fluoro-4-(2-(3-fluoro-4-ethylphenyl)ethynyl)-1-(2-(4-propylphenyl)ethynyl)benzene
2-fluoro-4-(2-(3-fluoro-4-ethylphenyl)ethynyl)-1-(2-(4-butylphenyl)ethynyl)benzene
2-fluoro-4-(2-(3-fluoro-4-ethylphenyl)ethynyl)-1-(2-(4-pentylphenyl)ethynyl)benzene
2-fluoro-4-(2-(3-fluoro-4-ethylphenyl)ethynyl)-1-(2-(4-exylphenyl)ethynyl)benzene
2-fluoro-4-(2-(3-fluoro-4-ethylphenyl)ethynyl)-1-(2-(4-heptylphenyl)ethynyl)benzene 2,3-difluoro-4-(2-(3-fluoro-4-propylphenyl)ethynyl)-1-(2-(4-methylphenyl)ethynyl)benzene
2-fluoro-4-(2-(3-fluoro-4-propylphenyl)ethynyl)-1-(2-(4-ethylphenyl)ethynyl)benzene
2-fluoro-4-(2-(3-fluoro-4-propylphenyl)ethynyl)-1-(2-(4-propylphenyl)ethynyl)benzene
2-fluoro-4-(2-(3-fluoro-4-propylphenyl)ethynyl)-1-(2-(4-butylphenyl)ethynyl)benzene
2-fluoro-4-(2-(3-fluoro-4-propylphenyl)ethynyl)-1-(2-(4-pentylphenyl)ethynyl)benzene
2,6-difluoro-4-(2-(3-fluoro-4-propylphenyl)ethynyl)-1-(2-(4-pentylphenyl)ethynyl)benzene
2-fluoro-4-(2-(3-fluoro-4-propylphenyl)ethynyl)-1-(2-(4-hexylphenyl)ethynyl)benzene
2-fluoro-4-(2-(3-fluoro-4-propylphenyl)ethynyl)-1-(2-(4-heptylphenyl)ethynyl)benzene
2-fluoro-4-(2-(3-fluoro-4-butylphenyl)ethynyl)-1-(2-(4-methylphenyl)ethynyl)benzene
2-fluoro-4-(2-(3-fluoro-4-butylphenyl)ethynyl)-1-(2-(4-ethylphenyl)ethynyl)benzene
2-fluoro-4-(2-(3-fluoro-4-butylphenyl)ethynyl)-1-(2-(4-propylphenyl)ethynyl)benzene
2-fluoro-4-(2-(3-fluoro-4-butylphenyl)ethynyl)-1-(2-(4-butylphenyl)ethynyl)benzene
2-fluoro-4-(2-(3-fluoro-4-butylphenyl)ethynyl)-1-(2-(4-pentylphenyl)ethynyl)benzene
2-fluoro-4-(2-(3-fluoro-4-butylphenyl)ethynyl)-1-(2-(4-exylphenyl)ethynyl)benzene
2-fluoro-4-(2-(3-fluoro-4-butylphenyl)ethynyl)-1-(2-(4-heptylphenyl)ethynyl)benzene
2-fluoro-4-(2-(3-fluoro-4-pentylphenyl)ethynyl)-1-(2-(4-methylphenyl)ethynyl)benzene
2-fluoro-4-(2-(3-fluoro-4-pentylphenyl)ethynyl)-1-(2-(4-ethylphenyl)ethynyl)benzene
2-fluoro-4-(2-(3-fluoro-4-pentylphenyl)ethynyl)-1-(2-(4-propylphenyl)ethynyl)benzene
2-fluoro-4-(2-(3-fluoro-4-pentylphenyl)ethynyl)-1-(2-(4-butylphenyl)ethynyl)benzene
2-fluoro-4-(2-(3-fluoro-4-pentylphenyl)ethynyl)-1-(2-(4-pentylphenyl)ethynyl)benzene
2-fluoro-4-(2-(3-fluoro-4-pentylphenyl)ethynyl)-1-(2-(4-hexylphenyl)ethynyl)benzene
2-fluoro-4-(2-(3-fluoro-4-pentylphenyl)ethynyl)-1-(2-(4-heptylphenyl)ethynyl)benzene
2-fluoro-4-(2-(3-fluoro-4-hexylphenyl)ethynyl)-1-(2-(4-methylphenyl)ethynyl)benzene
2-fluoro-4-(2-(3-fluoro-4-hexylphenyl)ethynyl)-1-(2-(4-ethylphenyl)ethynyl)benzene
2-fluoro-4-(2-(3-fluoro-4-hexylphenyl)ethynyl)-1-(2-(4-propylphenyl)ethynyl)benzene
2-fluoro-4-(2-(3-fluoro-4-hexylphenyl)ethynyl)-1-(2-(4-butylphenyl)ethynyl)benzene
2-fluoro-4-(2-(3-fluoro-4-hexylphenyl)ethynyl)-1-(2-(4-pentylphenyl)ethynyl)benzene
2-fluoro-4-(2-(3-fluoro-4-hexylphenyl)ethynyl)-1-(2-(4-exylphenyl)ethynyl)benzene
2-fluoro-4-(2-(3-fluoro-4-hexylphenyl)ethynyl)-1-(2-(4-eptylphenyl)ethynyl)benzene
2-fluoro-4-(2-(3-fluoro-4-heptylphenyl)ethynyl)-1-(2-(4-ethylphenyl)ethynyl)benzene
2-fluoro-4-(2-(3-fluoro-4-heptylphenyl)ethynyl)-1-(2-(4-thylphenyl)ethynyl)benzene
2-fluoro-4-(2-(3-fluoro-4-heptylphenyl)ethynyl)-1-(2-(4-propylphenyl)ethynyl)benzene
2-fluoro-4-(2-(3-fluoro-4-heptylphenyl)ethynyl)-1-(2-(4-butylphenyl)ethynyl)benzene
2-fluoro-4-(2-(3-fluoro-4-heptylphenyl)ethynyl)-1-(2-(4-pentylphenyl)ethynyl)benzene
2-fluoro-4-(2-(3-fluoro-4-heptylphenyl)ethynyl)-1-(2-(4-hexylphenyl)ethynyl)benzene
2-fluoro-4-(2-(3-fluoro-4-heptylphenyl)ethynyl)-1-(2-(4-heptylphenyl)ethynyl)benzene
4-(2-(3-fluoro-4-methylphenyl)ethynyl)-1-(2-(2-fluoro-4-methylphenyl)ethynyl)benzene
4-(2-(3-fluoro-4-methylphenyl)ethynyl)-1-(2-(2-fluoro-4-ethylphenyl)ethynyl)benzene
4-(2-(3-fluoro-4-methylphenyl)ethynyl)-1-(2-(2-fluoro-4-propylphenyl)ethynyl)benzene
4-(2-(3-fluoro-4-methylphenyl)ethynyl)-1-(2-(2-fluoro-4-butylphenyl)ethynyl)benzene
4-(2-(3-fluoro-4-methylphenyl)ethynyl)-1-(2-(2-fluoro-4-pentylphenyl)ethynyl)benzene
4-(2-(3-fluoro-4-methylphenyl)ethynyl)-1-(2-(2-fluoro-4-exylphenyl)ethynyl)benzene
4-(2-(3-fluoro-4-methylphenyl)ethynyl)-1-(2-(2-fluoro-4-heptylphenyl)ethynyl)benzene
4-(2-(3-fluoro-4-ethylphenyl)ethynyl)-1-(2-(2-fluoro-4-methylphenyl)ethynyl)benzene
4-(2-(3-fluoro-4-ethylphenyl)ethynyl)-1-(2-(2-fluoro-4-ethylphenyl)ethynyl)benzene
4-(2-(3-fluoro-4-ethylphenyl)ethynyl)-1-(2-(2-fluoro-4-propylphenyl)ethynyl)benzene
4-(2-(3-fluoro-4-ethylphenyl)ethynyl)-1-(2-(2-fluoro-4-butylphenyl)ethynyl)benzene
4-(2-(3-fluoro-4-ethylphenyl)ethynyl)-1-(2-(2-fluoro-4-pentylphenyl)ethynyl)benzene
4-(2-(3-fluoro-4-ethylphenyl)ethynyl)-1-(2-(2-fluoro-4-hexylphenyl)ethynyl)benzene
4-(2-(3-fluoro-4-ethylphenyl)ethynyl)-1-(2-(2-fluoro-4-heptylphenyl)ethynyl)benzene
4-(2-(3-fluoro-4-propylphenyl)ethynyl)-1-(2-(2-fluoro-4-methylphenyl)ethynyl)benzene
4-(2-(3-fluoro-4-propylphenyl)ethynyl)-1-(2-(2-fluoro-4-ethylphenyl)ethynyl)benzene
4-(2-(3-fluoro-4-propylphenyl)ethynyl)-1-(2-(2-fluoro-4-propylphenyl)ethynyl)benzene
4-(2-(3-fluoro-4-propylphenyl)ethynyl)-1-(2-(2-fluoro-4-butylphenyl)ethynyl)benzene
4-(2-(3-fluoro-4-propylphenyl)ethynyl)-1-(2-(2-fluoro-4-pentylphenyl)ethynyl)benzene
4-(2-(3-fluoro-4-propylphenyl)ethynyl)-1-(2-(2-fluoro-4-hexylphenyl)ethynyl)benzene
4-(2-(3-fluoro-4-propylphenyl)ethynyl)-1-(2-(2-fluoro-4-eptylphenyl)ethynyl)benzene
4-(2-(3-fluoro-4-butylphenyl)ethynyl)-1-(2-(2-fluoro-4-ethylphenyl)ethynyl)benzene
4-(2-(3-fluoro-4-butylphenyl)ethynyl)-1-(2-(2-fluoro-4-thylphenyl)ethynyl)benzene
4-(2-(3-fluoro-4-butylphenyl)ethynyl)-1-(2-(2-fluoro-4-propylphenyl)ethynyl)benzene
4-(2-(3-fluoro-4-butylphenyl)ethynyl)-1-(2-(2-fluoro-4-butylphenyl)ethynyl)benzene
4-(2-(3-fluoro-4-butylphenyl)ethynyl)-1-(2-(2-fluoro-4-pentylphenyl)ethynyl)benzene 4-(2-(3-fluoro-4-butylphenyl)ethynyl)-1-(2-(2-fluoro-4-hexylphenyl)ethynyl)benzene
4-(2-(3-fluoro-4-butylphenyl)ethynyl)-1-(2-(2-fluoro-4-heptylphenyl)ethynyl)benzene
4-(2-(3-fluoro-4-pentylphenyl)ethynyl)-1-(2-(2-fluoro-4-methylphenyl)ethynyl)benzene
4-(2-(3-fluoro-4-pentylphenyl)ethynyl)-1-(2-(2-fluoro-4-ethylphenyl)ethynyl)benzene
4-(2-(3-fluoro-4-pentylphenyl)ethynyl)-1-(2-(2-fluoro-4-propylphenyl)ethynyl)benzene
4-(2-(3-fluoro-4-pentylphenyl)ethynyl)-1-(2-(2-fluoro-4-butylphenyl)ethynyl)benzene
4-(2-(3-fluoro-4-pentylphenyl)ethynyl)-1-(2-(2-fluoro-4-pentylphenyl)ethynyl)benzene
4-(2-(3-fluoro-4-pentylphenyl)ethynyl)-1-(2-(2-fluoro-4-hexylphenyl)ethynyl)benzene
4-(2-(3-fluoro-4-pentylphenyl)ethynyl)-1-(2-(2-fluoro-4-heptylphenyl)ethynyl)benzene
4-(2-(3-fluoro-4-hexylphenyl)ethynyl)-1-(2-(2-fluoro-4-methylphenyl)ethynyl)benzene
4-(2-(3-fluoro-4-hexylphenyl)ethynyl)-1-(2-(2-fluoro-4-ethylphenyl)ethynyl)benzene
4-(2-(3-fluoro-4-hexylphenyl)ethynyl)-1-(2-(2-fluoro-4-propylphenyl)ethynyl)benzene
4-(2-(3-fluoro-4-hexylphenyl)ethynyl)-1-(2-(2-fluoro-4-butylphenyl)ethynyl)benzene
4-(2-(3-fluoro-4-hexylphenyl)ethynyl)-1-(2-(2-fluoro-4-pentylphenyl)ethynyl)benzene
4-(2-(3-fluoro-4-hexylphenyl)ethynyl)-1-(2-(2-fluoro-4-hexylphenyl)ethynyl)benzene
4-(2-(3-fluoro-4-hexylphenyl)ethynyl)-1-(2-(2-fluoro-4-heptylphenyl)ethynyl)benzene
4-(2-(3-fluoro-4-heptylphenyl)ethynyl)-1-(2-(2-fluoro-4-methylphenyl)ethynyl)benzene
4-(2-(3-fluoro-4-heptylphenyl)ethynyl)-1-(2-(2-fluoro-4-ethylphenyl)ethynyl)benzene
4-(2-(3-fluoro-4-heptylphenyl)ethynyl)-1-(2-(2-fluoro-4-propylphenyl)ethynyl)benzene
4-(2-(3-fluoro-4-heptylphenyl)ethynyl)-1-(2-(2-fluoro-4-butylphenyl)ethynyl)benzene
4-(2-(3-fluoro-4-heptylphenyl)ethynyl)-1-(2-(2-fluoro-4-pentylphenyl)ethynyl)benzene
4-(2-(3-fluoro-4-heptylphenyl)ethynyl)-1-(2-(2-fluoro-4-hexylphenyl)ethynyl)benzene
4-(2-(3-fluoro-4-heptylphenyl)ethynyl)-1-(2-(2-fluoro-4-heptylphenyl)ethynyl)benzene
4-(2-(3-fluoro-4-methylphenyl)ethynyl)-1-(2-(3-fluoro-4-methylphenyl)ethynyl)benzene
4-(2-(3-fluoro-4-methylphenyl)ethynyl)-1-(2-(3-fluoro-4-ethylphenyl)ethynyl)benzene
4-(2-(3-fluoro-4-methylphenyl)ethynyl)-1-(2-(3-fluoro-4-propylphenyl)ethynyl)benzene
4-(2-(3-fluoro-4-methylphenyl)ethynyl)-1-(2-(3-fluoro-4-butylphenyl)ethynyl)benzene
4-(2-(3-fluoro-4-methylphenyl)ethynyl)-1-(2-(3-fluoro-4-pentylphenyl)ethynyl)benzene
4-(2-(3-fluoro-4-methylphenyl)ethynyl)-1-(2-(3-fluoro-4-hexylphenyl)ethynyl)benzene
4-(2-(3-fluoro-4-methylphenyl)ethynyl)-1-(2-(3-fluoro-4-beptylphenyl)ethynyl)benzene
4-(2-(3-fluoro-4-ethylphenyl)ethynyl)-1-(2-(3-fluoro-4-methylphenyl)ethynyl)benzene
4-(2-(3-fluoro-4-ethylphenyl)ethynyl)-l1-(2-(3-fluoro-4-ethylphenyl)ethynyl)benzene
4-(2-(3-fluoro-4-ethylphenyl)ethynyl)-1-(2-(3-fluoro-4-propylphenyl)ethynyl)benzene
4-(2-(3-fluoro-4-ethylphenyl)ethynyl)-1-(2-(3-fluoro-4-butylphenyl)ethynyl)benzene
4-(2-(3-fluoro-4-ethylphenyl)ethynyl)-1-(2-(3-fluoro-4-pentylphenyl)ethynyl)benzene
4-(2-(3-fluoro-4-ethylphenyl)ethynyl)-1-(2-(3-fluoro-4-hexylphenyl)ethynyl)benzene
4-(2-(3-fluoro-4-ethylphenyl)ethynyl)-1-(2-(3-fluoro-4-heptylphenyl)ethynyl)benzene
4-(2-(3-fluoro-4-propylphenyl)ethynyl)-1-(2-(3-fluoro-4-methylphenyl)ethynyl)benzene
4-(2-(3-fluoro-4-propylphenyl)ethynyl)-1-(2-(3-fluoro-4-ethylphenyl)ethynyl)benzene
4-(2-(3-fluoro-4-propylphenyl)ethynyl)-1-(2-(3-fluoro-4-propylphenyl)ethynyl)benzene
4-(2-(3-fluoro-4-propyloxyphenyl)ethynyl)-1-(2-(3-fluoro-4-propylphenyl)ethynyl)benzene
4-(2-(3-fluoro-4-propylphenyl)ethynyl)-1-(2-(3-fluoro-4-butylphenyl)ethynyl)benzene
4-(2-(3-fluoro-4-propylphenyl)ethynyl)-1-(2-(3-fluoro-4-pentylphenyl)ethynyl)benzene
4-(2-(3-fluoro-4-p ropylphenyl)ethynyl)-1-(2-(3-fluoro-4-hexylphenyl)ethynyl)benzene
4-(2-(3-fluoro-4-propylphenyl)ethynyl)-1-(2-(3-fluoro-4-heptylphenyl)ethynyl)benzene
4-(2-(3-fluoro-4-butylphenyl)ethynyl)-1-(2-(3-fluoro-4-methylphenyl)ethynyl)benzene
4-(2-(3-fluoro-4-butylphenyl)ethynyl)-1-(2-(3-fluoro-4-ethylphenyl)ethynyl)benzene
4-(2-(3-fluoro-4-butylphenyl)ethynyl)-1-(2-(3-fluoro-4-propylphenyl)ethynyl)benzene
4-(2-(3-fluoro-4-butylphenyl)ethynyl)-1-(2-(3-fluoro-4-butylphenyl)ethynyl)benzene
4-(2-(3-fluoro-4-butylphenyl)ethynyl)-1-(2-(3-fluoro-4-pentylphenyl)ethynyl)benzene
4-(2-(3-fluoro-4-butylphenyl)ethynyl)-1-(2-(3-fluoro-4-hexylphenyl)ethynyl)benzene i-(2-(3-fluoro-4-butylphenyl)ethynyl)-1-(2-(3-fluoro-4-heptylphenyl)ethynyl)benzene
4-(2-(3-fluoro-4-pentylphenyl)ethynyl)-1-(2-(3-fluoro-4-methylphenyl)ethynyl)benzene
4-(2-(3-fluoro-4-pentylphenyl)ethynyl)-1-(2-(3-fluoro-4-ethylphenyl)ethynyl)benzene
4-(2-(3-fluoro-4-pentylphenyl)ethynyl)-1-(2-(3-fluoro-4-propylphenyl)ethynyl)benzene
4-(2-(3-fluoro-4-pentylphenyl)ethynyl)-1-(2-(3-fluoro-4-butylphenyl)ethynyl)benzene
4-(2-(3-fluoro-4-pentylphenyl)ethynyl)-1-(2-(3-fluoro-4-pentylphenyl)ethynyl)benzene
4-(2-(3-fluoro-4-pentylphenyl)ethynyl)-1-(2-(3-fluoro-4-hexylphenyl)ethynyl)benzene
4-(2-(3-fluoro-4-pentylphenyl)ethynyl)-1-(2-(3-fluoro-4-hexylphenyl)ethynyl)benzene
4-(2-(3-fluoro-4-pentylphenyl)ethynyl)-1-(2-(3-fluoro-4-heptylphenyl)ethynyl)benzene 4-(2-(3-fluoro-4-hexylphenyl)ethynyl)-1-(2-(3-fluoro-4-methylphenyl)ethynyl)benzene
4-(2-(3-fluoro-4-hexylphenyl)ethyny)-1-(2-(3-fluoro-4-ethylphenyl)ethynyl)benzene
4-(2-(3-fluoro-4-hexylphenyl)ethynyl)-1-(2-(3-fluoro-4-prop ylphenyl)ethynyl)benzene
4-(2-(3-fluoro-4-hexylphenyl)ethynyl)-1-(2-(3-fluoro-4-butylphenyl)ethynyl)benzene
4-(2-(3-fluoro-4-hexylphenyl)ethynyl)-1-(2-(3-fluoro-4-pentylphenyl)ethynyl)benzene
4-(2-(3-fluoro-4-hexylphenyl)ethynyl)-1-(2-(3-fluoro-4-hexylphenyl)ethynyl)benzene
4-(2-(3-fluoro-4-hexylphenyl)ethynyl)-1-(2-(3-fluoro-4-heptylphenyl)ethynyl)benzene
4-(2-(3-fluoro-4-heptylphenyl)ethynyl)-1-(2-(3-fluoro-4-methylphenyl)ethynyl)benzene
4-(2-(3-fluoro-4-heptylphenyl)ethynyl)-1-(2-(3-fluoro-4-ethylphenyl)ethynyl)benzene
4-(2-(3-fluoro-4-heptylphenyl)ethynyl)-1-(2-(3-fluoro-4-propylphenyl)ethynyl)benzene
4-(2-(3-fluoro-4-heptylphenyl)ethynyl)-1-(2-(3-fluoro-4-butylphenyl)ethynyl)benzene
4-(2-(3-fluoro-4-heptylphenyl)ethynyl)-1-(2-(3-fluoro-4-pentylphenyl)ethynyl)benzene
4-(2-(3-fluoro-4-heptylphenyl)ethynyl)-1-(2-(3-fluoro-4-hexylphenyl)ethynyl)benzene
4-(2-(3-fluoro-4-heptylphenyl)ethynyl)-1-(2-(3-fluoro-4-heptylphenyl)ethynyl)benzene Any acetylene derivatives represented by general formula (1) can be prepared by well-known method of organic synthetic chemistry. For example, methods described in Organic Synthesis (published by John Wiley and Sons Inc.), Organic reactions (published by John Wiley and Sons Inc.), or Jikken Kagaku Kouza (published by Maruzen) can be suitably combined to easily synthesize the derivatives.

By common methods of organic synthetic chemistry, the compounds of formula (1) can be easily prepared, for example, by the following example. In the following, $H_1$, $H_2$, $H_3$, $H_4$, $H_5$, $H_6$, $H_7$, $H_8$, $H_9$, $H_{10}$, $H_{11}$ and $H_{12}$ represent the same meaning as described above, and Hal represents a bromine atom or an iodine atom.

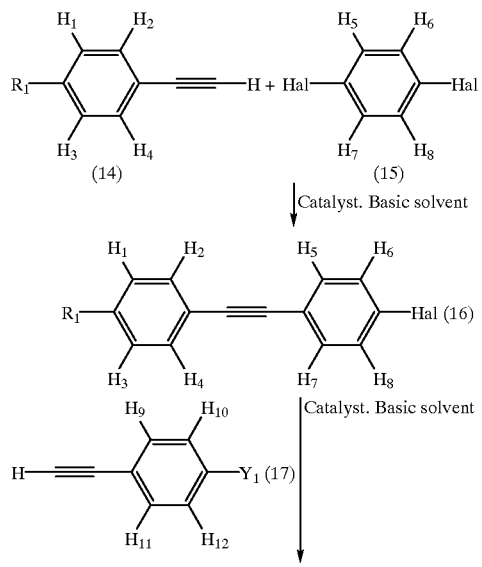

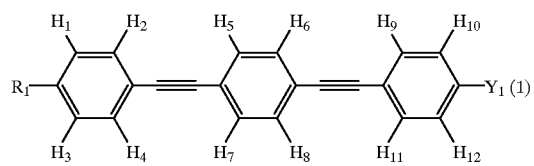

The acetylene derivatives of formula (1) can be prepared by repeating twice alkyne production reaction. In that case, there is no problem by using the most performable Castro reaction (J. Org. Chem., 28, 2163 (1963)). When $R_1$ and $Y_1$ are the same, it is unnecessary to conduct a two step reaction. The acetylene derivatives of formula (1) can be prepared by one step.

Halogenated compound (15) can be reacted with phenyl acetylene derivative (14) under basic conditions in the presence of a catalyst to obtain tolan derivative (16). As the solvent, well-known amine compounds such as diethylamine, diethylaniline, triethylamine can be used. As the catalyst, a Pd type or Ni type compound can be preferably used.

For simple operation of the first step, the compound of formula (15) in which two halogen atoms are different at the 1- and 4-positions is used. When a 4-iodo-1-bromo benzene derivative is used, the first step reaction selectively proceeds on the iodine atom, so that the production of three rings' compound can be depressed. Otherwise, the compound should be removed at the next step reaction.

The compound of formula (17) is reacted with tolan derivative (16) under the same condition as described in the above, and the acetylene derivative of formula (1) can be produced.

The phenyl acetylene derivative of formula (14) or (17) used in the above reaction can be easily produced by the following method.

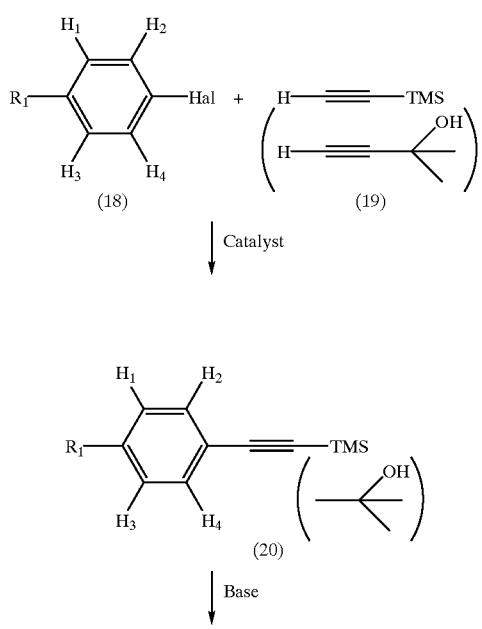

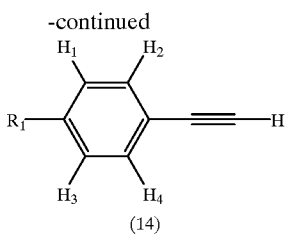

(14)

Acetylene derivative (19), which is protected at the one end side by a protection group such as a trimethylsilyl group (TMS), is reacted with halogen compound (18) to obtain an addition compound (20), and then the protection group is removed to obtain the phenylacetylene derivative of formula (14) or (17). As acetylene derivative (19) protected at the one end, trimethylsilylacetylene, 3-methyl-3-hydroxy-1-butyne or the like can be preferably used. Moreover, the phenylacetylene of formula (14) can be prepared from acetophenone derivative (21).

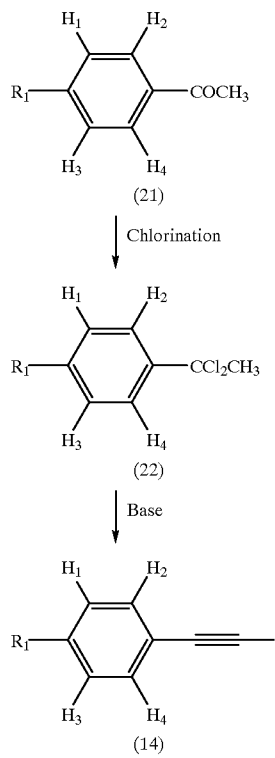

The carbonyl group of the acetophenone derivative of formula (21) is chlorinated to obtain the 1,1-dichloroethane derivative of formula (22), and then the derivative is reacted in the presence of a strong base by dehydrohochlorination reaction to obtain phenyl acetylene derivative (14).

The compounds of formulas (14) and (17), wherein $R_1$ or $Y_1$ is an alkyl group, an alkoxy group, an alkoxyalkyl group, a halogen-substituted alkyl group, a halogenated alkoxy group, a halogen-substituted alkoxyalkyl group, a thioalkyl group, alkyldimethylsilyl group, or alkyldihydroxy-silyl group, can be produced by the common method of iodination or bromination of the 4-position of the corresponding replaced benzene. The compounds of formulas (14) and (17), wherein $R_1$ or $Y_1$ is an alkenyl group, an alkynyl group, an alkenyloxy group, an alkynyloxy group, a halogen-substituted alkenyl group, or a halogenated alkynyl group, can be preferably produced by the following method.

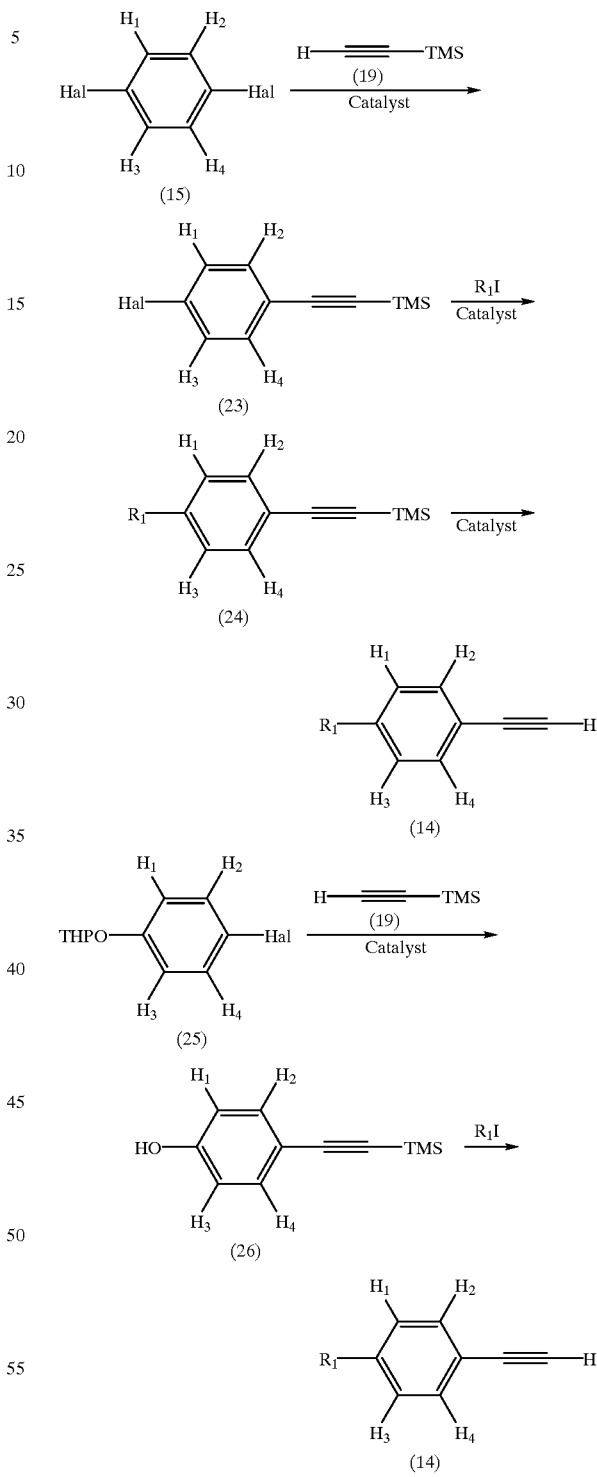

When $R_1$ or $Y_1$ is an alkenyl group or a halogen-substituted alkenyl group, compound (19) is reacted with dihalogeno compound (15) by the method described above to obtain compound (23), then the resulting compound is reacted with a Grignard reagent $R_1$ or a lithium compound by a cross coupling reaction to obtain compound (24), and then the protection group is removed to obtain compound (14). Instead of $R_1I$, $Y_1I$ can be used to produce compound (17).

When $R_1$ or $Y_1$ is an alkenyloxy group or an alkynyloxy group, alkynyl parts are introduced into compound (25), in which the hydroxy group of 4-halogenophenol has been protected by a tetrahydropyranyl (THP) group, by the said method, the THP group is removed under acidic conditions, and the resulting compound (26) is reacted with alkenylhalide or alkynylhahide, and after removing TMS, compound (14) is obtained. Using the same method, compound (17) can be obtained.

Moreover, when $R_1$ or $Y_1$ is an alkynyl group or a halogen-substituted alkynyl group, the compound can be obtained by the following method.

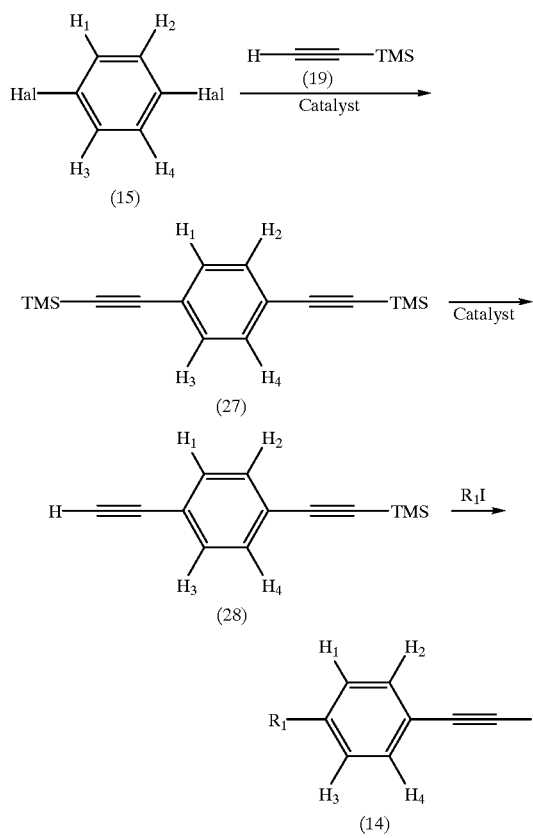

After compound (15) reacted with trimethylsilylacetylene to obtain compound (27), a TMS group is selectively removed to obtain compound (28). The compound is reacted with alkylhalide or halogen-substituted alkylhalide by a common method under basic conditions, and the TMS group of a protection group is removed to obtain compound (14). Compound (17) can be obtained by the same method.

The liquid crystal compositions provided by the present invention comprise at least one of acetylene derivatives represented by formula (1) as a first component, and liquid crystalline components as a second or more components.

The liquid crystal compositions of the present invention have improved Δn by adding the acetylene derivative represented by the formula (1) as the component, which is characteristic of the composition.

The composition of the present invention is obtained by mixing the compounds selected from the group of general formulas (2)–(9) as a second or more components according to the purpose of the use.

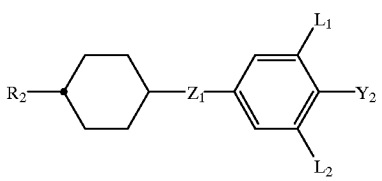

(2)

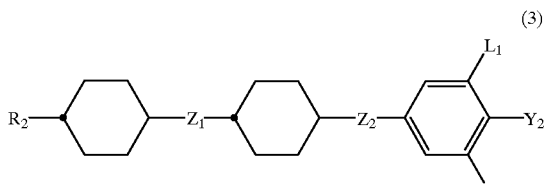

(3)

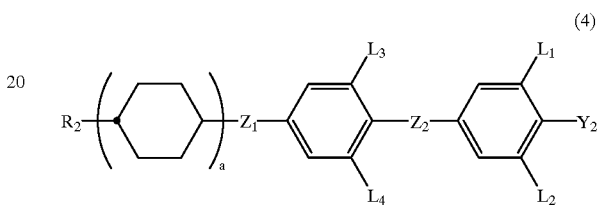

(4)

wherein $R_2$ represents an alkyl group of 1–10 carbon atoms; $Y_2$ represents a fluorine atom, a chlorine atom, $OCF_3$, $OCHF_2$, $CF_3$, $CHF_2$ or $CH_2F$; $L_1$, $L_2$, $L_3$ and $L_4$, each independently, represent a hydrogen atom or a fluorine atom; $Z_1$ and $Z_2$, each independently, represent $-CH_2CH_2-$, $-CH=CH-$ or a covalent bond; and a represent 1 or 2.

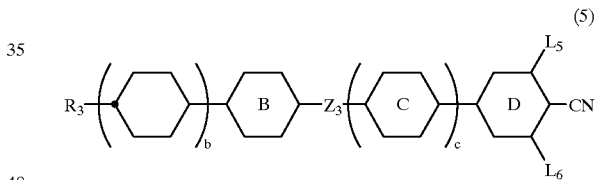

(5)

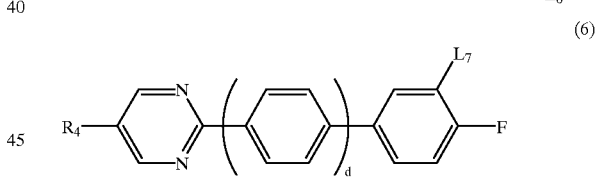

(6)

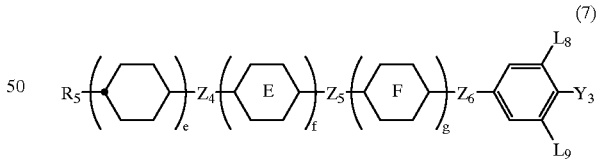

(7)

wherein $R_3$ represents a fluorine atom, an alkyl group of 1–10 carbon atoms or an alkenyl group of 2–10 carbon atoms, in which one or more not-adjacent methylene groups may be replaced by an oxygen atom; $R_4$ and $R_5$ represent an alkyl group of 1–10 carbon atoms; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D, six-membered ring E and six-membered ring F, each independently, represent trans-1,4-cyclohexylene or 1,4-phenylene; $Z_3$ represents $-CH_2CH_2-$, $-COO-$ or a covalent bond; $Z_4$ and $Z_5$, each independently, represent $-COO-$ or a covalent bond;

$Z_6$ represents —COO— or —C≡C—; $Y_3$ represents a fluorine atom, $OCF_3$, $OCHF_2$, $CF_3$, $CHF_2$ or $CH_2F$; $L_5$, $L_6$, $L_7$, $L_8$ and $L_9$ each independently, represent a hydrogen atom or a fluorine atom; b, c, d, e, f and g, each independently, represent 0 or 1. However, e, f and g are not 0 at the same, when e is 0, $Z_4$ is a covalent bond, when f or g is 0, $Z_5$ is a covalent bond, and when f and g are 0, $Z_4$ is also a covalent bond.

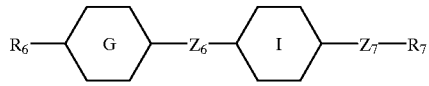
(8)

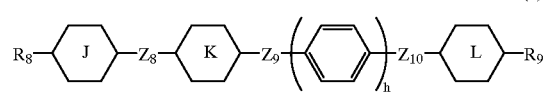
(9)

wherein $R_6$, $R_7$, $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring G and six-membered ring J represent trans-1,4-cyclohexylene, 1,4-phenylene or pyrimidine-2,5-diyl; six-membered ring I and six-membered ring L represent trans-1,4-cyclohexylene or 1,4-phenylene; six-membered ring K represents trans-1,4-cyclohexylene, pirimidine-2,5-diyl or 1,4-phenylene, in which one or more hydrogen atoms at the sides may be replaced by fluorine atoms; $Z_6$ represents —C≡C—, —COO—, —$CH_2CH_2$—, —CH=CH—C≡C— or a covalent bond; and $Z_7$ represents —COO— or a covalent bond; $Z_8$ and $Z_{10}$, each independently, represent —COO—, —$CH_2CH_2$— or a covalent bond; $Z_9$ represents —CH=CH—, —C≡C—, —COO— or a covalent bond; and h represents 0 or 1. However, when h is 0, at least any one of $Z_9$ and $Z_{10}$ is a covalent bond.

The compounds of common formula (2) used in the present invention can be exemplified preferably the following compounds. In this formula, $R_2$ has the same meaning as described above.

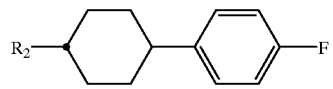
(2-1)

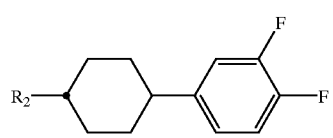
(2-2)

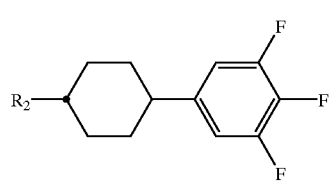
(2-3)

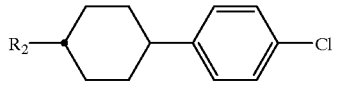
(2-4)

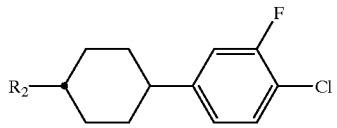
(2-5)

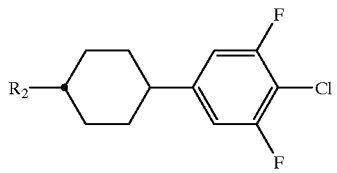
(2-6)

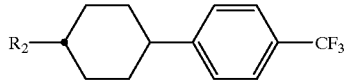
(2-7)

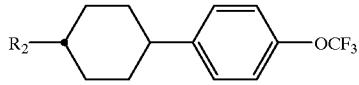
(2-8)

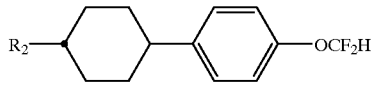
(2-9)

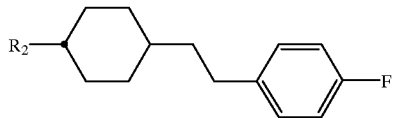
(2-10)

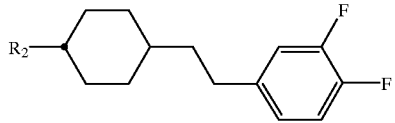
(2-11)

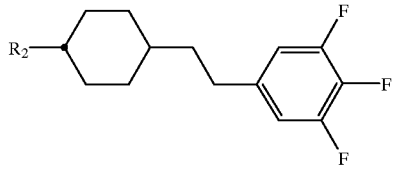
(2-12)

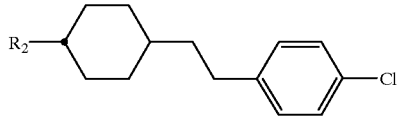
(2-13)

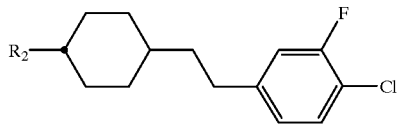
(2-14)

-continued
(2-15)
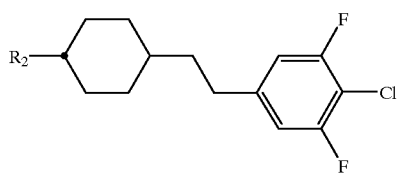
The preferable compounds represented by formula (3) of a second components are exemplified as follows. In the formula, $R_2$ has the same meaning as described above.
(3-1)
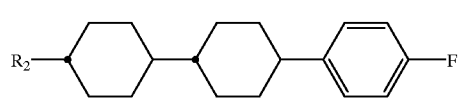
(3-2)
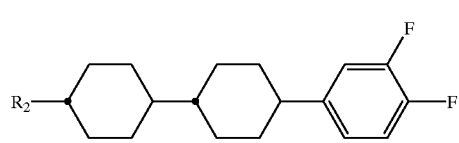
(3-3)
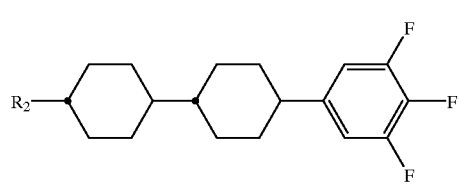
(3-4)
(3-5)
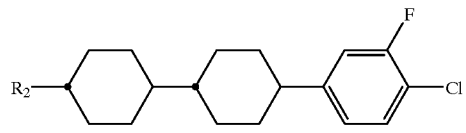
(3-6)
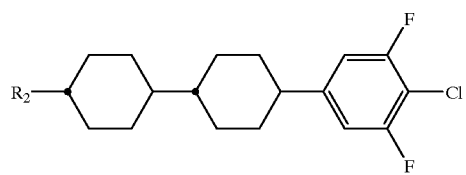
(3-7)
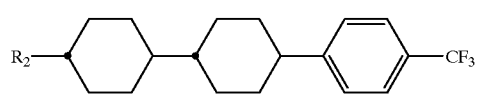
(3-8)
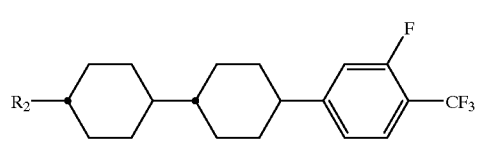
-continued
(3-9)
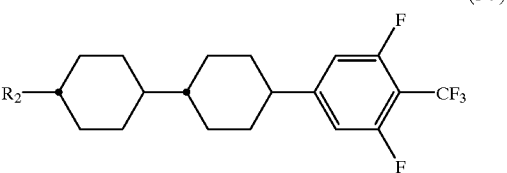
(3-10)
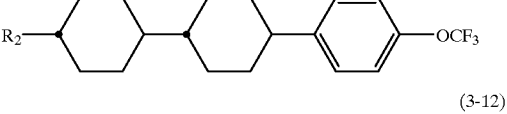
(3-11)
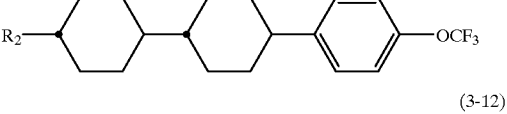
(3-12)
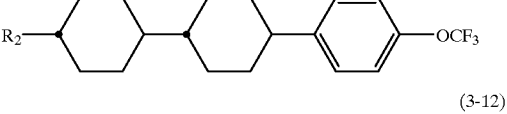
(3-13)
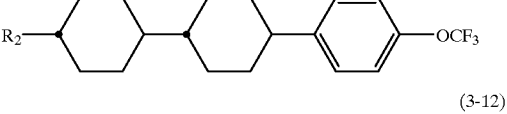
(3-14)
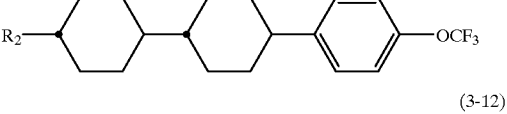
(3-15)
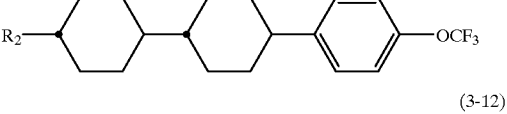
(3-16)
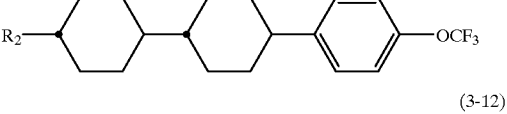
(3-17)
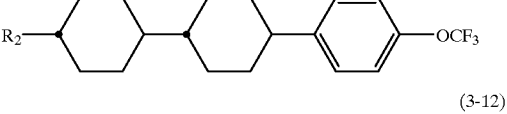
(3-18)
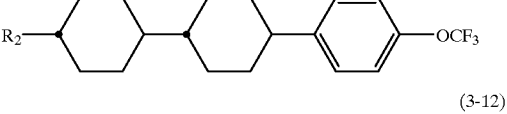

(3-19)
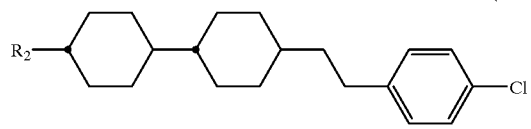
(3-20)
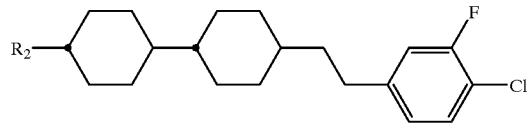
(3-21)
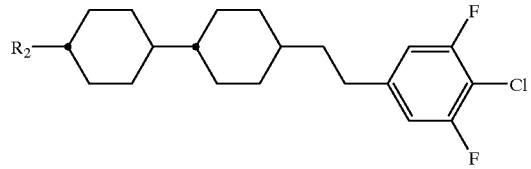
(3-22)
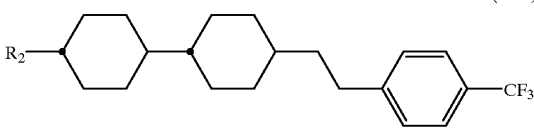
(3-23)
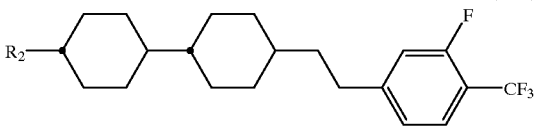
(3-24)
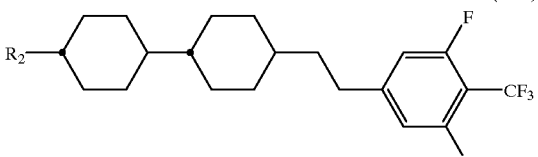
(3-25)
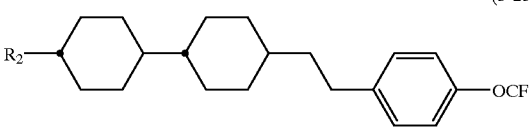
(3-26)
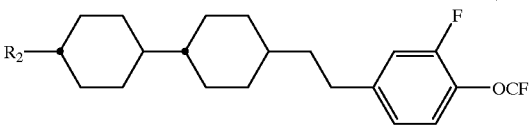
(3-27)
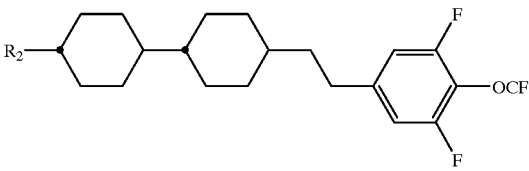
(3-28)
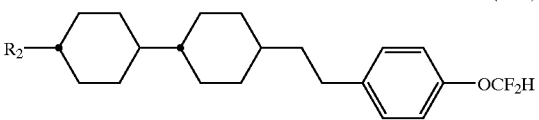
(3-29)
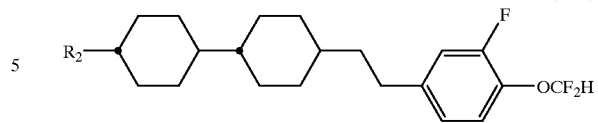
(3-30)
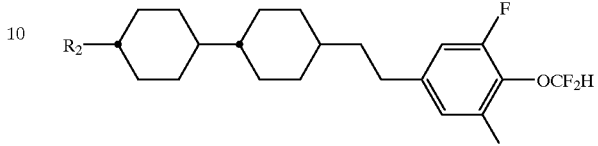
(3-31)
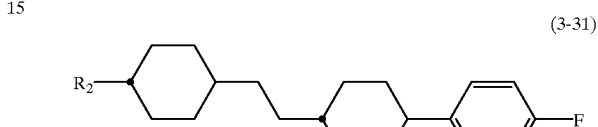
(3-32)
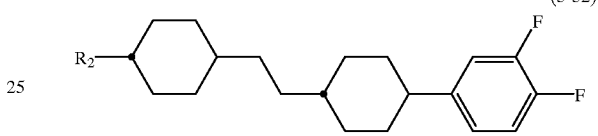
(3-33)
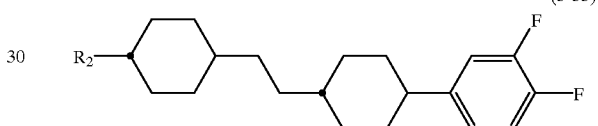
(3-34)
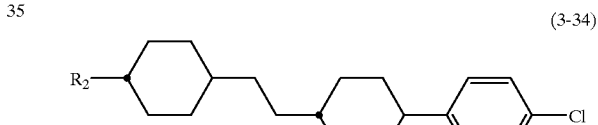
(3-35)
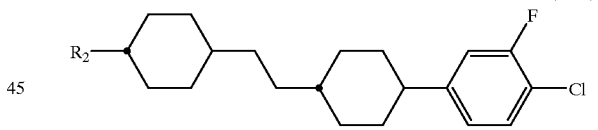
(3-36)
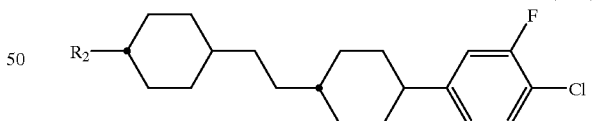
(3-37)
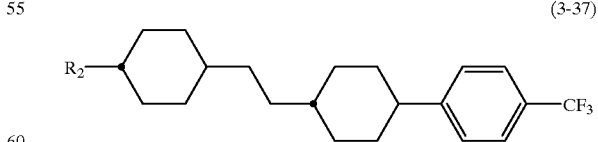
(3-38)
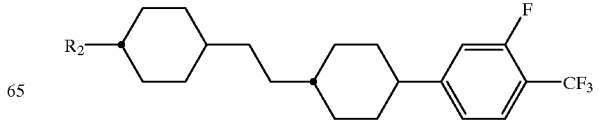

(3-39)
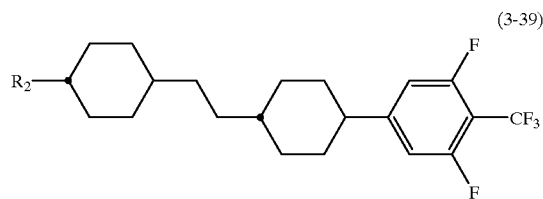
(3-40)
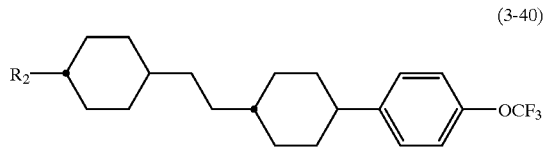
(3-41)
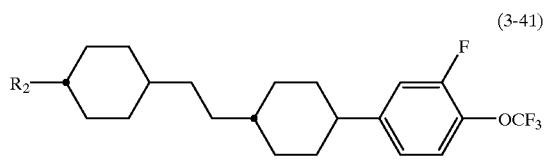
(3-42)
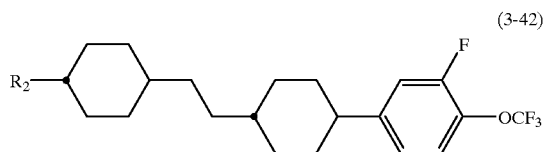
(3-43)
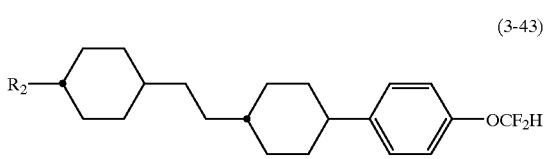
(3-44)
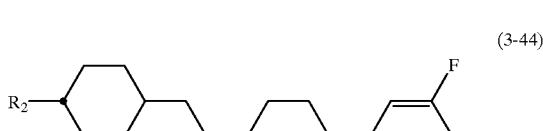
(3-45)
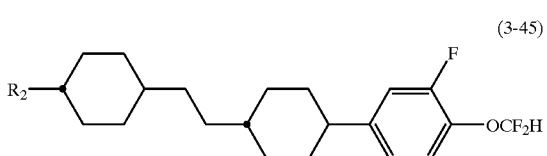
(3-46)
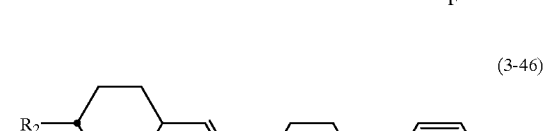
(3-47)
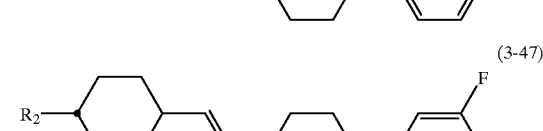
(3-48)
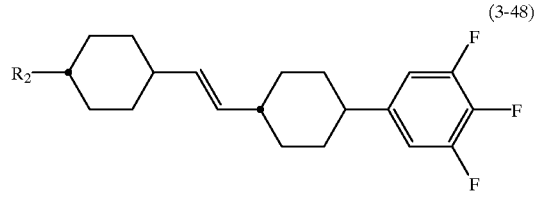
The compounds represented by formula (4) of a second component can be exemplified in the following. In these formulas, $R_2$ has the same meaning as described above.
(4-1)
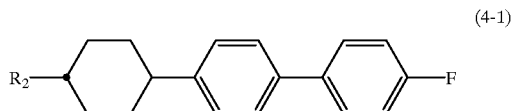
(4-2)
(4-3)
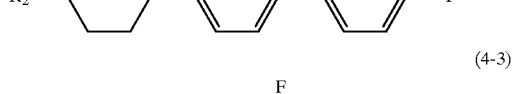
(4-4)
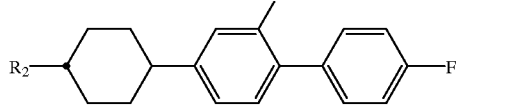
(4-5)
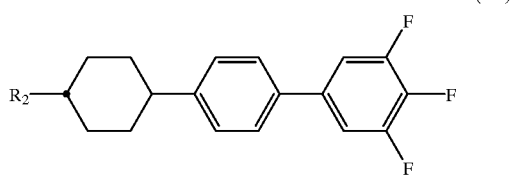
(4-6)
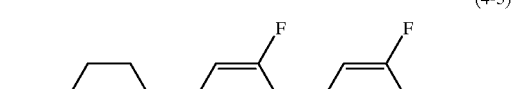
(4-7)
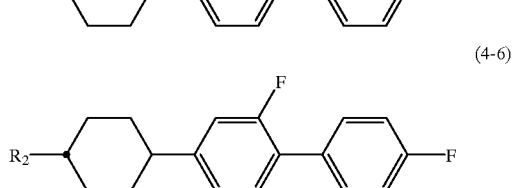
(4-8)
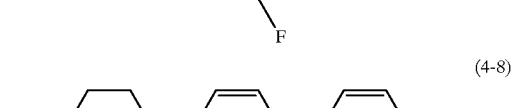

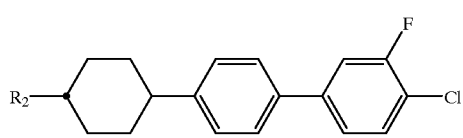
(4-9)
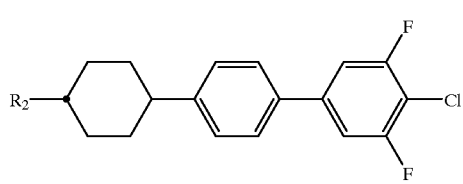
(4-10)
(4-11)
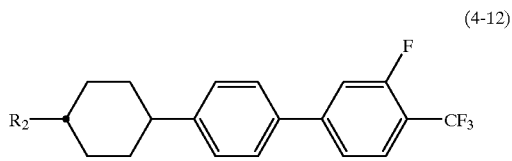
(4-12)
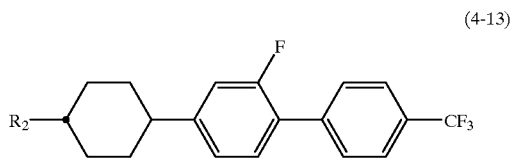
(4-13)
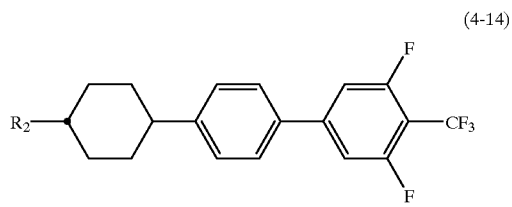
(4-14)
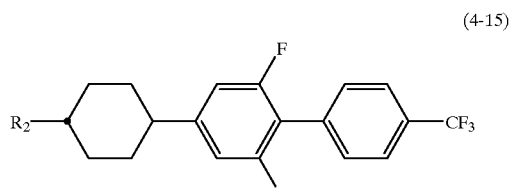
(4-15)
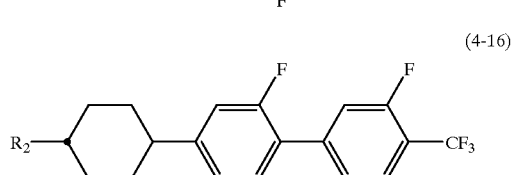
(4-16)
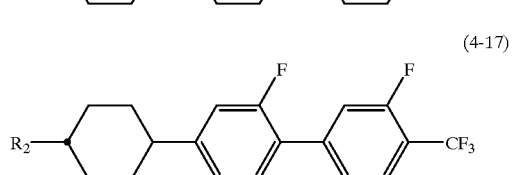
(4-17)
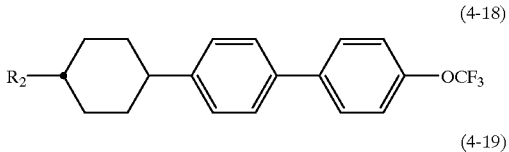
(4-18)
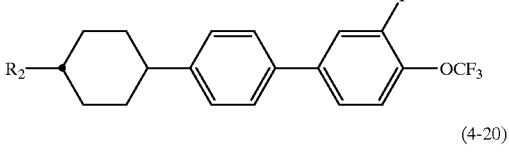
(4-19)
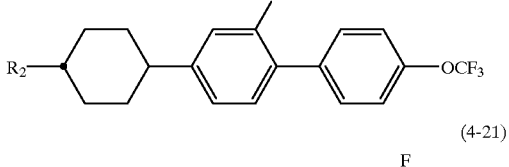
(4-20)
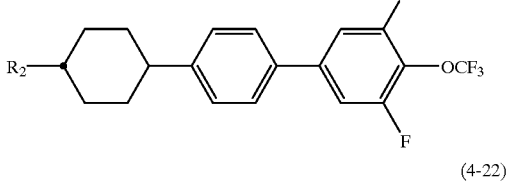
(4-21)
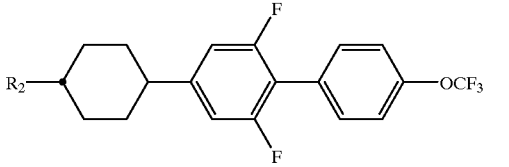
(4-22)
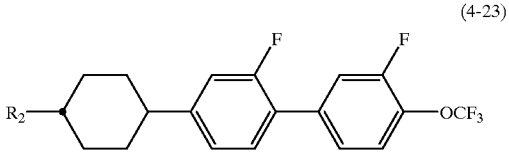
(4-23)
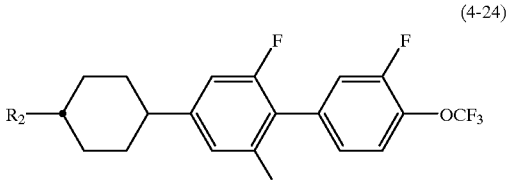
(4-24)
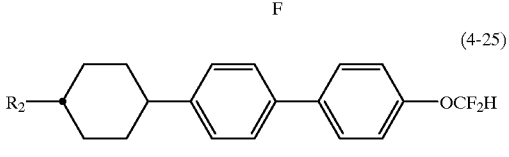
(4-25)
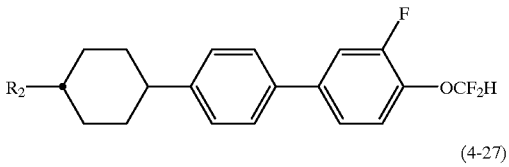
(4-26)
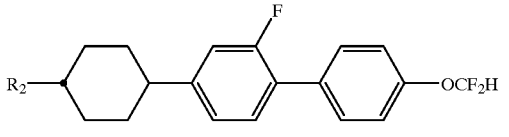
(4-27)

-continued
(4-28)
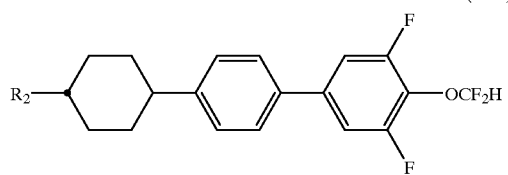
(4-29)
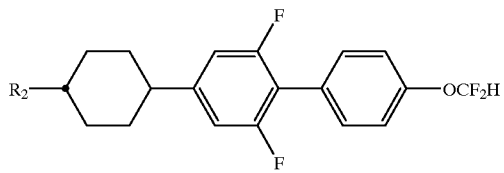
(4-30)
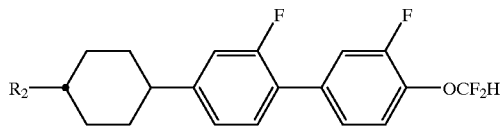
(4-31)
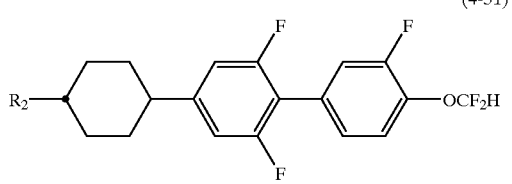
(4-32)
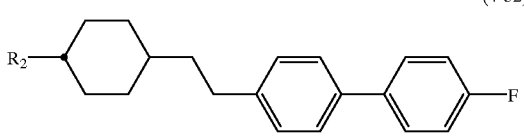
(4-33)
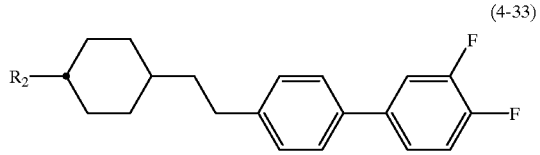
(4-34)
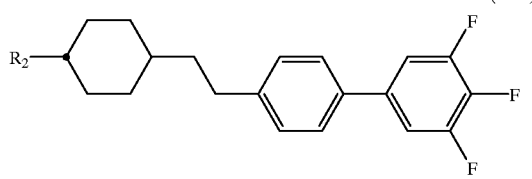
(4-35)
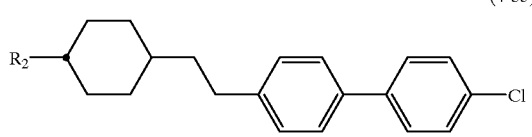
(4-36)
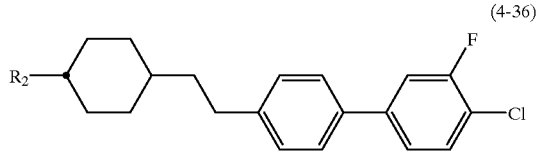
-continued
(4-37)
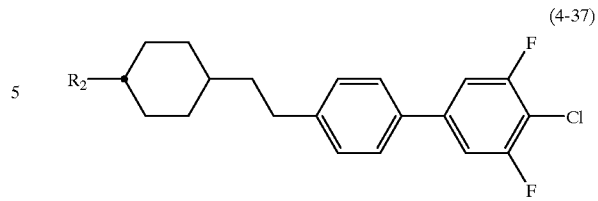
(4-38)
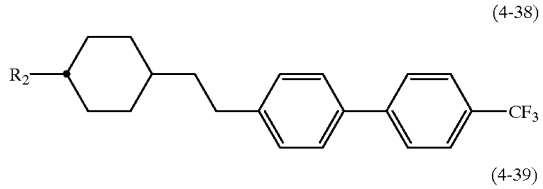
(4-39)
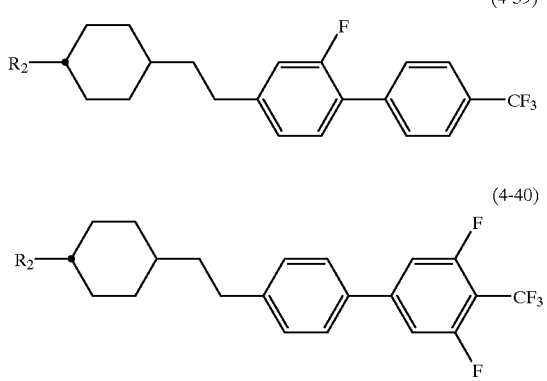
(4-40)
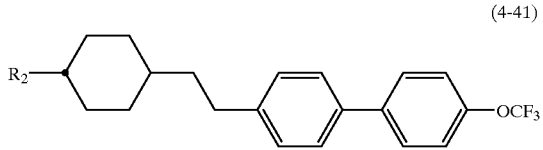
(4-41)
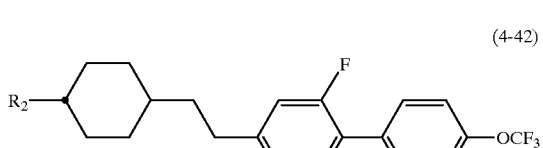
(4-42)
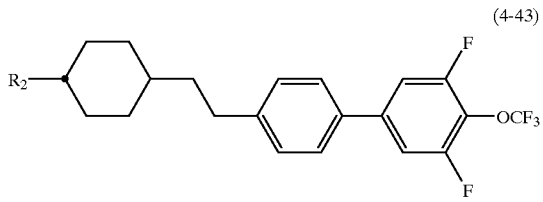
(4-43)
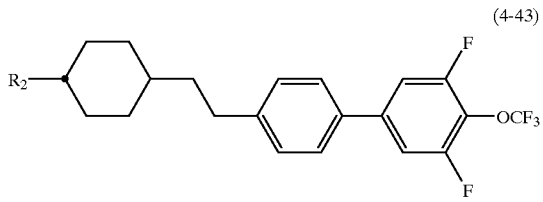
(4-44)
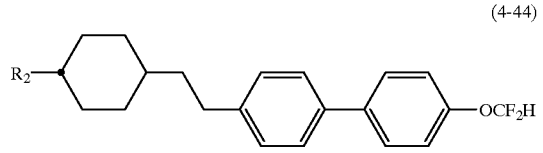
(4-45)
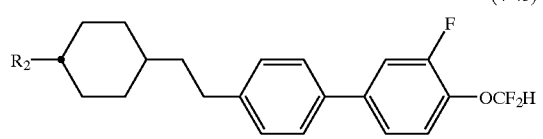

The compounds represented by general formulas (2), (3) or (4) have positive dielectric anisotropy values and excellent heat stability and chemical stability, and particularly, the compounds are preferably used in case of production of the liquid crystal compositions for TFT that high reliability such as a high voltage holding ratio or high specific resistance value is required.

As a second component, when the compounds represented by general formulas (2), (3) or (4) can be used to obtain liquid crystal compositions for TFT, the mixing ratio of these compounds as a second component is 1–99% by weight for the total weights, preferably 10–97% by weight and more preferably 10–95% by weight. In the case, the compounds represented by general formulas (5)–(9) can be partly contained.

The compositions of the present invention can be used in the liquid crystal compositions for a STN display mode or a TN display mode. The compounds represented by general formulas (2), (3) or (4) can be also used as a second component.

In the compositions of the present invention, the compounds represented by general formulas (5)–(7) can be preferably exemplified in the following. $R_3$–$R_5$ have the same meaning as described in the above.

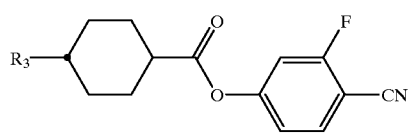 (5-11)
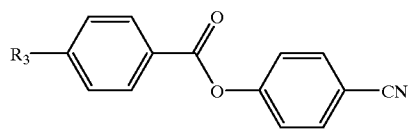 (5-12)
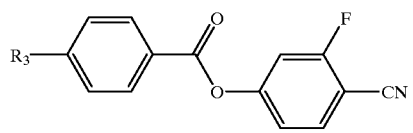 (5-13)
 (5-14)
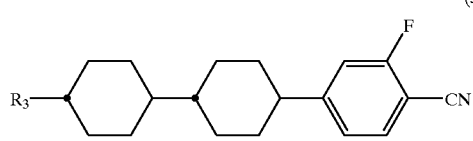 (5-15)
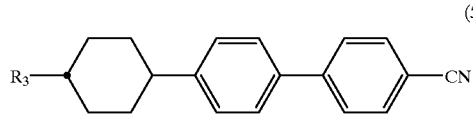 (5-16)
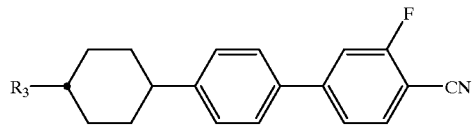 (5-17)
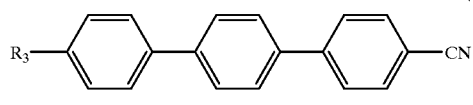 (5-18)
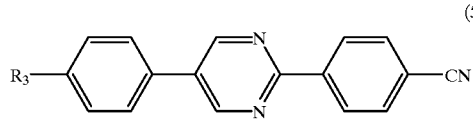 (5-19)
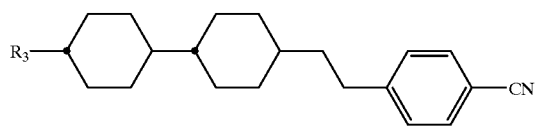 (5-20)
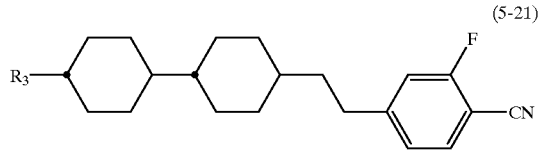 (5-21)
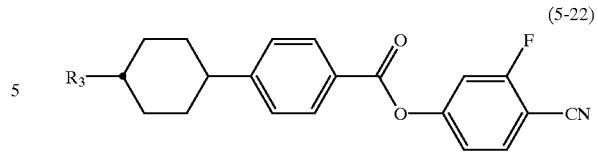 (5-22)
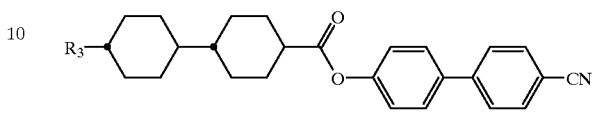 (5-23)
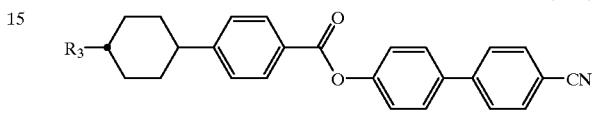 (5-24)
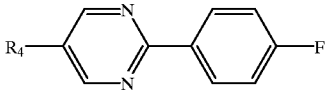 (6-1)
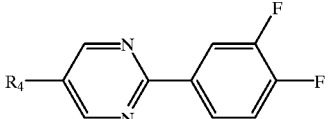 (6-2)
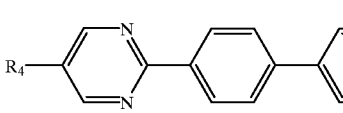 (6-3)
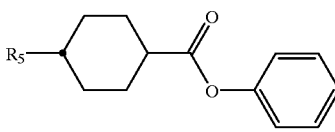 (7-1)
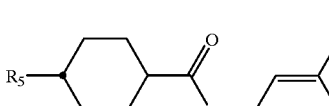 (7-2)
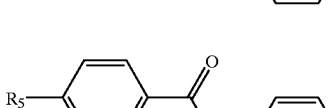 (7-3)
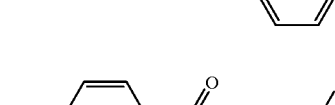 (7-4)
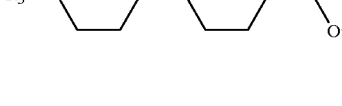 (7-5)

(7-6), (7-7), (7-8), (7-9), (7-10), (7-11), (7-12), (7-13), (7-14), (7-15), (7-16), (7-17), (7-18), (7-19), (7-20), (7-21), (7-22), (7-23), (7-24)

(7-25)
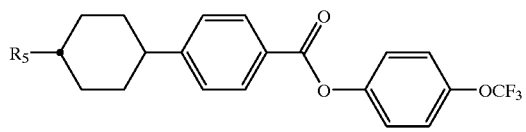

(7-26)
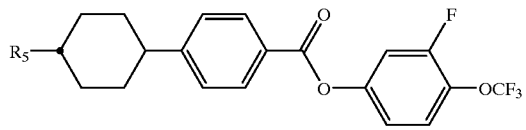

(7-27)
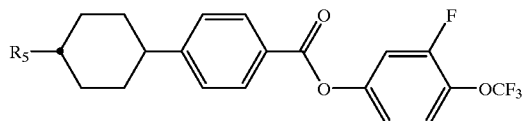

(7-28)
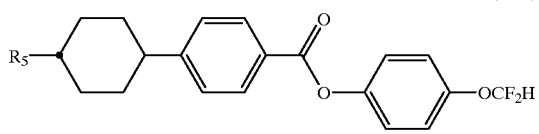

Since the compounds represented by general formulas (5)–(7) have a high positive dielectric anisotropy value, it is particularly used for decreasing the threshold value of the resulting compositions. The compounds are also used for broadening the nematic range such as viscosity adjustment of the compositions, adjustment of dielectric anisotropy values, and obtention of high clearing points. The compounds are further used for improving the steepness of V-T characteristic.

The prefarable compounds represented by general formulae (8) and (9) in the compositions of the present invention are exemplified in the following. $R_6$–$R_9$ have the same meaning as described in the above.

(8-1)
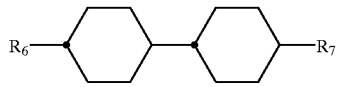

(8-2)
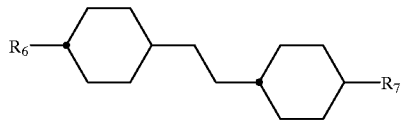

(8-3)
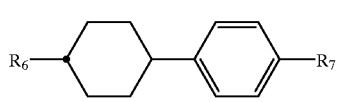

(8-4)
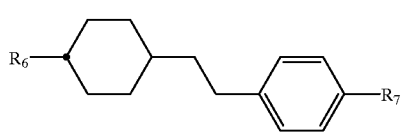

(8-5)
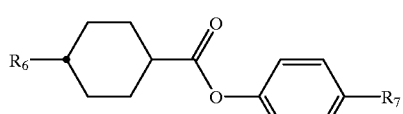

(8-6)
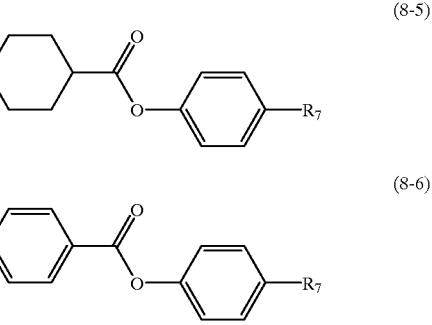

(8-7)
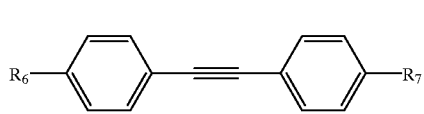

(8-8)
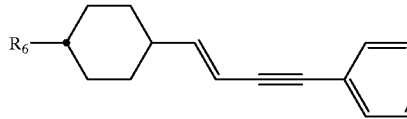

(9-1)
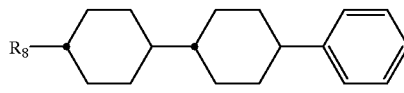

(9-2)
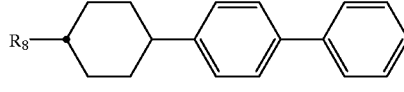

(9-3)
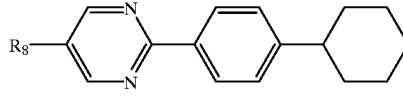

(9-4)
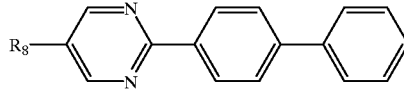

(9-5)
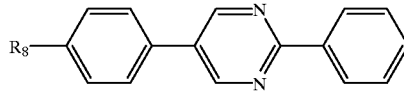

(9-6)
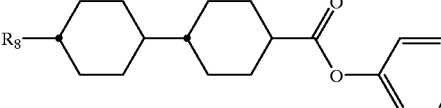

(9-7)
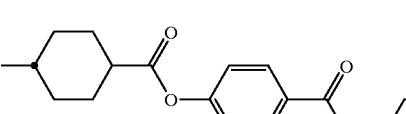

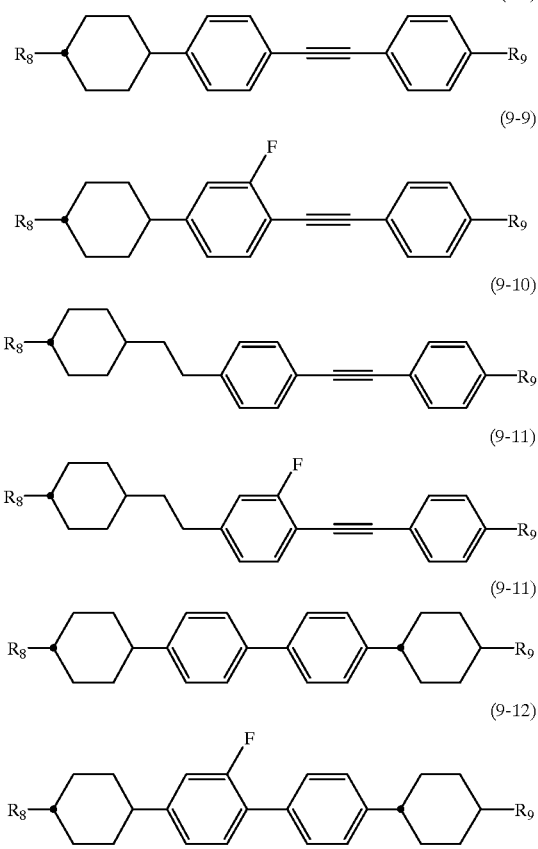

(9-8)
(9-9)
(9-10)
(9-11)
(9-11)
(9-12)

The compounds of general formulae (8) and (9) have negative or a little positive dielectric anisotropy values. The compound of general formula (8) is principally used for decreasing the viscosity or adjusting the dielectric anisotropy value. The compound of general formula (9) is used for broadening the nematic range, for example, for increasing the clearing point of the resulting composition or for adjusting the dielectric anisotropy value.

The compounds of general formulae (5)–(9) is necessary compounds for preparing the liquid crystal compositions for a STN display mode or a TN display mode.

The amount of the compounds of general formulae (5)–(9) is 1–99% by weight, preferably 10–97% by weight, and more preferably 40–95% by weight in case of production of the liquid crystal compositions for the common TN display mode or STN display mode. The compounds of (2)–(4) can be partly used.

The liquid crystal compositions of the present invention are prepared by a method of common use. Usually, each component is dissolved under reduced pressure at a high temperature. However, the compositions can be obtained by mixing the liquid crystals dissolved in organic solvent and distilling away the solvent under reduced pressure.

The liquid crystal materials of the present invention are improved and produce the optimum results by an appropriate additive. Such additives are well known by persons belonging in the field, and particulars are described in literature and the like. Commonly, by inducing a spiral configuration of liquid crystals, necessary twist angles are adjusted. To prevent a rivers twist, chiral dopants and the like are added.

The liquid crystal compositions of the present invention can be used as liquid crystal compositions of the guest-host (G/H) mode by adding dichroic dye such as a merocyanin type, a styryl type, an azo type, an azomethyne type, an azoxy type, a quinophthalon type, an anthraquinone type, and tetrazine type. Otherwise, the compositions can be used for NCAP prepared by micro-capsulation of a nematic liquid crystal or for a liquid crystal composition of a polymer dispersion liquid crystal display device (PDLCD) represented by a polymer network liquid crystal display device (PNLCD), which is prepared by a three-dimensional network polymer in the liquid crystal. In addition, the compositions can be used for an electrically controlled birefringence (ECB) mode or a dynamic scattering (DS) mode.

Such prepared liquid crystal composition containing the compounds of formula (1) of the present invention can be represented in the following examples. When the liquid crystal compositions are exemplified hereinafter, each component is represented by a symbol based on the abbreviation method described in Table 1.

TABLE 1

Representation of compounds by using symbols
R—(A$_1$)—Z$_1$— ... —Z$_n$—(A$_n$)—X

| 1) Left end groups | Symbols | 3) Bonding groups | Symbols |
|---|---|---|---|
| $C_aH_{2a+1}$— | a— | —$CH_2CH_2$— | 2 |
| $C_aH_{2a+1}O$— | aO— | —COO— | E |
| $C_aH_{2a+1}OC_bH_{2b}$— | aOb— | —C≡C— | T |
| $CH_2$=$CHC_aH_{2a}$— | Va— | —CH=CH— | V |
| $C_aH_{2a+1}CH$=$CHC_bH_{2b}$— | aVb— | —$CF_2O$— | CF2O |
| $C_aH_{2a+1}CH$=$CHC_bH_{2b}CH$=$CHC_dH_{2d}$— | aVbVc— | | |

| 2) Ring Structure —(A$_n$)— | Symbols | 4) Right end groups | Symbols |
|---|---|---|---|
| 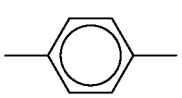 | B | —F | —F |

TABLE 1-continued
Representation of compounds by using symbols
R—(A₁)—Z₁— ... —Zₙ—(Aₙ)—X
| Structure | Symbol | Group | Abbreviation |
|---|---|---|---|
| (ring with F) | B(F) | —Cl | —CL |
| (ring with F) | B(2F) | —CN | —C |
| (ring with 2F, 3F) | B(2F, 3F) | —CF₃ | —CF3 |
| (ring with F, F) | B(F, F) | —OCF₃ | —OCF3 |
| (ring with Cl) | B(CL) | —OCF₂H | —OCF2H |
| (cyclohexane) | H | —C$_w$H$_{2w+1}$ | —w |
| (pyrimidine) | Py | —OC$_w$H$_{2w+1}$ | —Ow |
| (dioxane) | D | —COOCH₃ | —EMe |
| (cyclohexene) | Ch | | |
5) Abbreviation Method
Example 1
3-H2B(F, F)B(F)—F
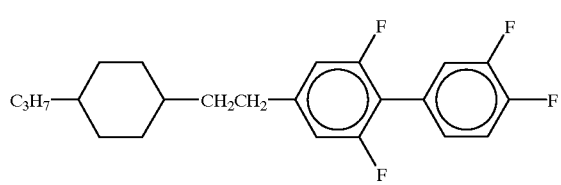

TABLE 1-continued

Representation of compounds by using symbols
R―(A₁)―Z₁― . . . ―Zₙ―(Aₙ)―X

Example 2

3-HB(F)TB-2

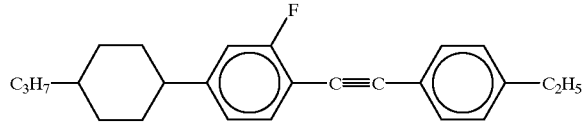

Example 3

1V2-BEB(F, F)—C

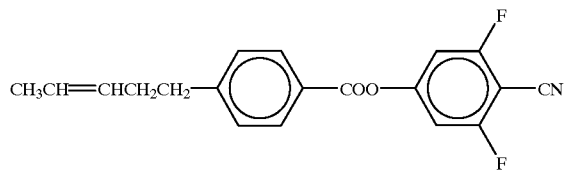

BEST MODE FOR CARRYING OUT THE INVENTION

The compounds and compositions of the present invention are particularly described in the following. However, in each example, C represents a crystal, N represents a nematic phase, I represents an isotropic liquid phase, the unit of phase transition temperature is Celsius temperature (° C.).

EXAMPLE 1

4-(2-(3-fluoro-4-methylphenyl)ethynyl)-1-(2-(4-propylphenyl)ethynyl)benzene (in formula (1), $R_1$ represents a propyl group; $Y_1$ represents a methyl group, $H_1$, $H_2$, $H_3$, $H_4$, $H_5$, $H_6$, $H_7$, $H_8$, $H_9$, $H_{10}$, $H_{11}$ and $H_{12}$, each independently, represent a hydrogen atom, and $H_{10}$ represents a fluorine atom).

The mixture of 2-fluoro-4-iodotoluene (0.05 mol), 3-methyl-3-hydroxy-1-butyne (0.06 mol), tetrakis(triphenylphosphonium) palladium (0) 0.35 g, copper iodide 50 mg, and diethylamine 100 ml was refluxed for 5.5 hours. Diethylamine was distilled away under reduced pressure, the residue was extracted with diethylether, and the extract was washed with water. From the extract, diethylether was distilled away, the residue was purified by column chromatography (elution liquid: heptane-ethyl acetate) to obtain colorless oily 2-fluoro-4-(3-methyl-3-hydroxy-1-butynyl)toluene (0.035 mol).

The mixture of 2-fluoro-4-(3-methyl-3-hydroxy-1-butynyl)toluene (0.035 mol), sodium hydroxide (0.07 mol), and benzene 40 ml was refluxed for 3 hours. After cooling, water 40 ml was added and the mixture was thoroughly stirred. Insoluble materials were filtered away with Celite (trade name of Johns-Manville Company), and the residue was dried over anhydrous magnesium sulfate. The drying agent was separated away, the solvent was carefully distilled away from the solution under reduced pressure, the residue was purified by silica gel chromatography (elution liquid: hexane) and then distilled away the solvent under reduced pressure (boiling point: 100° C., 20 mmHg) to obtain cororless oily 2-fluoro-4-ethynyltoluene (0.014 mol).

The mixture of 2-fluoro-4-ethynyl-toluene (0.014 mol), 4-(2-(4-propylphenyl)ethynyl)-1-bromobenzene (0.014 mol), which was prepared by the method of Japanese Patent Laid-open Publication No. 2-83340, copper iodide (5 mmol), bis(triphenylphosphino)palladium dichloride (2 mmol), and triethylamine 30 ml was heated and refluxed for 11 hours. After cooling, toluene 50 ml and water 50 ml were added and the mixture was well stirred and left to stand, and the organic phase was separated and dried over anhydrous magnesium sulfate.

After the dry agent was separated, the solvent was distilled away under reduced pressure, the residue was purified by column chromatography (elution liquid: heptane/toluene mixture solvent (4/1)) and then recrystallized from heptane/toluene mixture solvent (4/1), and white needle crystals of the title compound (0.10 mol) were obtained. The compound was liquid crystalline and the phase transition points were C-N point: 160.1° C., N-I point: 210.0° C.

The spectrum data supported the configuration.

$^1$H-NMR: δ (ppm): 7.55–7.11 (11H,m), 2.61 (2H,t), 2.29 (3H,d), 1.65 (2H,q), 0.94 (3H,t)

EXAMPLE 2

The following compounds of formula (1) are prepared by the method described in Example 1.

4-(2-(3-fluoro-4-propylphenyl)ethynyl)-1-(2-(4-cyanophenyl)ethynyl)benzene 4-(2-(3-fluoro-4-propylphenyl)ethynyl)-1-(2-(4-pentylphenyl)ethynyl)benzene 4-(2-(3-fluoro-4-propylphenyl)ethynyl)-1-(2-(4-trifluoromethoxyphenyl)ethynyl)benzene 4-(2-(2-chloro-4-propylphenyl)ethynyl)-1-(2-(4-propylphenyl)ethynyl)benzene 4-(2-(2-fluoro-4-pentylphenyl)ethynyl)-1-(2-(4-propylphenyl)ethynyl)benzene 4-(2-(2,3-difluoro-4-propoxyphenyl)ethynyl)-1-(2-(4-pentylphenyl)ethynyl)benzene 2-fluoro-4-(2-(3-fluoro-4-methylphenyl)ethynyl)-1-(2-(4-propylphenyl)ethynyl)benzene C-N point: 156.4° C., N-I point: 187.1° C.

2,3-difluoro-4-(2-(3-fluoro-4-propylphenyl)ethynyl)-1-(2-(4-methylphenyl)ethynyl)benzene

EXAMPLE 3

Liquid crystal composition B1 was prepared from the following compounds.

| | | |
|---|---|---|
| | 4-(4-propylcyclohexyl)benzonitril | 24% |
| | 4-(4-pentylcyclohexyl)benzonitril | 36% |
| | 4-(4-heptylcyclohexyl)benzonitril | 25% |
| | 4-(4-propylphenyl)benzonitril | 15% |

The clearing point of composition $B_1$ was 71.7° C., the dielectric anisotropy value was 11.0, the optical anisotropy value was 0.137, the viscosity at 20° C. was 26.7 mPa.s, and the threshold voltage of the liquid crystal cell having cell thickness 8.7 μm was 1.78V.

4-(2-(3-fluoro-4-methylphenyl)ethynyl)-1-(2-(4-propylphenyl)ethynyl)benzene 5 parts by weight of the present invention obtained in Example 1 was mixed to composition B1 95 parts by weight to prepare liquid crystal composition A1. The clearing point of the composition was 76.6° C., the dielectric anisotropy value was 11.0, the optical anisotropy value was 0.153, the viscosity at 20° C. was 25.4 mPa.s, and the threshold voltage of the liquid crystal cell having cell thickness 8.9 μm was 1.79V. Although the composition was left for 60 days in a freezer at −20° C., crystal deposition was not observed. Extrapolating the particular value of the compound of formula (1) from the mixture, the dielectric anisotropy value was 11.0 and the optical anisotropy value was 0.457.

EXAMPLE 4

To composition B1 90 parts by weight, 2-fluoro-4-(2-(3-fluoro-4-methylphenyl)ethynyl)-1-(2-(4-propylphenyl)ethynyl)benzene 10 parts by weight of the compound obtained in Example 2 was added, and liquid crystal composition A2 was prepared. The clearing point was 80.1° C., the dielectric anisotropy value was 10.8, the optical anisotropy value was 0.167, the viscosity at 20° C. was 25.9 mPa.s, and the threshold voltage of the liquid crystal cell having cell thickness 8.9 μm was 1.82V. Although the composition was left for 60 days in a freezer at −20° C., crystal deposition was not observed. Extrapolating the particular value of the compound of formula (1) from the mixture, the dielectric anisotropy value was 9.0 and the optical anisotropy value was 0.437.

EXAMPLE 5

The following composition was prepared by using the compounds of formula (I).

| | | |
|---|---|---|
| | 3-B(2F)TBTB-5 | 4.0% |
| | 3-B(2F)TBTB-C | 6.0% |
| | 3-HB-C | 30.0% |
| | 5-HB-C | 10.0% |
| | 2-BTB-1 | 10.0% |
| | 3-HH-4 | 10.0% |
| | 3-HHB-1 | 10.0% |
| | 3-HHB-3 | 11.0% |
| | 3-H2BTB-2 | 3.0% |
| | 3-H2BTB-3 | 3.0% |
| | 3-H2BTB-4 | 3.0% |

EXAMPLE 6

The following composition was prepared by using the compounds of formula (I).

| | | |
|---|---|---|
| | 1-B(2F)TB(F)TB-3 | 4.0% |
| | 5-B(F)TBTB-3 | 6.0% |
| | 3O1-BEB(F)-C | 12.0% |
| | 1V2-HB-C | 7.0% |
| | 2-BTB-O1 | 2.8% |
| | 3-BTB-O1 | 2.8% |
| | 4-BTB-O1 | 2.8% |
| | 4-BTB-O2 | 2.8% |
| | 5-BTB-O1 | 2.8% |
| | 2-BTB-1 | 10.0% |
| | 2-BTB-3 | 9.0% |
| | 3-HH-4 | 4.0% |
| | 3-H2BTB-2 | 4.0% |
| | 3-H2BTB-3 | 4.0% |
| | 3-H2BTB-4 | 4.0% |
| | 2-H2BTB-4 | 4.0% |
| | 3-HB(F)TB-2 | 6.0% |
| | 3-HB(F)TB-3 | 7.0% |
| | 3-HB(F)TB-4 | 5.0% |

EXAMPLE 7

The following composition was prepared by using the compounds of formula (I).

| | | |
|---|---|---|
| | 1-B(2F)TB(F)TB-3 | 3.0% |
| | 3-B(2F)TBTB-5 | 6.0% |
| | 5-B(F)TBTB-3 | 6.0% |
| | 3-B(2F)TBTB-C | 6.0% |
| | V2-HB-C | 8.0% |
| | 1V2-HB-C | 8.0% |
| | 1V2-BEB(F,F)-C | 8.0% |
| | 2-BTB-1 | 9.0% |
| | 3-BTB-1 | 8.0% |
| | 2-BTB-3 | 8.0% |
| | 3-HH-4 | 8.0% |
| | 2-HH-5 | 6.0% |
| | 1O1-HH-5 | 5.0% |
| | 3-HH-EMe | 3.0% |
| | 3-H2BTB-2 | 4.0% |
| | 3-H2BTB-3 | 4.0% |

EXAMPLE 8

The following composition was prepared by using the compounds of formula (I).

| | | |
|---|---|---|
| | 3-B(2F)TBTB-5 | 6.0% |
| | 5-B(F)TBTB-3 | 6.0% |
| | 3-B(2F)TBTB-OCF3 | 3.0% |
| | 2-BB-C | 8.0% |
| | 4-BB-C | 6.0% |
| | 2-HB-C | 8.0% |
| | 3-HB-C | 11.0% |
| | 1O1-HB-C | 4.0% |
| | 3-HHB-F | 5.0% |
| | 2-HHB-C | 4.0% |
| | 3-HHB-C | 6.0% |
| | 5-PyB-F | 6.0% |
| | 3-PyBB-F | 6.0% |
| | 2-HHB-1 | 6.0% |
| | 3-HHB-3 | 10.0% |
| | 3-HHB-O1 | 5.0% |

EXAMPLE 9

The following composition was prepared by using the compounds of formula (I).

| | |
|---|---|
| 1-B(2F)TBTB-3 | 3.0% |
| 3-B(2F)TBTB-5 | 5.0% |
| 2-HB(F)-C | 12.0% |
| 2-HHB(F)-C | 5.0% |
| 3-HHB(F)-C | 5.0% |
| 3-HB-O2 | 6.0% |
| 2-BTB-O1 | 6.8% |
| 3-BTB-O1 | 6.8% |
| 4-BTB-O1 | 6.8% |
| 4-BTB-O2 | 6.8% |
| 5-BTB-O1 | 6.8% |
| 3-HB(F)TB-2 | 6.0% |
| 3-HB(F)TB-3 | 6.0% |
| 3-HB(F)TB-4 | 6.0% |
| 2-PyBH-3 | 4.0% |
| 3-PyBH-3 | 4.0% |
| 3-PyBB-2 | 4.0% |

EXAMPLE 10

The following composition was prepared by using the compounds of formula (I).

| | |
|---|---|
| 3-B(2F)TBTB-5 | 5.0% |
| 5-B(F)TBTB-3 | 5.0% |
| 5-BB-C | 7.0% |
| 3-HHB-F | 4.0% |
| 3-HBEB-F | 2.0% |
| 5-HHEB-F | 3.0% |
| 3-HB-O2 | 10.0% |
| 3-HB-O4 | 12.0% |
| 3-PyB-4 | 3.1% |
| 4-PyB-4 | 3.1% |
| 6-PyB-4 | 3.2% |
| 3-PyB-4 | 3.2% |
| 4-PyB-5 | 3.2% |
| 6-PyB-5 | 3.2% |
| 6-PyB-O5 | 4.0% |
| 6-PyB-O6 | 4.0% |
| 6-PyB-O7 | 4.0% |
| 6-PyB-O8 | 4.0% |
| 2-HHB-1 | 3.0% |
| 3-HHB-1 | 8.0% |
| 3-HEBEB-1 | 3.0% |
| 3-HEBEB-F | 3.0% |

EXAMPLE 11

The following composition was prepared by using the compounds of formula (I).

| | |
|---|---|
| 1-B(2F)TBTB-3 | 2.0% |
| 1-B(2F)TB(F)TB-3 | 3.0% |
| 3-DB-C | 10.0% |
| 4-DB-C | 10.0% |
| 2-BEB-C | 7.0% |
| 3-BEB-C | 4.0% |
| 5-HEB-F | 5.0% |
| 3-HHEBB-C | 3.0% |
| 3-HBEBB-C | 3.0% |
| 5-HBEBB-C | 3.0% |
| 3-PyB(F)-F | 6.0% |
| 3-HEB-O4 | 6.0% |
| 4-HEB-O2 | 6.0% |
| 5-HEB-O1 | 7.0% |
| 3-HEB-O2 | 7.0% |
| 5-HEB-1 | 4.0% |
| 4-HEB-4 | 5.0% |
| 1O-BEB-2 | 3.0% |
| 3-HHB-1 | 6.0% |

EXAMPLE 12

The following composition was prepared by using the compounds of formula (I).

| | |
|---|---|
| 1-B(2F)TBTB-3 | 3.0% |
| 3-B(2F)TBTB-5 | 6.0% |
| 5-B(F)TBTB-3 | 5.0% |
| 7-HB(F,F)-F | 4.0% |
| 3-H2HB(F,F)-F | 10.0% |
| 4-H2HB(F,F)-F | 10.0% |
| 3-HHB(F,F)-F | 10.0% |
| 4-HHB(F,F)-F | 10.0% |
| 3-HH2B(F,F)-F | 10.0% |
| 5-HH2B(F,F)-F | 10.0% |
| 3-HBB(F,F)-F | 12.0% |
| 5-HBB(F,F)-F | 6.0% |
| 3-HHBB(F,F)-F | 2.0% |
| 2-HH2BB(F,F)-F | 2.0% |

EXAMPLE 13

The following composition was prepared by using the compounds of formula (I).

| | |
|---|---|
| 1-B(2F)TB(F)TB-3 | 3.0% |
| 5-B(F)TBTB-3 | 5.0% |
| 7-HB(F)-F | 13.0% |
| 2-HHB(F)-F | 12.0% |
| 3-HHB(F)-F | 12.0% |
| 5-HHB(F)-F | 12.0% |
| 2-H2HB(F)-F | 6.0% |
| 3-H2HB(F)-F | 3.0% |
| 5-H2HB(F)-F | 6.0% |
| 2-HBB(F)-F | 7.0% |
| 3-HBB(F)-F | 7.0% |
| 5-HBB(F)-F | 14.0% |

EXAMPLE 14

The following composition was prepared by using the compounds of formula (I).

| | |
|---|---|
| 3-B(2F)TBTB-5 | 5.0% |
| 3-B(2F)TBTB-OCF3 | 5.0% |
| 5-HB-CL | 6.0% |
| 7-HB(F,F)-F | 8.0% |
| 2-HBB(F)-F | 7.0% |
| 3-HBB(F)-F | 7.0% |
| 5-HBB(F)-F | 14.0% |
| 5-H2BB(F)-F | 5.0% |
| 2-HHB-CL | 5.0% |
| 4-HHB-CL | 8.0% |
| 5-HHB-CL | 5.0% |
| 3-HBB(F,F)-F | 11.0% |
| 5-HBB(F,F)-F | 6.0% |

-continued

| | |
|---|---|
| 3-HB(F)VB-2 | 4.0% |
| 3-HB(F)VB-3 | 4.0% |

EXAMPLE 15

The following composition was prepared by using the compounds of formula (I).

| | |
|---|---|
| 1-B(2F)TB(F)TB-3 | 3.0% |
| 3-B(2F)TBTB-5 | 4.0% |
| 5-B(F)TBTB-3 | 5.0% |
| 5-H2B(F)-F | 5.0% |
| 2-HHB(F)-F | 8.0% |
| 3-HHB(F)-F | 8.0% |
| 5-HHB(F)-F | 8.0% |
| 3-HHB(F,F)-F | 7.0% |
| 5-HHB(F,F)-F | 7.0% |
| 3-H2HB(F,F)-F | 5.0% |
| 4-H2HB(F,F)-F | 5.0% |
| 5-H2HB(F,F)-F | 5.0% |
| 3-HH2B(F,F)-F | 10.0% |
| 5-HH2B(F,F)-F | 6.0% |
| 2-HBB-F | 5.0% |
| 5-HBB-F | 3.0% |
| 3-HHB-1 | 6.0% |

EXAMPLE 16

The following composition was prepared by using the compounds of formula (I).

| | |
|---|---|
| 1-B(2F)TB(F)TB-3 | 3.0% |
| 3-B(CL)TBTB-3 | 4.0% |
| 3O-B(2F,3F)TBTB-3 | 4.0% |
| 2-HHB(F)-F | 8.0% |
| 3-HHB(F)-F | 8.0% |
| 5-HHB(F)-F | 8.0% |
| 2-HBB(F)-F | 4.0% |
| 3-HBB(F)-F | 4.0% |
| 5-HBB(F)-F | 8.0% |
| 5-HHB(F,F)-F | 6.0% |
| 3-HH2B(F,F)-F | 8.0% |
| 5-HH2B(F,F)-F | 8.0% |
| 5-H2BB(F,F)-F | 5.0% |
| 3-HBEB(F,F)-F | 3.0% |
| 3-HHEB(F,F)-F | 6.0% |
| 5-HHEB(F,F)-F | 3.0% |
| 5-HHEBB-F | 2.0% |
| 3-HB-O2 | 5.0% |
| 1O1-HBBH-3 | 3.0% |

EXAMPLE 17

The following composition was prepared by using the compounds of formula (I).

| | |
|---|---|
| 3-B(2F)TBTB-OCF3 | 6.0% |
| 3-B(2F)TB(2F,3F)TB-1 | 4.0% |
| 7-HB-F | 7.0% |
| 3-HHB-OCF3 | 10.0% |
| 5-HHB-OCF3 | 8.0% |
| 3-H2HB-OCF3 | 5.0% |
| 5-H2HB-OCF3 | 5.0% |
| 2-HHB(F)-F | 4.0% |

-continued

| | |
|---|---|
| 3-HHB(F)-F | 4.0% |
| 5-HHB(F)-F | 4.0% |
| 5-H2BB(F)-F | 6.0% |
| 3-H2HB(F,F)-F | 5.0% |
| 5-H2HB(F,F)-F | 5.0% |
| 3-HHB(F,F)-F | 8.0% |
| 3-HH2B(F,F)-F | 8.0% |
| 4-HH2B(F,F)-F | 7.0% |
| 5-HB(F)BH-3 | 4.0% |

EXAMPLE 18

The following composition was prepared by using the compounds of formula (I).

| | |
|---|---|
| 3-B(CL)TBTB-3 | 5.0% |
| 3O-B(2F,3F)TBTB-3 | 5.0% |
| V-HB-C | 10.0% |
| 1V-HB-C | 8.0% |
| 5-BB-C | 7.0% |
| 2-HB(F)-C | 5.0% |
| 4-BB-3 | 3.0% |
| 3-H2B-O | 5.0% |
| 5-H2B-O2 | 6.0% |
| 3-BEB-C | 5.0% |
| 5-HEB-O1 | 4.0% |
| 5-HEB-O3 | 4.0% |
| 5-BBB-C | 3.0% |
| 4-BPyB-C | 8.0% |
| 4-BPyB-5 | 8.0% |
| 5-HB2B-4 | 3.0% |
| 5-HBB2B-3 | 3.0% |
| 1V-HH-1O1 | 5.0% |
| 1V2-HBB-3 | 3.0% |

EXAMPLE 19

The following composition was prepared by using the compounds of formula (I).

| | |
|---|---|
| 3O-B(2F,3F)TBTB-3 | 5.0% |
| 3B(2F)TB(2F,3F)TB-1 | 5.0% |
| V2-HB-C | 9.0% |
| 1V2-HB-C | 9.0% |
| 3-HB-C | 14.0% |
| 1O1-HB-C | 8.0% |
| 2O1-HB-C | 4.0% |
| 2-HHB-C | 5.0% |
| 3-HHB-C | 5.0% |
| V2-HH-3 | 4.0% |
| V-HH-4 | 6.0% |
| 1O1-HH-5 | 5.0% |
| 2-BTB-O1 | 7.0% |
| V-HHB-1 | 5.0% |
| V-HBB-2 | 5.0% |
| 1V2-HBB-2 | 4.0% |

Industrial Applicability

The compounds of the present invention is new liquid crystalline compounds having high optical anisotropy and low viscosity, and have excellent compatibility with the other liquid crystalline compounds. The new liquid crystal compositions constituted from the above compounds have high optical anisotropy and relatively low viscosity.

The compounds of the present invention have more excellent compatibility with the other liquid crystal compounds than that of compounds having well-known similar configuration, and the compounds are very useful for preparing a stable nematic liquid crystal mixture.

When 15% by weight of 4-(2-(4-pentylphenyl)ethynyl)-1-(2-(4-propylphenyl)ethynyl)benzene, which is disclosed in Japanese Laid-open Publication No. 2-83340, or 4-(2-(4-pentylphenyl)ethynyl)-2-fluoro-1-(2-(4-propylphenyl)ethynyl)benzene, which is disclosed in EP581272, was mixed with liquid crystal composition B1 in the above-mentioned examples, phase separation (deposition of smectic phase) was observed within 30 days or one day, respectively. On the other hand, when 4-(2-(3-fluoro-4-methylphenyl)ethynyl)-1-(2-(4-propylphenyl)ethynyl)benzene of the present invention was added to the same liquid crystal mixture, the nematic phase was maintained for 60 days.

What is claimed is:

1. A liquid crystalline acetylene derivative represented by general formula (1):

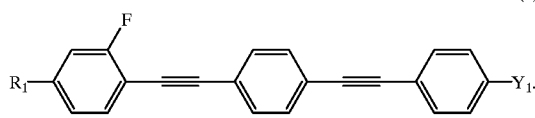

(1)

wherein $R_1$ represents an alkyl group of 1–5 carbon atoms; and $Y_1$ is replaced by $R_1$, a fluorine atom, a chlorine atom, a bromine atom, an iodine atom or a cyano group.

2. A liquid crystal composition comprising at least one liquid crystalline acetylene derivative according to claim 1 as a first component, and at least one compound selected from the group consisting of compounds represented by general formulas (2), (3) and (4) as a second component,

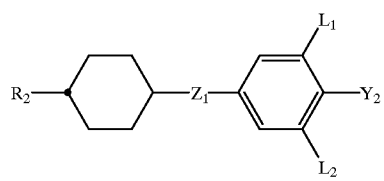

(2)

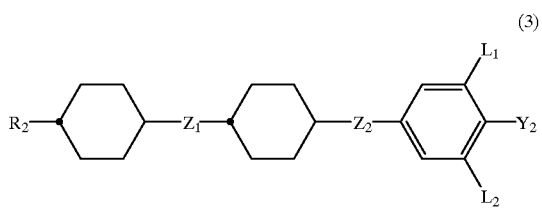

(3)

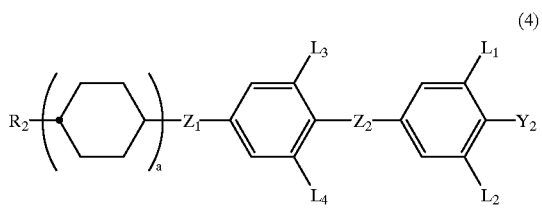

(4)

wherein $R_2$ represents an alkyl group of 1–10 carbon atoms; $Y_2$ represents a fluorine atom, a chlorine atom, $OCF_3$, $OCHF_2$, $CF_3$, $CHF_2$ or $CH_2F$; $L_1$, $L_2$, $L_3$, and $L_4$, each independently, represent a hydrogen atom or a fluorine atom; $Z_1$ and $Z_2$, each independently, represent $—CH_2CH_2—$, $—CH=CH—$ or a covalent bond; and a representing 1 or 2.

3. A liquid crystal composition comprising at least one liquid crystalline acetylene derivative according to claim 1 as a first component, and at least one compound selected from the group consisting of compounds represented by general formulas (5), (6), (7), (8) and (9) as a second component:

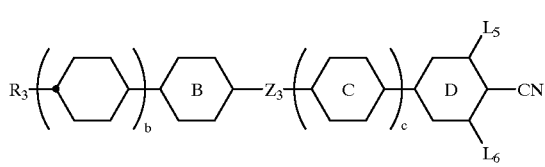

(5)

wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cyclohexylene or 1,4-phenylene; $Z_3$ represents $—CH_2CH_2—$, $—COO—$ or a covalent bond; $L_5$ and $L_6$, each independently, represent a hydrogen atom or a fluorine atom, b and c, each independently, represent 0 or 1,

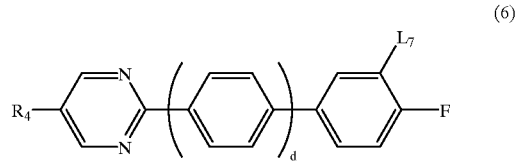

(6)

wherein $R_4$ represents an alkyl group of 1–10 carbon atoms; $L_7$ represents a hydrogen atom or a fluorine atom; and d represents 0 or 1,

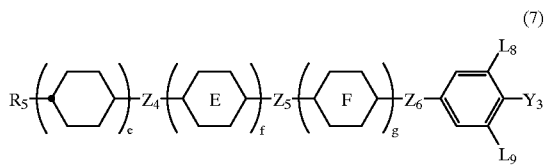

(7)

wherein $R_5$ represents an alkyl group of 1–10 carbon atoms; six-membered ring E and six-membered ring F represent, each independently, trans-1,4-cyclohexylene or 1,4-phenylene; $Z_4$ and $Z_5$, each independently, represent $—COO—$ or a covalent bond; $Z_6$ represents $—COO—$ or $—C\equiv C—$; $L_8$ and $L_9$, each independently, represent a hydrogen atom or a fluorine atom; $Y_3$ represents a fluorine atom, $OCF_3$, $OCHF_2$, $CF_3$, $CHF_2$ or $CH_2F$; e, f and g, each independently, represent 0 or 1; and e, f and g are not 0 at the same time; when e is 0, $Z_4$ is a covalent bond; when f or g is 0, $Z_5$ is a covalent bond; and when f and g are 0, $Z_4$ is also a covalent bond, (8)

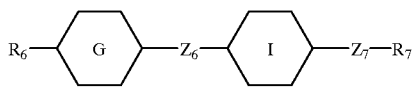

wherein $R_6$ and $R_7$, each independently, represent an alkyl group of 1–10 carbon atoms or an alkenyl group of 2–10 carbon atoms, in which one or more not-adjacent methylene groups may be replaced by an oxygen atom; six-membered ring G represents trans-1,4-cydohexylene, 1,4-phenylene or pyrimidine-2,5-diyl; six-membered ring I represents trans-1,4-cyclohexylene or 1,4-phenylene; $Z_6$ represents —C≡C—, —COO—, —CH$_2$CH$_2$—, —CH=CH—C≡C— or a covalent bond; and $Z_7$ represents —COO— or a covalent bond, (9)

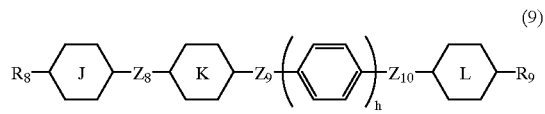

wherein $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring J represents trans-1,4-cyclohexylene, 1,4-phenylene or pyrimidine-2,5-diyl; six-membered ring K represents trans-1,4-cyclohexylene, pyrimidine-2,5-diyl or 1,4-phenylene, and in which one or more hydrogen atoms may be substituted by fluorine atoms at the side; six-membered ring L represents trans-1,4-cyclohexylene or 1,4-phenylene; $Z_8$ and $Z_{10}$, each independently, represent —COO—, —CH$_2$CH$_2$— or a covalent bond; $Z_9$ represents —CH=CH—, —C≡C—, —COO— or a covalent bond, and h represents 0 or 1; and when h is 0, at least any one of $Z_9$ and $Z_{10}$ are a covalent bond.

4. A liquid crystal composition comprising at least one liquid crystalline acetylene derivative according to claim 1 as a first component, and comprising at least one compound selected from the group consisting of compounds represented by general formulas (2), (3) and (4) as a second component:

(2)

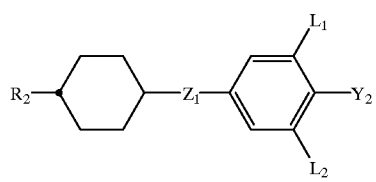

(3)

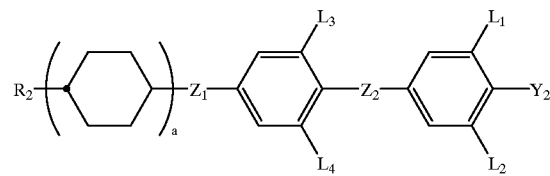

(4)

wherein $R_2$ represents an alkyl group of 1–10 carbon atoms; $Y_2$ represents a fluorine atom, a chlorine atom, OCF$_3$, OCHF$_2$, CF$_3$, CHF$_2$ or CH$_2$F; $L_1$, $L_2$, $L_3$ and $L_4$, each independently, represent a hydrogen atom or a fluorine atom; $Z_1$ and $Z_2$, each independently, represent —CH$_2$CH$_2$—, —CH=CH— or a covalent bond; and a represents 1 or 2, and at least one compound selected from the group consisting of compounds represented by general formulas (5), (6), (7), (8) and (9) as a third component:

(5)

wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cyclohexylene or 1,4-phenylene; $Z_3$ represents —CH$_2$CH$_2$—, —COO— or a covalent bond; $L_5$ and $L_6$, each independently, represent a hydrogen atom or a fluorine atom, b and c, each independently, represent 0 or 1, (6)

wherein $R_4$ represents an alkyl group of 1–10 carbon atoms, $L_7$ represents a hydrogen atom or a fluorine atom, and d represents 0 or 1, (7)

wherein $R_5$ represents an alkyl group of 1–10 carbon atoms; six-membered ring E and six-membered ring F represent, each independently, trans-1,4-cyclohexylene or 1,4-phenylene; $Z_4$ and $Z_5$, each independently, represent —COO— or a covalent bond; $Z_6$ represents —COO— or —C≡C—; $L_8$ and $L_9$, each independently, represent a hydrogen atom or a fluorine atom; $Y_3$ represents a fluorine atom, $OCF_3$, $OCHF_2$, $CF_3$, $CHF_2$ or $CH_2F$; e, f and g, each independently, represent 0 or 1; and e, f and g are not 0 at the same time; when e is 0, $Z_4$ is a covalent bond; when f or g is 0, $Z_5$ is a covalent bond; and when f and g are 0, $Z_4$ is also a covalent bond, (8)

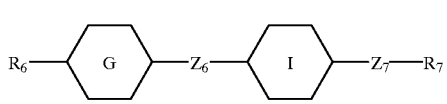

wherein $R_6$ and $R_7$, each independently, represent an alkyl group of 1–10 carbon atoms or an alkenyl group of 2–10 carbon atoms, in which one or more not-adjacent methylene groups may be replaced by an oxygen atom; six-membered ring G represents trans-1,4-cyclohexylene, 1,4-phenylene or pyrimidine-2,5-diyl; six-membered ring I represents trans-1,4-cyclohexylene or 1,4-phenylene; $Z_6$ represents —C≡C—, —COO—, —$CH_2CH_2$—, —CH=CH—C≡C— or a covalent bond; and $Z_7$ represents —COO— or a covalent bond, (9)

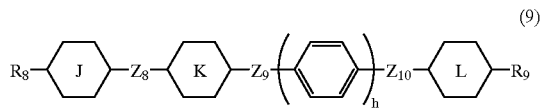

wherein $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring J represents trans-1,4-cyclohexylene, 1,4-phenylene or pyrimidine-2,5-diyl; six-membered ring K represents trans-1,4-cyclohexylene, pyrimidine-2,5-diyl or 1,4-phenylene, in which one or more hydrogen atoms may be substituted by fluorine atoms at the side; six-membered ring L represents trans-1,4-cyclohexylene or 1,4-phenylene; $Z_8$ and $Z_{10}$, each independently, represent —COO—, —$CH_2CH_2$— or a covalent bond; $Z_9$ represents —CH=CH—, —C≡C—, —COO— or a covalent bond, and h represents 0 or 1; and when h is 0, at least any one of $Z_9$ and $Z_{10}$ is a covalent bond.

5. A liquid crystalline acetylene derivative represented by the following formula:

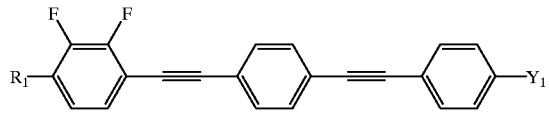

wherein $R_1$ represents an alkyl group of 1–5 carbon atoms; and $Y_1$ is replaced by $R_1$, a fluorine atom, a chlorine atom, a bromine atom, an iodine atom or a cyano group.

6. A liquid crystal composition comprising at least one liquid crystalline acetylene derivative according to claim 5 as a first component, and at least one compound selected from the group consisting of compounds represented by general formulas (2), (3) and (4) as a second component, (2)

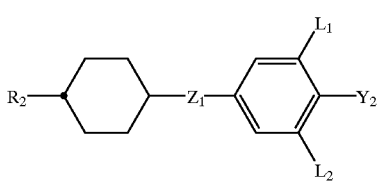

(3)

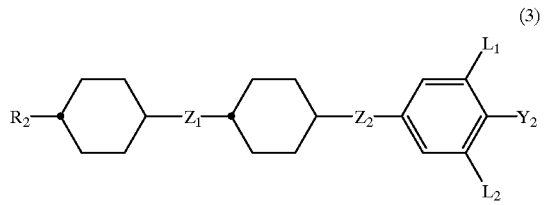

(4)

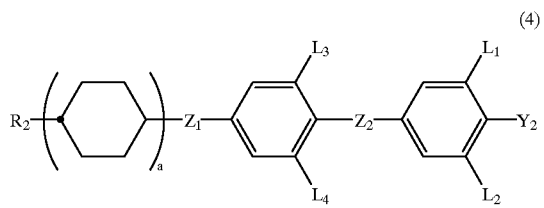

wherein $R_2$ represents an alkyl group of 1–10 carbon atoms; $Y_2$ represents a fluorine atom, a chlorine atom, $OCF_3$, $OCHF_3$, $CF_3$, $CHF_2$ or $CH_2F$; $L_1$, $L_2$, $L_3$, and $L_4$, each independently, represent a hydrogen atom or a fluorine atom; $Z_1$ and $Z_2$, each independently, represent —$CH_2CH_2$—, —CH=CH— or a covalent bond; and a representing 1 or 2.

7. A liquid crystal composition comprising at least one liquid crystalline acetylene derivative according to claim 5 as a first component, and at least one compound selected from the group consisting of compounds represented by general formulas (5), (6), (7), (8) and (9) as a second component:

(5)

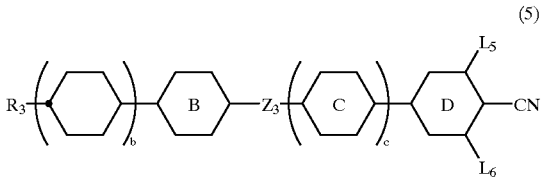

wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cyclohexylene or 1,4-phenylene; $Z_3$ represents —$CH_2CH_2$—, —COO— or a covalent bond; $L_5$ and $L_6$, each independently, represent a hydrogen atom or a fluorine atom, b and c, each independently, represent 0 or 1, (6)

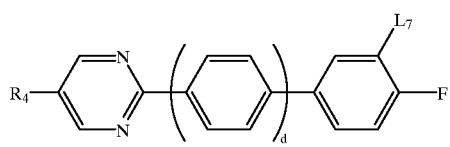

wherein $R_4$ represents an alkyl group of 1–10 carbon atoms; $L_7$ represents a hydrogen atom or a fluorine atom; and d represents 0 or 1, (7)

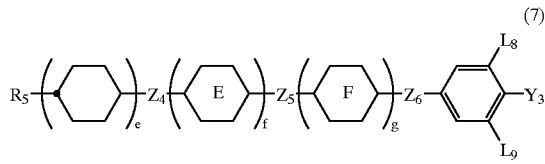

wherein $R_5$ represents an alkyl group of 1–10 carbon atoms; six-membered ring E and six-membered ring F represent, each independently, trans-1,4-cyclohexylene or 1,4-phenylene; $Z_4$ and $Z_5$, each independently, represent —COO— or a covalent bond; $Z_6$ represents —COO— or —C≡C—; $L_8$ and $L_9$, each independently, represent a hydrogen atom or a fluorine atom; $Y_3$ represents a fluorine atom, $OCF_3$, $OCHF_2$, $CF_3$, $CHF_2$ or $CH_2F$; e, f and g, each independently, represent 0 or 1; and e, f and g are not 0 at the same time; when e is 0, $Z_4$ is a covalent bond; when f or g is 0, $Z_5$ is a covalent bond; and when f and g are 0, $Z_4$ is also a covalent bond, (8)

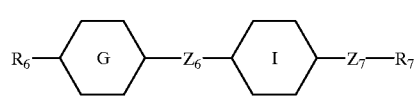

wherein $R_6$ and $R_7$, each independently, represent an alkyl group of 1–10 carbon atoms or an alkenyl group of 2–10 carbon atoms, in which one or more not-adjacent methylene groups may be replaced by an oxygen atom; six-membered ring G represents trans-1,4-cyclohexylene, 1,4-phenylene or pyrimidine-2,5-diyl; six-membered ring I represents trans-1,4-cyclohexylene or 1,4-phenylene; $Z_6$ represents —C≡C—, —COO—, —CH₂CH₂—, —CH=CH—C≡C— or a covalent bond; and $Z_7$ represents —COO— or a covalent bond, (9)

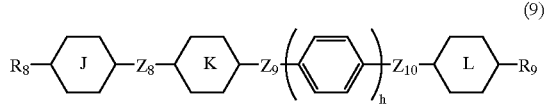

wherein $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring J represents trans-1,4-cyclohexylene, 1,4-phenylene or pyrimidine-2,5-diyl; six-membered ring K represents trans-1,4-cyclohexylene, pyrimidine-2,5-diyl or 1,4-phenylene, and in which one or more hydrogen atoms may be substituted by fluorine atoms at the side; six-membered ring L represents trans-1,4-cyclohexylene or 1,4-phenylene; $Z_8$ and $Z_{10}$, each independently, represent —COO—, —CH₂CH₂— or a covalent bond; $Z_9$ represents —CH=CH—, —C≡C—, —COO— or a covalent bond, and h represents 0 or 1; and when h is 0, at least any one of $Z_9$ and $Z_{10}$ are a covalent bond.

8. A liquid crystal composition comprising at least one liquid crystalline acetylene derivative according to claim 5 as a first component, and comprising at least one compound selected from the group consisting of compounds represented by general formulas (2), (3) and (4) as a second component:

(2)

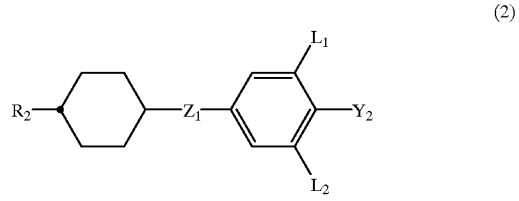

(3)

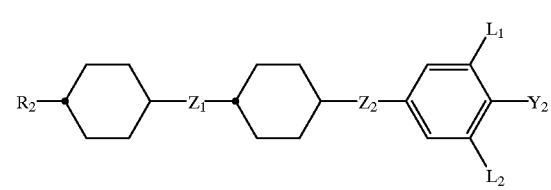

(4)

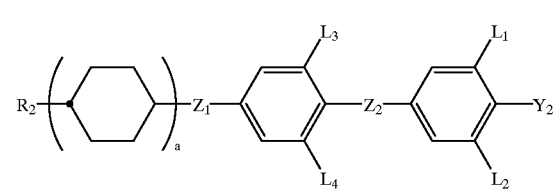

wherein $R_2$ represents an alkyl group of 1–10 carbon atoms; $Y_2$ represents a fluorine atom, a chlorine atom, $OCF_3$, $OCHF_2$, $CF_3$, $CHF_2$ or $CH_2F$; $L_1$, $L_2$, $L_3$ and $L_4$, each independently, represent a hydrogen atom or a fluorine atom; $Z_1$ and $Z_2$, each independently, represent —CH₂CH₂—, —CH=CH— or a covalent bond; and a represents 1 or 2, and at least one compound selected from the group consisting of compounds represented by general formulas (5), (6), (7), (8) and (9) as a (5)

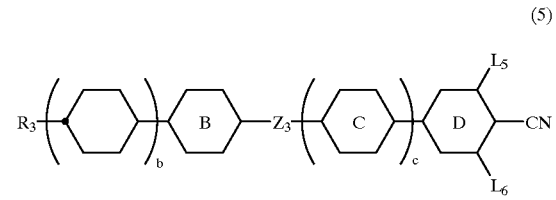

wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cyclohexylene or 1,4-phenylene; $Z_3$ represents —CH$_2$CH$_2$—, —COO— or a covalent bond; $L_5$ and $L_6$, each independently, represent a hydrogen atom or a fluorine atom, b and c, each independently, represent 0 or 1, (6)

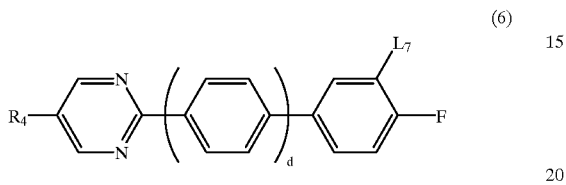

wherein $R_4$ represents an alkyl group of 1–10 carbon atoms, $L_7$ represents a hydrogen atom or a fluorine atom, and d represents 0 or 1, (7)

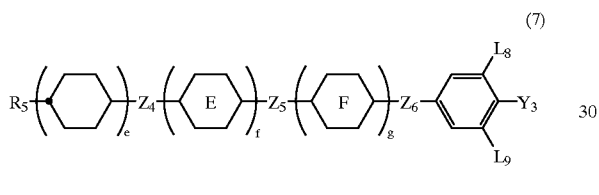

wherein $R_5$ represents an alkyl group of 1–10 carbon atoms; six-membered ring E and six-membered ring F represent, each independently, trans-1,4-cyclohexylene or 1,4-phenylene; $Z_4$ and $Z_5$, each independently, represent —COO— or a covalent bond; $Z_6$ represents —COO— or —C≡C—; $L_8$ and $L_9$, each independently, represent a hydrogen atom or a fluorine atom; $Y_3$ represents a fluorine atom, OCF$_3$, OCHF$_2$, CF$_3$, CHF$_2$ or CH$_2$F; e, f and g, each independently, represent 0 or 1; and e, f and g are not 0 at the same time; when e is 0, $Z_4$ is a covalent bond; when f or g is 0, $Z_5$ is a covalent bond; and when f and g are 0, $Z_4$ is also a covalent bond, (8)

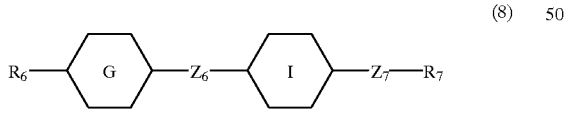

wherein $R_6$ and $R_7$, each independently, represent an alkyl group of 1–10 carbon atoms or an alkenyl group of 2–10 carbon atoms, in which one or more not-adjacent methylene groups may be replaced by an oxygen atom; six-membered ring G represents trans-1,4-cydohexylene, 1,4-phenylene or pyrimidine-2,5-diyl; six-membered ring I represents trans-1,4-cyclohexylene or 1,4-phenylene; $Z_6$ represents —C≡C—, —COO—, —CH$_2$CH$_2$—, —CH=CH—C≡C— or a covalent bond; and $Z_7$ represents —COO— or a covalent bond, (9)

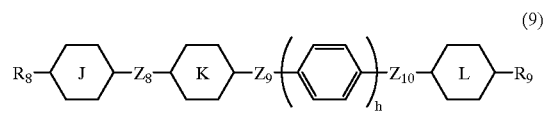

wherein $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring J represents trans-1,4-cyclohexylene, 1,4-phenylene or pyrimidine-2,5-diyl; six-membered ring K represents trans-1,4-cyclohexylene, pyrimidine-2,5-diyl or 1,4-phenylene, in which one or more hydrogen atoms may be substituted by fluorine atoms at the side; six-membered ring L represents trans-1,4-cyclohexylene or 1,4-phenylene; $Z_8$ and $Z_{10}$, each independently, represent —COO—, —CH$_2$CH$_2$— or a covalent bond; $Z_9$ represents —CH=CH—, —C≡C—, —COO— or a covalent bond, and h represents 0 or 1; and when h is 0, at least any one of $Z_9$ and $Z_{10}$ is a covalent bond.

9. A liquid crystalline acetylene derivative represented by the following formula:

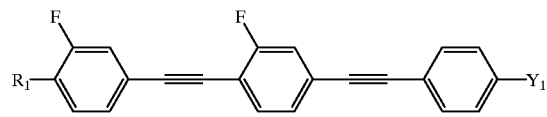

wherein $R_1$ represents an alkyl group of 1–5 carbon atoms; and $Y_1$ is replaced by $R_1$, a fluorine atom, a chlorine atom, a bromine atom, an iodine atom or a cyano group.

10. A liquid crystal composition comprising at least one liquid crystalline acetylene derivative according to claim 9 as a first component, and at least one compound selected from the group consisting of compounds represented by general formulas (2), (3) and (4) as a second component, (2)

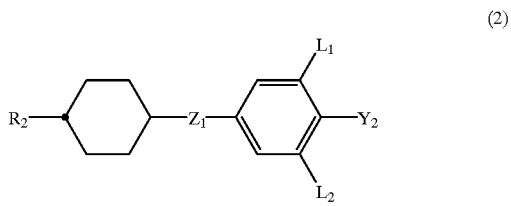

(4)

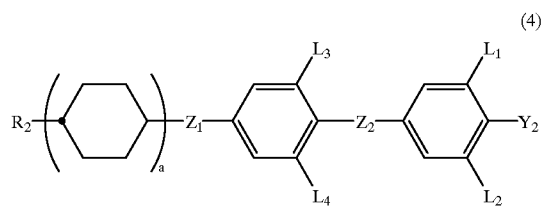

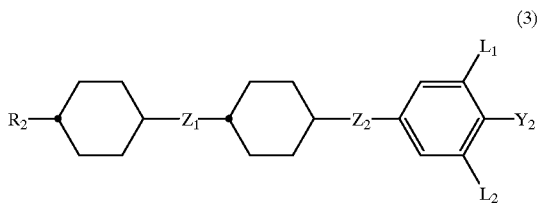

(3)

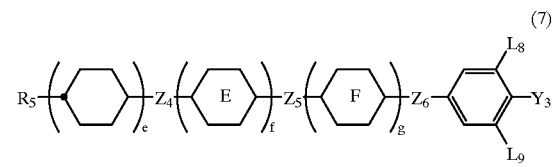

(7)

wherein $R_5$ represents an alkyl group of 1–10 carbon atoms; six-membered ring E and six-membered ring F represent, each independently, trans-1,4-cyclohexylene or 1,4-phenylene; $Z_4$ and $Z_5$, each independently, represent —COO— or a covalent bond; $Z_6$ represents —COO— or —C≡C—; $L_8$ and $L_9$, each independently, represent a hydrogen atom or a fluorine atom; $Y_3$ represents a fluorine atom, $OCF_3$, $OCHF_2$, $CF_3$, $CHF_2$ or $CH_2F$; e, f and g, each independently, represent 0 or 1; and e, f and g are not 0 at the same time; when e is 0, $Z_4$ is a covalent bond; when f or g is 0, $Z_5$ is a covalent bond; and when f and g are 0, $Z_4$ is also a covalent bond, wherein $R_2$ represents an alkyl group of 1–10 carbon atoms; $Y_2$ represents a fluorine atom, a chlorine atom, $OCF_3$, $OCHF_3$, $CF_3$, $CHF_2$ or $CH_2F$; $L_1$, $L_2$, $L_3$, and $L_4$, each independently, represent a hydrogen atom or a fluorine atom; $Z_1$ and $Z_2$, each independently, represent —$CH_2CH_2$—, —CH=CH— or a covalent bond; and a representing 1 or 2.

11. A liquid crystal composition comprising at least one liquid crystalline acetylene derivative according to claim 9 as a first component, and at least one compound selected from the group consisting of compounds represented by general formulas (5), (6), (7), (8) and (9) as a second component:

(5)

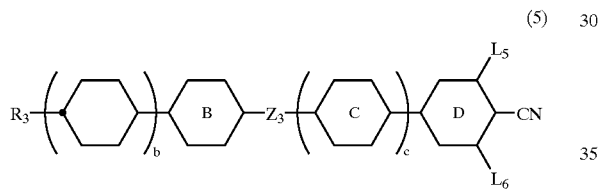

(8)

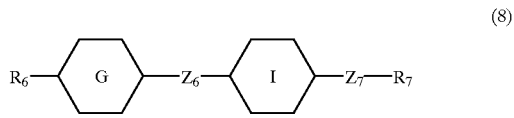

wherein $R_6$ and $R_7$, each independently, represent an alkyl group of 1–10 carbon atoms or an alkenyl group of 2–10 carbon atoms, in which one or more not-adjacent methylene groups may be replaced by an oxygen atom; six-membered ring G represents trans-1,4-cyclohexylene, 1,4-phenylene or pyrimidine-2,5-diyl; six-membered ring I represents trans-1,4-cyclohexylene or 1,4-phenylene; $Z_6$ represents —C≡C—, —COO—, —$CH_2CH_2$—, —CH=CH—C≡C— or a covalent bond; and $Z_7$ represents —COO— or a covalent bond, wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cyclohexylene or 1,4-phenylene; $Z_3$ represents —$CH_2CH_2$—, —COO— or a covalent bond; $L_5$ and $L_6$, each independently, represent a hydrogen atom or a fluorine atom, b and c, each independently, represent 0 or 1, (9)

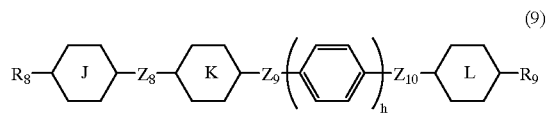

wherein $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring J represents trans-1,4-cyclohexylene, 1,4-phenylene or pyrimidine-2,5-diyl; six-membered ring K represents trans-1,4-cyclohexylene, pyrimidine-2,5-diyl or 1,4-phenylene, and in which one or more hydrogen atoms may be substituted by fluorine atoms at the side; six-membered ring L represents trans-1,4-cyclohexylene or 1,4-phenylene; $Z_8$ and $Z_{10}$, each independently, represent —COO—, —$CH_2CH_2$— or a covalent bond; $Z_9$ represents —CH=CH—, —C≡C—, —COO— or a covalent bond, and h represents 0 or 1; and when h is 0, at least any one of $Z_9$ and $Z_{10}$ are a covalent bond.

(6)

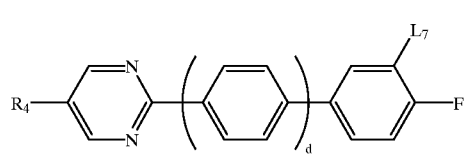

wherein $R_4$ represents an alkyl group of 1–10 carbon atoms; $L_7$ represents a hydrogen atom or a fluorine atom; and d represents 0 or 1, 12. A liquid crystal composition comprising at least one liquid crystalline acetylene derivative according to claim 9 as a first component, and comprising at least one compound selected from the group consisting of compounds represented by general formulas (2), (3) and (4) as a second component:

(2)

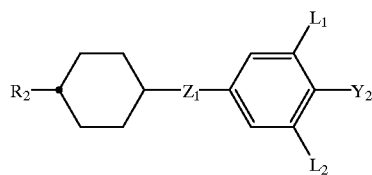

(3)

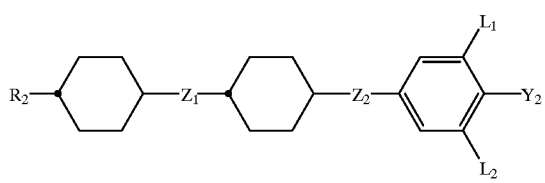

(4)

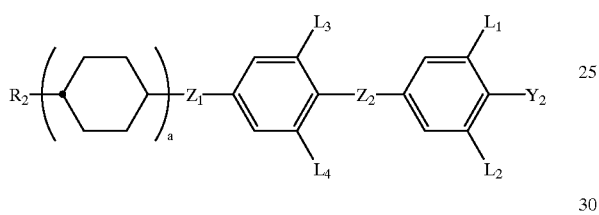

wherein $R_2$ represents an alkyl group of 1–10 carbon atoms; $Y_2$ represents a fluorine atom, a chlorine atom, $OCF_3$, $OCHF_2$, $CF_3$, $CHF_2$ or $CH_2F$; $L_1$, $L_2$, $L_3$ and $L_4$, each independently, represent a hydrogen atom or a fluorine atom; $Z_1$ and $Z_2$, each independently, represent —$CH_2CH_2$—, —CH=CH— or a covalent bond; and a represents 1 or 2, and at least one compound selected from the group consisting of compounds represented by general formulas (5), (6), (7), (8) and (9) as a third component:

(5)

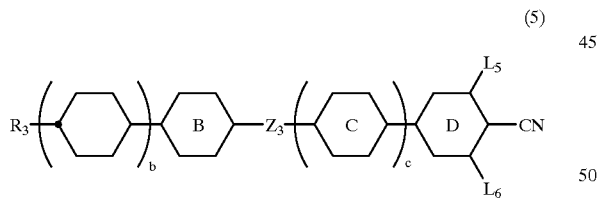

wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cyclohexylene or 1,4-phenylene; $Z_3$ represents —$CH_2CH_2$—, —COO— or a covalent bond; $L_5$ and $L_6$, each independently, represent a hydrogen atom or a fluorine atom, b and c, each independently, represent 0 or 1, (6)

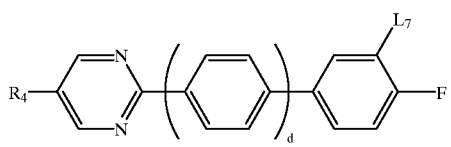

wherein $R_4$ represents an alkyl group of 1–10 carbon atoms, $L_7$ represents a hydrogen atom or a fluorine atom, and d represents 0 or 1, (7)

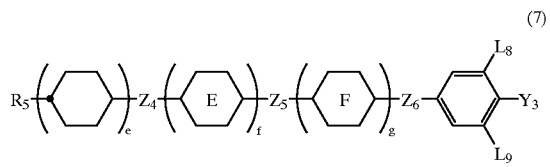

wherein $R_5$ represents an alkyl group of 1–10 carbon atoms; six-membered ring E and six-membered ring F represent, each independently, trans-1,4-cyclohexylene or 1,4-phenylene; $Z_4$ and $Z_5$, each independently, represent —COO— or a covalent bond; $Z_6$ represents —COO— or —C≡C—; $L_8$ and $L_9$, each independently, represent a hydrogen atom or a fluorine atom; $Y_3$ represents a fluorine atom, $OCF_3$, $OCHF_2$, $CF_3$, $CHF_2$ or $CH_2F$; e, f and g, each independently, represent 0 or 1; and e, f and g are not 0 at the same time; when e is 0, $Z_4$ is a covalent bond; when f or g is 0, $Z_5$ is a covalent bond; and when f and g are 0, $Z_4$ is also a covalent bond, (8)

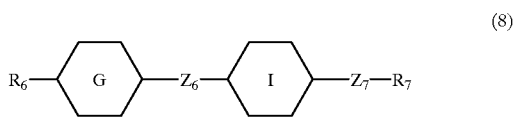

wherein $R_6$ and $R_7$, each independently, represent an alkyl group of 1–10 carbon atoms or an alkenyl group of 2–10 carbon atoms, in which one or more not-adjacenl methylene groups may be replaced by an oxygen atom; six-membered ring G represents trans-1,4-cyclohexylene, 1,4-phenylene or pyrimidine-2,5-diyl; six-membered ring I represents trans-1,4-cyclohexylene or 1,4-phenylene; $Z_6$ represents —C≡C—, —COO—, —$CH_2CH_2$—, —CH=CH—C≡C— or a covalent bond; and $Z_7$ represents —COO— or a covalent bond, (9)

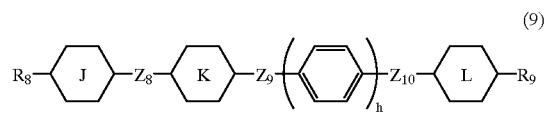

wherein $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring J represents trans-1,4-cyclohexylene, 1,4-phenylene or pyrimidine-2,5-diyl; six-membered ring K represents trans-1,4-cyclohexylene, pyrimidine-2,5-diyl or 1,4-phenylene, in which one or more hydrogen atoms may be substituted by fluorine atoms at the side; six-membered ring L represents trans-1,4-cyclohexylene or 1,4-phenylene; $Z_8$ and $Z_{10}$, each independently, represent —COO—, —CH$_2$CH$_2$— or a covalent bond; $Z_9$ represents —CH=CH—, —C≡C—, —COO— or a covalent bond, and h represents 0 or 1; and when h is 0, at least any one of $Z_9$ and $Z_{10}$ is a covalent bond.

13. A liquid crystalline acetylene derivative represented by the following formula:

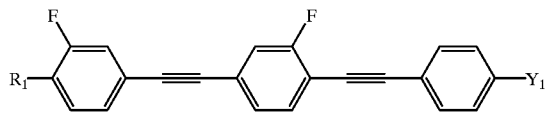

wherein $R_1$ represents an alkyl group of 1–5 carbon atoms; and $Y_1$ is replaced by $R_1$, a fluorine atom, a chlorine atom, a bromine atom, an iodine atom or a cyano group.

14. A liquid crystal composition comprising at least one liquid crystalline acetylene derivative according to claim 13 as a first component, and at least one compound selected from the group consisting of compounds represented by general formulas (2), (3) and (4) as a second component, (2)

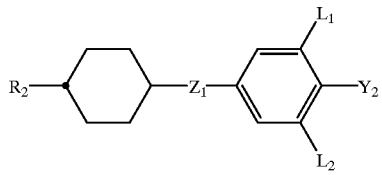

(3)

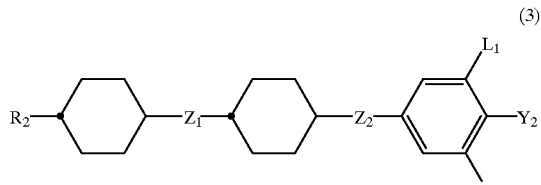

(4)

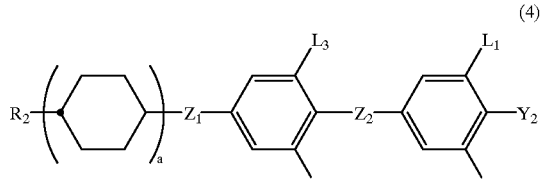

wherein $R_2$ represents an alkyl group of 1–10 carbon atoms; $Y_2$ represents a fluorine atom, a chlorine atom, OCF$_3$, OCHF$_2$, CF$_3$, CHF$_2$ or CH$_2$F; $L_1$, $L_2$, $L_3$, and $L_4$, each independently, represent a hydrogen atom or a fluorine atom; $Z_1$ and $Z_2$, each independently, represent —CH$_2$CH$_2$—, —CH=CH— or a covalent bond; and a representing 1 or 2.

15. A liquid crystal composition comprising at least one liquid crystalline acetylene derivative according to claim 13 as a first component, and at least one compound selected from the group consisting of compounds represented by general formulas (5), (6), (7), (8) and (9) as a second component:

(5)

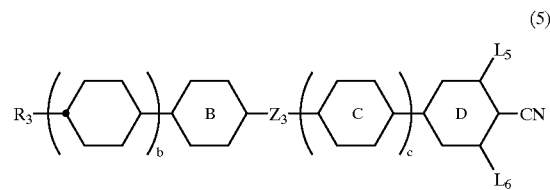

wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cydohexylene or 1,4-phenylene; $Z_3$ represents —CH$_2$CH$_2$—, —COO— or a covalent bond; $L_5$ and $L_6$, each independently, represent a hydrogen atom or a fluorine atom, b and c, each independently, represent 0 or 1, (6)

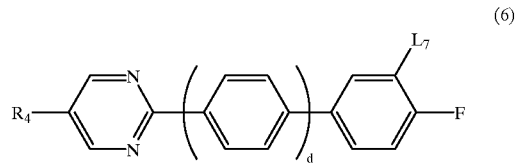

wherein $R_4$ represents an alkyl group of 1–10 carbon atoms; $L_7$ represents a hydrogen atom or a fluorine atom; and d represents 0 or 1, (7)

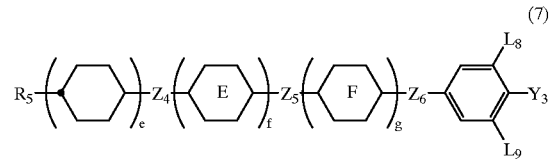

wherein $R_5$ represents an alkyl group of 1–10 carbon atoms; six-membered ring E and six-membered ring F represent, each independently, trans-1,4-cydohexylene or 1,4-phenylene; $Z_4$ and $Z_5$, each independently, represent —COO— or a covalent bond; $Z_6$ represents —COO— or —C≡C—; $L_8$ and $L_9$, each independently, represent a hydrogen atom or a fluorine atom; $Y_3$ represents a fluorine atom, OCF$_3$, OCHF$_2$, CF$_3$, CHF$_2$ or CH$_2$F; e, f and g, each independently, represent 0 or 1; and e, f and g are not 0 at the same time; when e is 0, $Z_4$ is a covalent bond; when f or g is 0, $Z_5$ is a covalent bond; and when f and g are 0, $Z_4$ is also a covalent bond, (8)

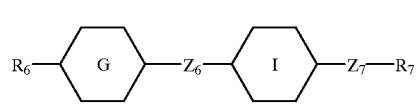

wherein $R_6$ and $R_7$, each independently, represent an alkyl group of 1–10 carbon atoms or an alkenyl group of 2–10 carbon atoms, in which one or more not-adjacent methylene groups may be replaced by an oxygen atom;

six-membered ring G represents trans-1,4-cydohexylene, 1,4-phenylene or pyrimidine-2,5-diyl; six-membered ring I represents trans-1,4-cyclohexylene or 1,4-phenylene; $Z_6$ represents —C≡C—, —COO—, —CH$_2$CH$_2$—, —CH=CH— C≡C— or a covalent bond; and $Z_7$ represents —COO— or a covalent bond,

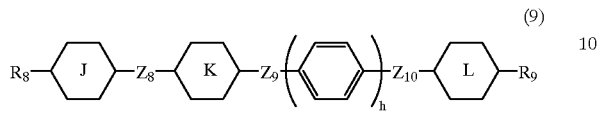

(9)

wherein $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring J represents trans-1,4-cyclohexylene, 1,4-phenylene or pyrimidine-2,5-diyl; six-membered ring K represents trans-1,4-cyclohexylene, pyrimidine-2,5-diyl or 1,4-phenylene, and in which one or more hydrogen atoms may be substituted by fluorine atoms at the side; six-membered ring L represents trans-1,4-cyclohexylene or 1,4-phenylene; $Z_8$ and $Z_{10}$, each independently, represent —COO—, —CH$_2$CH$_2$— or a covalent bond; $Z_9$ represents —CH=CH—, —C≡C—, —COO— or a covalent bond, and h represents 0 or 1; and when h is 0, at least any one of $Z_9$ and $Z_{10}$ are a covalent bond.

16. A liquid crystal composition comprising at least one liquid crystalline acetylene derivative according to claim 13 as a first component, and comprising at least one compound selected from the group consisting of compounds represented by general formulas (2), (3) and (4) as a second component:

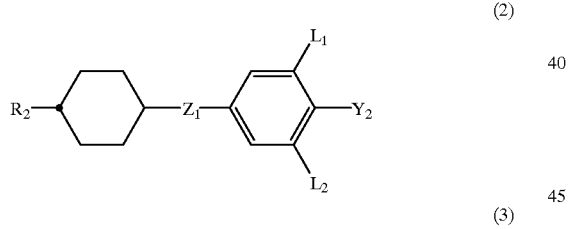

(2)

(3)

(4)

wherein $R_2$ represents an alkyl group of 1–10 carbon atoms; $Y_2$ represents a fluorine atom, a chlorine atom, OCF$_3$, OCHF$_2$, CF$_3$, CHF$_2$ or CH$_2$F; $L_1$, $L_2$, $L_3$ and $L_4$, each independently, represent a hydrogen atom or a fluorine atom;

$Z_1$ and $Z_2$, each independently, represent —CH$_2$CH$_2$—, —CH=CH— or a covalent bond; and a represents 1 or 2, and at least one compound selected from the group consisting of compounds represented by general formulas (5), (6), (7), (8) and (9) as a third component:

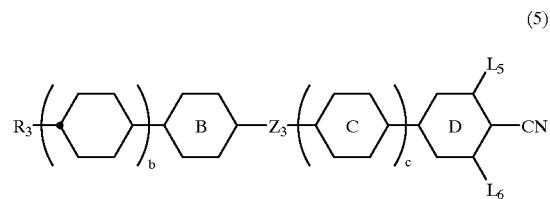

(5)

wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cyclohexylene or 1,4-phenylene; $Z_3$ represents —CH$_2$CH$_2$—, —COO— or a covalent bond; $L_5$ and $L_6$, each independently, represent a hydrogen atom or a fluorine atom, b and c, each independently, represent 0 or 1,

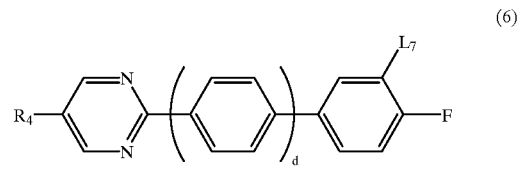

(6)

wherein $R_4$ represents an alkyl group of 1–10 carbon atoms, $L_7$ represents a hydrogen atom or a fluorine atom, and d represents 0 or 1,

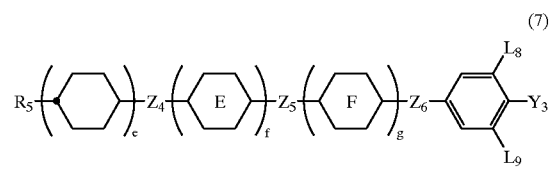

(7)

wherein $R_5$ represents an alkyl group of 1–10 carbon atoms; six-membered ring E and six-membered ring F represent, each independently, trans-1,4-cyclohexylene or 1,4-phenylene; $Z_4$ and $Z_5$, each independently, represent —COO— or a covalent bond; $Z_6$ represents —COO— or —C≡C—; $L_8$ and $L_9$, each independently, represent a hydrogen atom or a fluorine atom; $Y_3$ represents a fluorine atom, OCF$_3$, OCHF$_2$, CF$_3$, CHF$_2$ or CH$_2$F; e, f and g, each independently, represent 0 or 1; and e, f and g are not 0 at the same time; when e is 0, $Z_4$ is a covalent bond; when f or g is 0, $Z_5$ is a covalent bond; and when f and g are 0, $Z_4$ is also a covalent bond,

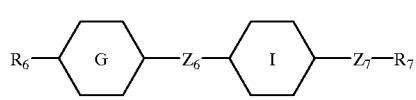
(8)

wherein $R_6$ and $R_7$, each independently, represent an alkyl group of 1–10 carbon atoms or an alkenyl group of 2–10 carbon atoms, in which one or more not-adjacent methylene groups may be replaced by an oxygen atom; six-membered ring G represents trans-1,4-cyclohexylene, 1,4-phenylene or pyrimidine-2,5-diyl; six-membered ring I represents trans-1,4-cyclohexylene or 1,4-phenylene; $Z_6$ represents —C≡C—, —COO—, —CH$_2$CH$_2$—, —CH=CH—C≡C— or a covalent bond; and $Z_7$ represents —COO— or a covalent bond, (9)

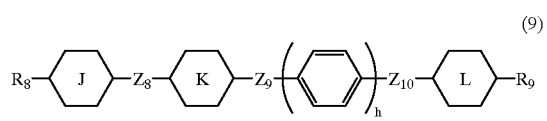

wherein $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring J represents trans-1,4-cyclohexylene, 1,4-phenylene or pyrimidine-2,5-diyl; six-membered ring K represents trans-1,4-cyclohexylene, pyrimidine-2,5-diyl or 1,4-phenylene, in which one or more hydrogen atoms may be substituted by fluorine atoms at the side; six-membered ring L represents trans-1,4-cyclohexylene or 1,4-phenylene; $Z_8$ and $Z_{10}$, each independently, represent —COO—, —CH$_2$CH$_2$— or a covalent bond; $Z_9$ represents —CH=CH—, —C≡C—, —COO— or a covalent bond, and h represents 0 or 1; and when h is 0, at least any one of $Z_9$ and $Z_{10}$ is a covalent bond.

17. A liquid crystalline acetylene derivative represented by the following formula:

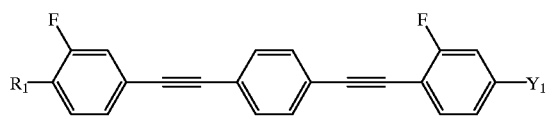

wherein $R_1$ represents an alkyl group of 1–5 carbon atoms; and $Y_1$ is replaced by $R_1$, a fluorine atom, a chlorine atom, a bromine atom, an iodine atom or a cyano group.

18. A liquid crystal composition comprising at least one liquid crystalline acetylene derivative according to claim 17 as a first component, and at least one compound selected from the group consisting of compounds represented by general formulas (2), (3) and (4) as a second component,

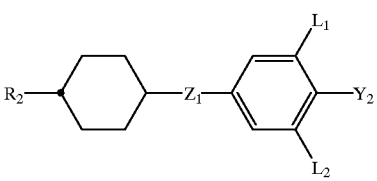
(2)

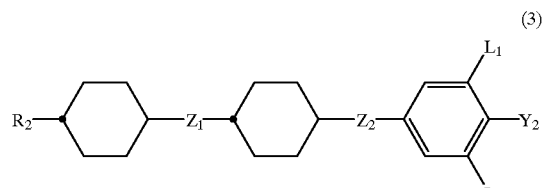
(3)

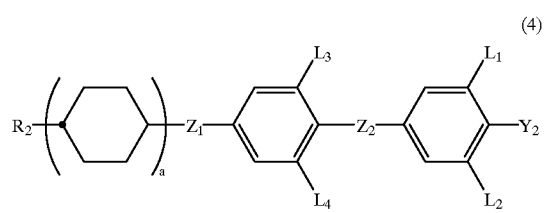
(4)

wherein $R_2$ represents an alkyl group of 1–10 carbon atoms; $Y_2$ represents a fluorine atom, a chlorine atom, OCF$_3$, OCHF$_2$, CF$_3$, CHF$_2$ or CH$_2$F; $L_1$, $L_2$, $L_3$ and $L_4$, each dependently, represent a hydrogen atom or a fluorine atom; $Z_1$ and $Z_2$, each independently, represent —CH$_2$CH$_2$—, —CH=CH— or a covalent bond; and a represents 1 or 2.

19. A liquid crystal composition comprising at least one liquid crystalline acetylene derivative according to claim 17 as a first component, and comprising at least one compound selected from the group consisting of compounds represented by general formulas (2), (3) and (4) as a second component:

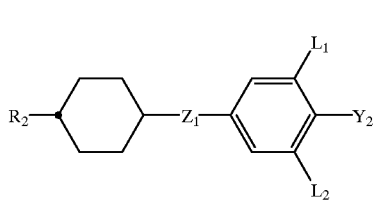
(2)

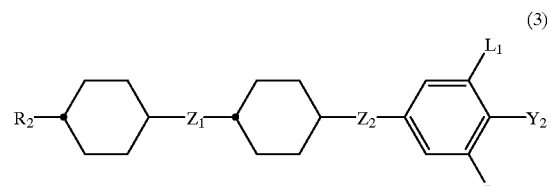
(3)

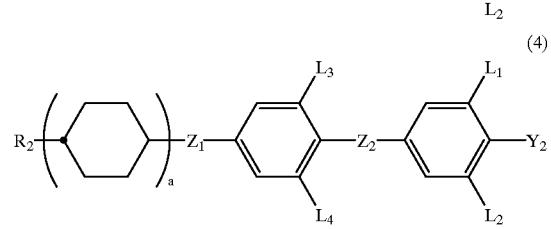
(4)

wherein $R_2$ represents an alkyl group of 1–10 carbon atoms; $Y_2$ represents a fluorine atom, a chlorine atom, OCF$_3$, OCHF$_2$, CF$_3$, CHF$_2$ or CH$_2$F; $L_1$, $L_2$, $L_3$ and $L_4$, each independently, represent a hydrogen atom or a fluorine atom; $Z_1$ and $Z_2$, each independently, represent —CH$_2$CH$_2$—, —CH=CH— or a covalent bond; and a represents 1 or 2, and at least one compound selected from the group consisting of compounds represented by general formulas (5), (6), (7), (8) and (9) as a third component:

(5)

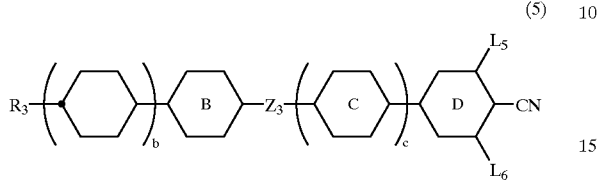

wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cyclohexylene or 1,4-phenylene; $Z_3$ represents —CH$_2$CH$_2$—, —COO— or a covalent bond; $L_5$ and $L_6$, each independently, represent a hydrogen atom or a fluorine atom, b and c, each independently, represent 0 or 1, (6)

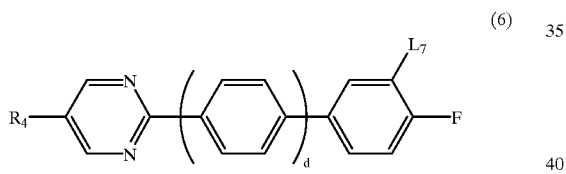

wherein $R_4$ represents an alkyl group of 1–10 carbon atoms, $L_7$ represents a hydrogen atom or a fluorine atom, and d represents 0 or 1, (7)

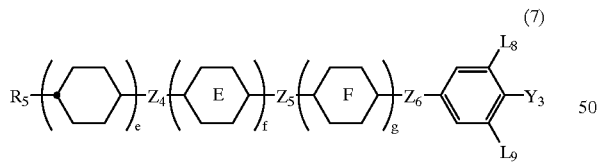

wherein $R_5$ represents an alkyl group of 1–10 carbon atoms; six-membered ring E and six-membered ring F represent, each independently, trans-1,4-cyclohexylene or 1,4-phenylene; $Z_4$ and $Z_5$, each independently, represent —COO— or a covalent bond; $Z_6$ represents —COO— or —C≡C—; $L_8$ and $L_9$, each independently, represent a hydrogen atom or a fluorine atom; $Y_3$ represents a fluorine atom, OCF$_3$, OCHF$_2$, CF$_3$, CHF$_2$ or CH$_2$F; e, f and g, each independently, represent 0 or 1; and e, f and g are not 0 at the same time; when e is 0, $Z_4$ is a covalent bond; when f or g is 0, $Z_5$ is a covalent bond; and when f and g are 0, $Z_4$ is also a covalent bond, (8)

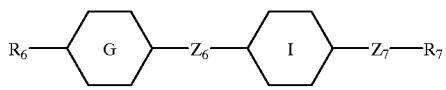

wherein $R_6$ and $R_7$, each independently, represent an alkyl group of 1–10 carbon atoms or an alkenyl group of 2–10 carbon atoms, in which one or more not-adjacent methylene groups may be replaced by an oxygen atom; six-membered ring G represents trans-1,4-cyclohexylene, 1,4-phenylene or pyrimidine-2,5-diyl; six-membered ring I represents trans-1,4-cyclohexylene or 1,4-phenylene; $Z_6$ represents —C≡C—, —COO—, —CH$_2$CH$_2$—, —CH=CH—C≡C— or a covalent bond; and $Z_7$ represents —COO— or a covalent bond, (9)

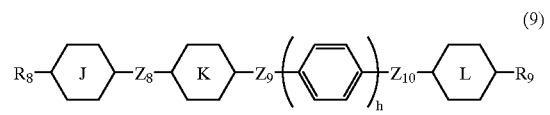

wherein $R_8$ and $R_9$, each independently, represent an alkyl group of 1–10 carbon atoms or an alkenyl group of 2–10 carbon atoms, in which one or more not-adjacent methylene groups may be replaced by an oxygen tom; six-membered ring J represents trans-1,4-cyclohexylene, 1,4-phenylene or pyrimidine-2,5-diyl; six-membered ring K represent trans-1,4-cyclohexylene, pyrimidine-2,5-diyl or 1,4-phenylene, in which one or more hydrogen atoms may be substituted by fluorine atoms at the side; six-membered ring L represents trans-1,4-cyclohexylene or 1,4-phenylene; $Z_8$ and $Z_{10}$, each independently, represent —COO—, —CH$_2$CH$_2$— or a covalent bond; $Z_9$ represents —CH=CH—, —C≡C—, —COO— or a covalent bond, and h represents 0 or 1; and when h is 0, at least any one of $Z_9$ and $Z_{10}$ is a covalent bond.

20. A liquid crystal composition comprising at least one liquid crystalline acetylene derivative according to claim 17 as a first component, and comprising at least one compound selected from the group consisting of compounds represented by general formulas (2), (3) and (4) as a second component:

(2)

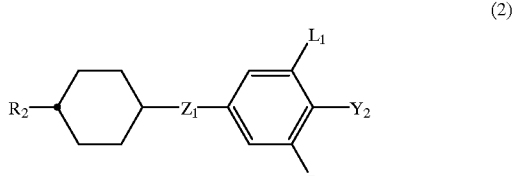

(3)

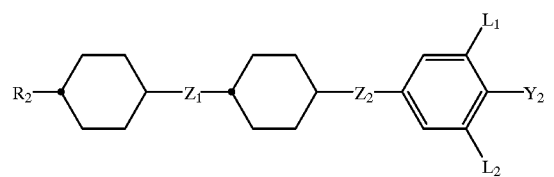

-continued (4)

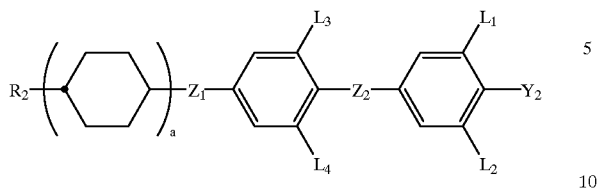

wherein $R_2$ represents an alkyl group of 1–10 carbon atoms; $Y_2$ represents a fluorine atom, a chlorine atom, $OCF_3$, $OCHF_2$, $CF_3$, $CHF_2$ or $CH_2F$; $L_1$, $L_2$, $L_3$ and $L_4$, each independently, represent a hydrogen atom or a fluorine atom; $Z_1$ and $Z_2$, each independently, represent —$CH_2CH_2$—, —CH=CH— or a covalent bond; and a represents 1 or 2, and at least one compound selected from the group consisting of compounds represented by general formulas (5), (6), (7), (8) and (9) as a third component:

(5)

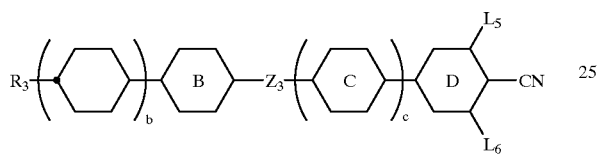

wherein $R_3$ represents a fluorine atom, an alkyl group of 1–10 carbon atoms or an alkenyl group of 2–10 carbon atoms, in which one or more not-adjacent methylene groups may be replaced by an oxygen atom; six-membered ring B represents trans-1,4-cyclohexylene, 1,4-phenylene or 1,3-dioxane-trans-2,5-diyl; six-membered ring C represents trans-1,4-cyclohexylene, 1,4-phenylene or pylimidine-2,5-diyl; six-membered ring D represents trans-1,4-cyclohexylene or 1,4-phenylene; $Z_3$ represents —$CH_2CH_2$—, —COO— or a covalent bond; $L_5$ and $L_6$, each independently, represent a hydrogen atom or a fluorine atom, b and c, each independently, represent 0 or 1, (6)

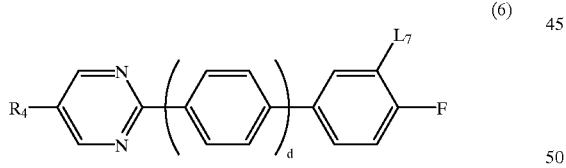

wherein $R_4$ represents an alkyl group of 1–10 carbon atoms, $L_7$ represents a hydrogen atom or a fluorine atom, and d represents 0 or 1, (7)

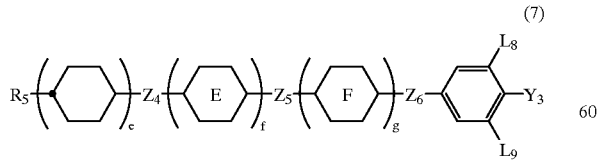

wherein $R_5$ represents an alkyl group of 1–10 carbon atoms; six-membered ring E and six-membered ring F represent, each independently, trans-1,4-cyclohexylene or 1,4-phenylene; $Z_4$ and $Z_5$, each independently, represent —COO— or a covalent bond; $Z_6$ represents —COO— or —C≡C—; $L_8$ and $L_9$, each independently, represent a hydrogen atom or a fluorine atom; $Y_3$ represents a fluorine atom, $OCF_3$, $OCHF_2$, $CF_3$, $CHF_2$ or $CH_2F$; e, f and g, each independently, represent 0 or 1; and e, f and g are not 0 at the same time; when e is 0, $Z_4$ is a covalent bond; when f or g is 0, $Z_5$ is a covalent bond; and when f and g are 0, $Z_4$ is also a covalent bond, (8)

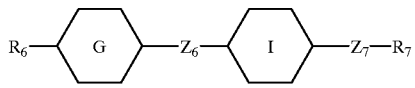

wherein $R_6$ and $R_7$, each independently, represent an alkyl group of 1–10 carbon atoms or an alkenyl group of 2–10 carbon atoms, in which one or more not-adjacent methylene groups may be replaced by an oxygen atom; six-membered ring G represents trans-1,4-cyclohexylene, 1,4-phenylene or pyrimidine-2,5-diyl; six-membered ring I represents trans-1,4-cyclohexylene or 1,4-phenylene; $Z_6$ represents —C≡C—, —COO—, —$CH_2CH_2$—, —CH=CH—C≡C— or a covalent bond; and $Z_7$ represents —COO— or a covalent bond, (9)

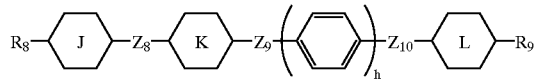

wherein $R_8$ and $R_9$, each independently, represent an alkyl group of 1–10 carbon atoms or an alkenyl group of 2–10 carbon atoms, in which one or more not-adjacent methylene groups may be replaced by an oxygen atom; six-membered ring J represents trans-1,4-cyclohexylene, 1,4-phenylene or pyrimidine-2,5-diyl; six-membered ring K represents trans-1,4-cyclohexylene, pyrimidine-2,5-diyl or 1,4-phenylene, in which one or more hydrogen atoms may be substituted by fluorine atoms at the side; six-membered ring L represents trans-1,4-cyclohexylene or 1,4-phenylene; $Z_8$ and $Z_{10}$, each independently, represent —COO—, —$CH_2CH_2$— or a covalent bond; $Z_9$ represents —CH=CH—, —C≡C—, —COO— or a covalent bond, and h represents 0 or 1; and when h is 0, at least any one of $Z_9$ and $Z_{10}$ is a covalent bond.

21. A liquid crystal composition comprising at least one liquid crystalline acetylene derivative, and at least one additional compound as an at least second component, said liquid crystalline acetylene derivative comprising a compound of formula (1):

(1)

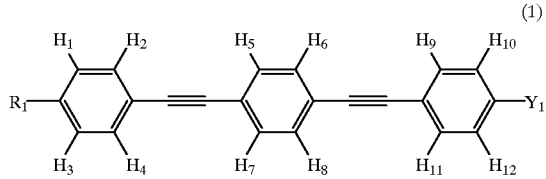

wherein $H_1$, $H_2$, $H_3$, $H_4$, $H_5$, $H_6$, $H_7$, $H_8$, $H_9$, $H_{10}$, $H_{11}$ and $H_{12}$, each independently, represent a hydrogen atom, a fluorine atom, or a chlorine atom, at least one of $H_1$, $H_2$, $H_3$, $H_4$, $H_9$, $H_{10}$, $H_{11}$ and $H_{12}$ is a fluorine or chlorine atom, $R_1$ represent an alkyl group of 1–20 carbon atoms, in which one or more not-adjacent methylene groups may be replaced by an oxygen atom, a sulfur atom, dihydroxysilylene, dimethylsilylene, —CH=CH— or —C≡C, any hydrogen atoms in the group may be substituted by a halogen atom, and $Y_1$ may be replaced by $R_1$, a fluorine atom, a chlorine atom, a bromine atom, an iodine atom or a cyano group, with the proviso that $R_1$ and $Y_1$ are not an alkoxy group having the same chain length at the same time; and wherein said at least one compound is selected from the group consisting of compounds of formulas (2), (3), and (4) as at least one said second component,

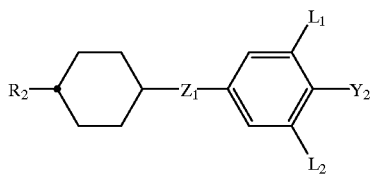

(2)

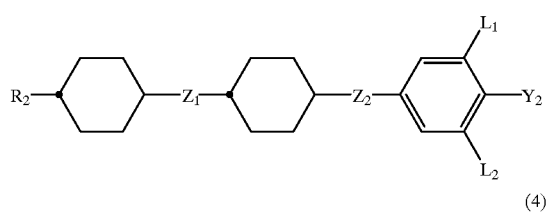

(3)

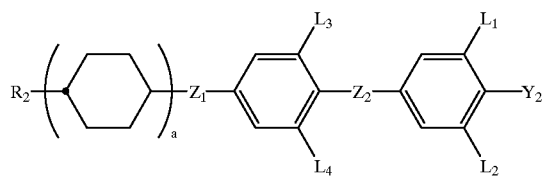

(4)

wherein $R_2$ represents an alkyl group of 1–10 carbon atoms; $Y_2$ represents a fluorine atom, a chlorine atom, $OCF_3$, $OCHF_2$, $CF_3$, $CHF_2$ or $CH_2F$; $L_1$, $L_2$, $L_3$ and $L_4$, each independently, represent a hydrogen atom or a fluorine atom; $Z_1$ and $Z_2$, each independently, represent —$CH_2CH_2$—, —CH=CH— or covalent bond; and represents 1 or 2.

* * * * *